US012767946B2

(12) United States Patent
Khvorova et al.

(10) Patent No.: US 12,767,946 B2
(45) **Date of Patent: *Oct. 20, 2026**

(54) OLIGONUCLEOTIDES FOR TISSUE SPECIFIC ApoE MODULATION

(71) Applicant: UNIVERSITY OF MASSACHUSETTS, Boston, MA (US)

(72) Inventors: Anastasia Khvorova, Westborough, MA (US); Chantal Ferguson, Worcester, MA (US); Evgeny Rogaev, Shrewsbury, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/818,563

(22) Filed: Mar. 13, 2020

(65) Prior Publication Data

US 2020/0362341 A1 Nov. 19, 2020

Related U.S. Application Data

(60) Provisional application No. 62/951,441, filed on Dec. 20, 2019, provisional application No. 62/864,797, filed on Jun. 21, 2019, provisional application No. 62/819,189, filed on Mar. 15, 2019.

(51) Int. Cl.
*C12N 15/113* (2010.01)
*A61K 9/00* (2006.01)

(52) U.S. Cl.
CPC .......... *C12N 15/113* (2013.01); *A61K 9/0019* (2013.01); *C12N 2310/14* (2013.01); *C12N 2310/315* (2013.01); *C12N 2310/321* (2013.01); *C12N 2310/322* (2013.01); *C12N 2310/3515* (2013.01); *C12N 2310/52* (2013.01)

(58) Field of Classification Search
CPC .............. C12N 15/113; C12N 2310/14; C12N 2310/315; C12N 2310/321; C12N 2310/322; C12N 2310/52
See application file for complete search history.

(56) References Cited

U.S. PATENT DOCUMENTS

| | | | | |
|---|---|---|---|---|
| 4,522,811 | A | 6/1985 | Eppstein et al. | |
| 5,684,142 | A | 11/1997 | Mishra et al. | |
| 5,814,014 | A | 9/1998 | Elsberry et al. | |
| 6,093,180 | A | 7/2000 | Elsberry | |
| 6,107,094 | A | 8/2000 | Crooke | |
| 6,471,996 | B1 | 10/2002 | Sokoll et al. | |
| 7,459,547 | B2 | 12/2008 | Zamore et al. | |
| 7,732,593 | B2 | 6/2010 | Zamore et al. | |
| 7,750,144 | B2 | 7/2010 | Zamore et al. | |
| 7,772,203 | B2 | 8/2010 | Zamore et al. | |
| 8,304,530 | B2 | 11/2012 | Zamore et al. | |
| 8,309,704 | B2 | 11/2012 | Zamore et al. | |
| 8,309,705 | B2 | 11/2012 | Zamore et al. | |
| 8,329,892 | B2 | 12/2012 | Zamore et al. | |
| 8,431,544 | B1 | 4/2013 | Agrawal et al. | |
| 2005/0220766 | A1 | 10/2005 | Amalfitano et al. | |
| 2005/0246794 | A1* | 11/2005 | Khvorova | C12N 15/1137 536/23.1 |
| 2006/0078542 | A1 | 4/2006 | Mah et al. | |
| 2006/0257851 | A1 | 11/2006 | Bentwich | |
| 2007/0031844 | A1* | 2/2007 | Khvorova | A61P 3/10 435/6.13 |
| 2007/0259827 | A1 | 11/2007 | Aronin et al. | |
| 2008/0269149 | A1 | 10/2008 | Bowles et al. | |
| 2008/0293655 | A1 | 11/2008 | Aygun et al. | |
| 2010/0186103 | A1 | 7/2010 | Gao et al. | |
| 2010/0310553 | A1 | 12/2010 | Luo et al. | |
| 2011/0178283 | A1* | 7/2011 | Rigoutsos | G16B 30/00 536/24.5 |
| 2014/0296486 | A1 | 10/2014 | Gao et al. | |
| 2015/0141320 | A1 | 5/2015 | Krieg et al. | |
| 2017/0218376 | A1* | 8/2017 | Lee | A61P 11/06 |
| 2017/0312367 | A1* | 11/2017 | Khvorova | A61K 31/7084 |
| 2017/0334977 | A1 | 11/2017 | Butovsky et al. | |

FOREIGN PATENT DOCUMENTS

| | | | | |
|---|---|---|---|---|
| EP | 2213738 A2 | 8/2010 | | |
| EP | 3937951 A1 | 1/2022 | | |
| KR | 10-1029699 B1 | 4/2011 | | |
| WO | WO 2003/029459 A2 | 4/2003 | | |
| WO | WO 2004/045543 A2 | 6/2004 | | |
| WO | WO 2007/098417 A2 | 8/2007 | | |
| WO | WO-2009147684 A2 * | 12/2009 | | A61K 31/713 |
| WO | WO-2010129799 A2 * | 11/2010 | | A61K 31/713 |
| WO | WO 2011/031520 A1 | 3/2011 | | |

(Continued)

OTHER PUBLICATIONS

Pencheva et al., Convergent Multi-miRNA Targeting of ApoE Drives LRP1/LRP8-Dependent Melanoma Metastasis and Angiogenesis, Cell, 2012, 151: 1068-1082 and supplemental information, pp. S1-S13 (Year: 2012).*

PCT International Search Report and Written Opinion for PCT International Patent Application No. PCT/US2020/022748, mailed Aug. 6, 2020.

Alisky et al., "Gene therapy for amyotrophic lateral sclerosis and other motor neuron diseases", Hum Gene Ther.,11(17):2315-2329, doi: 10.1089/104303400750038435, (Nov. 20, 2000).

Altschul et al. (1997) "Gapped BLAST and PSI-BLAST: a new generation of protein database search programs," Nucleic Acids Res. 25(17):3389-3402.

Altschul, et al., "Basic local alignment search tool", J Mol Biol., 215(3):403-10, doi: 10.1016/S0022-2836(05)80360-2, (Oct. 5, 1990).

Alvarez-Erviti et al., "Delivery of siRNA to the mouse brain by systemic injection of targeted exosomes", Nat Biotechnol., 29(4):341-345, doi: 10.1038/nbt.1807, (Apr. 2011).

(Continued)

*Primary Examiner* — Ekaterina Poliakova-Georgantas
(74) *Attorney, Agent, or Firm* — LATHROP GPM LLP; James H. Velema, Esq.

(57) ABSTRACT

This disclosure relates to novel ApoE targeting sequences. Novel oligonucleotides for the treatment of neurodegenerative and amyloid-related diseases are also provided.

17 Claims, 58 Drawing Sheets

Specification includes a Sequence Listing.

(56) References Cited

FOREIGN PATENT DOCUMENTS

| | | | |
|---|---|---|---|
| WO | WO 2013/173652 | A1 | 11/2013 |
| WO | WO 2013/181618 | A2 | 12/2013 |
| WO | WO 2016/040794 | A1 | 3/2016 |
| WO | WO 2016/163839 | A1 | 10/2016 |
| WO | WO 2017/132669 | A1 | 8/2017 |
| WO | WO 2020/190768 | A1 | 9/2020 |
| WO | WO 2021/133941 | A1 | 7/2021 |

OTHER PUBLICATIONS

Ambros et al., "MicroRNAs and other tiny endogenous RNAs in C. elegans", Curr Biol, 13, 807-18, doi:10.1016/S0960-9822(03)00287-2, (2003).
Atwell et al., "Stable heterodimers from remodeling the domain interface of a homodimer using a phage display library", J Mol Biol., 270(1):26-35, doi: 10.1006/jmbi.1997.1116, (Jul. 4, 1997).
Bagella et al. (1998) "Cloning of murine CDK9/PITALRE and its tissue-specific expression in development," J. Cell. Physiol. 177:206-213.
Billy et al., "Specific interference with gene expression induced by long, double-stranded RNA in mouse embryonal teratocarcinoma cell lines", Proc Natl Acad Sci USA. 2001, 98(25): 14428-14433.
Braasch et al. (2003) "RNA Interference in Mammalian Cells by Chemically-Modified RNA," Biochemistry 42:7967-7975.
Brennecke et al. (2003) "Towards a complete description of the microRNA complement of animal genomes," Genome Biol. 4(9):228.
Brummelkamp et al. (2002) "A system for stable expression of short interfering RNAs in mammalian cells," Science. 296:550-553.
Calegari et al. (2002) "Tissue-specific RNA interference in postimplantation mouse embryos with endoribonuclease-prepared short interfering RNA," Proc. Natl. Acad. Sci. USA. 99(22):14236-14240.
Carter, "Handbook of Parvoviruses", ed., P. Tijsser, CRC Press, pp. 155-168, 1990.
Davidson et al., "A model system for in vivo gene transfer into the central nervous system using an adenoviral vector", Nat Genet., 3(3):219-23, doi: 10.1038/ng0393-219, (Mar. 1993).
Davidson et al., "Recombinant adeno-associated virus type 2, 4, and 5 vectors: Transduction of variant cell types and regions in the mammalian central nervous system", PNAS, 97(7):3428-3432, doi.org/10.1073/pnas.97.7.3428, (Mar. 28, 2000).
Doench et al. (2003) "siRNAs can function as miRNAs," Genes Dev. 17(4):438-442.
Eckstein, Antisense Nucleic Acid Drug Dev., Apr. 10, 2000, 10(2): 117-121.
Egusquiaguirre et al., "Nanoparticle delivery systems for cancer therapy: advances in clinical and preclinical research", Clin Transl Oncol., 14(2):83-93, doi: 10.1007/s12094-012-0766-6, (Feb. 2012).
El Andaloussi et al., "Exosomes for targeted siRNA delivery across biological barriers", Adv Drug Deliv Rev., 65(3):391-397, doi: 10.1016/j.addr.2012.08.008, (Mar. 2013).
El Andaloussi et al., "Extracellular vesicles: biology and emerging therapeutic opportunities", Nat Rev Drug Discov., 12(5):347-357, doi: 10.1038/nrd3978, (May 2013).
El-Andaloussi et al., "Exosome-mediated delivery of siRNA in vitro and in vivo", Nat Protoc., 7(12):2112-2126, doi: 10.1038/nprot.2012.131, (2012).
Elmen et al. (2005) "Locked nucleic acid (LNA) mediated improvements in siRNA stability and functionality," Nucleic Acids Res. 33(1):439-447.
Fattal et al., "Biodegradable polyalkylcyanoacrylate nanoparticles for the delivery of oligonucleotides", J Control Release, 53(1-3):137-43, doi: 10.1016/s0168-3659(97)00246-0, (Apr. 30, 1998).
Ferguson et al., "Targeting Apolipoprotein E expression with tissue specific small interfering RNAs", RNA Therapeutics Institute, Nature Biotechnology, 2019, 1 page.
Fisher et al., "Transduction with Recombinant Adeno-Associated Virus for Gene Therapy Is Limited by Leading-Strand Synthesis", J Virol., 70:520 532, (Jan. 1996).
Giege et al., "Crystallization of Nucleic Acids and Proteins, a Practical Approach", $2^{nd}$ eds., pp. 20 1-16, Oxford University Press, New York, New York, (1999).
Godard et al. (1995) "Antisense Effects of Cholesterol-Oligodeoxynucleotide Conjugates Associated with Poly(alkylcyanoacrylate) Nanoparticles," Eur. J. Biochem. 232(2):404-410.
Goodson, in Medical Applications of Controlled Release, vol. 2, pp. 115-138, (1984).
Hammerling et al., Monoclonal Antibodies and T-Cell Hybridomas, Research Monographs in Immunology, vol. 3, pp. 563-681, 1981.
Herdewijn (2000) "Heterocyclic modifications of oligonucleotides and antisense technology," Antisense Nucleic Acid Drug Dev. 10(4):297-310.
Hutvagner et al. (2002) "A microRNA in a multiple-turnover RNAi enzyme complex," Science. 297(5589):2056-2060.
Huynh et al., "Age-Depensent Effects of apoE Reduction Using Antisense Oligonucleotides in a Model of β-amyloidosis", Neuron, 2017, 96: 1013-1023.
International Preliminary Examination Report for PCT International Patent Application No. PCT/US2020/022748, dated Sep. 21, 2021.
Jacque et al. (2002) "Modulation of HIV-1 replication by RNA interference," Nature. 418:435-438.
Lagos-Quintana et al. (2001) "Identification of novel genes coding for small expressed RNAs," Science. 294(5543):853-858.
Lagos-Quintana et al., "Identification of tissue-specific microRNAs from mouse", Curr Biol., 12(9):735-739, doi: 10.1016/s0960-9822(02)00809-6, (Apr. 30, 2002).
Lagos-Quintana et al., "New microRNAs from mouse and human", RNA, 9(2):175-179, doi: 10.1261/rna.2146903, (Feb. 2003).
Lam et al., "A New Type of Synthetic Peptide Library For Identifying Ligand-Binding Activity", Nature, vol. 354, pp. 82-84, Nov. 7, 1991.
Lambert et al., "Nanoparticulate systems for the delivery of antisense oligonucleotides", Adv Drug Deliv Rev., 47(1):99-112, doi: 10.1016/s0169-409x(00)00116-2, (Mar. 23, 2001).
Lau et al. (2001) "An abundant class of tiny RNAs with probable regulatory roles in Caenorhabditis elegans," Science. 294(5543):858-862.
Lee et al. (2001) "An extensive class of small RNAs in Caenorhabditis elegans," Science. 294(5543):862-864.
Lee et al. (2002) "Expression of small interfering RNAs targeted against HIV-1 rev transcripts in human cells," Nat. Biotechnol. 20:500-505.
Lee et al., "Recent Developments in Nanoparticle-Based siRNA Delivery for Cancer Therapy", BioMed Research International, vol. Article ID 782041, 10 pages, doi:10.1155/2013/782041, (2013).
Lewis et al., "Efficient delivery of siRNA for inhibition of gene expression in postnatal mice", Nat Genet., 32(1):107-108, doi: 10.1038/ng944, (Jul. 29, 2002).
Lim et al. (2003) "The microRNAs of Caenorhabditis elegans," Genes Dev. 17(8):991-1008.
Lim et al. (2003) "Vertebrate microRNA genes," Science. 299(5612):1540.
Liu et al., "Hydrodynamics-based transfection in animals by systemic administration of plasmid DNA", Gene, Ther. 6, 1258-1266, (1999).
Mccaffrey et al. (2002) "RNA interference in adult mice," Nature. 418(6893):38-39.
Mcmanus et al. (2002) "Gene silencing using micro-RNA designed hairpins," RNA. 8:842-850.
Miyagishi et al. (2002) "U6 promoter-driven siRNAs with four uridine 3' overhangs efficiently suppress targeted gene expression in mammalian cells," Nat. Biotechnol. 20:497-500.
Nielsen et al. (2001) "Sequence-selective recognition of DNA by strand displacement with a thymine-substituted polyamide," Science. 254:1497-1500.
Paddison et al. (2002) "Short hairpin RNAs (shRNAs) induce sequence-specific silencing in mammalian cells," Gene Dev. 16:948-958.
Pasquinelli et al. (2000) "Conservation of the sequence and temporal expression of let-7 heterochronic regulatory RNA," Nature. 408(6808):86-89.

(56) References Cited

OTHER PUBLICATIONS

Paul et al. (2002) "Effective expression of small interfering RNA in human cells," Nature Biotechnol. 20:505-508.
Petersen et al. (2003) "LNA: a versatile tool for therapeutics and genomics," Trends Biotechnol 21:74-81.
PUTNAM (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schwab et al. (1994) "An approach for new anticancer drugs: oncogene-targeted antisense DNA," Ann. Oncol. 5(Suppl 4):55-58.
Stein (2001) "Inhibition of Vesivirus infections in mammalian tissue culture with antisense morpholino oligomers," Antisense Nucleic Acid Drug Dev. 11(5):317-25.
Stein et al., "Systemic and Central Nervous System Correction of Lysosomal Storage in Mucopolysaccharidosis Type VII Mice", J Virol, 73:3424-3429, (1999).
Sui et al. (2002) "A DNA vector-based RNAi technology to suppress gene expression in mammalian cells," Proc Natl Acad Sci USA. 99:5515-5520.
Tuschl (2002) "Expanding small RNA interference," Nat. Biotechnol. 20(5):446-448.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Wang et al., "Nanoparticle-based delivery system for application of siRNA in vivo," Current Drug Metabolism, vol. 11, No. 2, pp. 182-196, 2010.
Xia et al. (2002) "siRNA-mediated gene silencing in vitro and in vivo," Nature Biotechnol. 20(10):1006-1010.
Yu et al. (2002) "RNA interference by expression of short-interfering RNAs and hairpin RNAs in mammalian cells," Proc Natl Acad Sci USA. 99:6047-6052.
Yuan et al., "Recent advances of siRNA delivery by nanoparticles," Expert Opinion on Drug Delivery, vol. 8, No. 4, pp. 521-536, 2011.
Zeng et al. (2002) "Both natural and designed micro RNAs can inhibit the expression of cognate mRNAs when expressed in human cells," Mol. Cell. 9(6):1327-1333.
Zeng et al. (2003) "Sequence requirements for micro RNA processing and function in human cells," RNA. 9(1):112-123.
Alterman et al., "A divalent siRNA chemical scaffold for potent and sustained modulation of gene expression throughout the central nervous system", Nature Biotechnology, Aug. 2, 2019, 37(8): 884-894.
Fernandez et al., "The Role of APOE4 in Disrupting the Homeostatic Functions of Astrocytes and Microglia in Aging and Alzheimer's Disease", Frontiers In Aging Neuroscience, Feb. 11, 2019, 11(14):1-18.
Nih, "Sequence 31656 from Patent EP2213738", EMBL, Aug. 18, 2010, Database accession No. HD154940.
NIH, "Sequence 31666 from Patent EP2213738", EMBL, Aug. 18, 2010, Database accession No. HD154950.
NIH, "Sequence 96771 from Patent EP2850184", EMBL, Jul. 8, 2015, Database accession No. JD784903.
Supplementary European Search Report of European Patent Application No. 20772940.1, mailed Mar. 24, 2023.
Van Neil et al., "Apolipoprotein E Regulates Amyloid Formation within Endosomes of Pigment Cells", Cell Reports, Oct. 2015, 13(1): 43-51.
Jo et al., "Deep Learning in Alzheimer's Disease: Diagnostic Classification and Prognostic Prediction Using Neuroimaging Data", Front. Aging Neurosci., Aug. 19, 2019, Sec. Alzheimer's Disease and Related Dementias, vol. 11, pp. 1-14.

* cited by examiner

| Compounds | IC50 (nmol) |
|---|---|
| 1203 | 18.75 |
| 1196 | 287 |
| 1134 | 14.67 |
| 1129 | 174 |
| 1123 | 70.9 |
| 1041 | 311 |

Mouse primary astrocytes. 1 week timepoint. Evaluated with WES (ProteinSimple)

| Compound | IC50 (nmol) |
|---|---|
| 1156 | 124 |
| 1163 | 198 |

| ID | Targeting sequence (30 BP) | Antisense sequence (5'-3') | Sense sequence (5'-3') |
|---|---|---|---|
| **Mouse** | | | |
| 1134 | SEQ ID NO: 37<br>TGTCCTGCAACAACATCCATATCCAGCCAGG | SEQ ID NO: 10<br>UUGGAUAUGGAUGUUGUUGCAG | SEQ ID NO: 12<br>GCAACAACAUCCAUAUCCAA |
| | | | |
| 1203 | SEQ ID NO: 38<br>CCTTGCTTAATAAAGATTCTCCGAGCACATT | SEQ ID NO: 11<br>UCUCGGAGAAUCUUUAUUAAGC | SEQ ID NO: 13<br>UUAAUAAAGAUUCUCCGAGA |
| | | | |
| **Human** | | | |
| 1156 | SEQ ID NO: 39<br>GTTTAATAAAGATTCACCAAGTTTCACGCA | SEQ ID NO: 14<br>UAAACUUGGUGAAUCUUUAU | SEQ ID NO: 4<br>GAUUCACCAAGUUUA |
| | | | |
| 1163 | SEQ ID NO: 40<br>GTTTAATAAAGATTCACCAAGTTTCACGCAAA | SEQ ID NO: 15<br>UUUGCGUGAAACUUGGUGAA | SEQ ID NO: 5<br>CAAGUUUCACGCAAA |

*Fig. 3A*

HPLC conditions 5-80% B over 15min Buffer A 0.1M TEAA + 5% ACN. Buffer B 100% ACN 1. Capped triethylene glycol linker (TEG)

2. Di-Oligo

3. Vit-D Conjugate

LCMS conditions: 0-100% B in 7min, 0.6ml/min. Buffer A 25mM HFIP, 15mM DBA in 20% MeOH. Buffer B MeOH with 20% Buffer A.

Mono-Phosphoamidate linker Approach:

Where X ia an alkyl: $(C)_n$ or polyether: $(CH_2OCH_2)_n$ Polyethylene: $(-CH_2CH_2O-)_n$ etc. Or any block copolymer, peptide or poly peptide, or any mixture of thereof.
Where Y is spacer or divider, cleavable or not. Of similar compositions as above.
Where Z is a branch point moiety.

DHAg2

DHA

GalNAc

Cholesterol

Where X is (C)n or (CO)n or (COC)n or (CONH)n or mixture of therein
Where Y is (C)n or (CO)n or (COC)n or (CONH)n or mixture of therein or spacer or divider, cleavable or not
Where W is a bioactive conjugate (right)

Phosphodiester

Phosphorothioate Sp

Phosphorothioate Rp

Phosphorodithioate

Phosphorus-based design phosphorothioates[1]
phosphorodithioates[2]
methylphosphonates[3]
methylenephosphonates[4]
vinylphosphonates[5]
phosphonates[6]
phosphotriesters[7]
boranophosphates[8]
phosphoramidates[9]

Normal nuclease suceptible phosphodiester

Non-phosphorus-based design amides[10]
urea (X=NH) or carbamates (X=O)[11]
carbonates[12]
formacetals[13]
triazoles[14]

Phosphodiester

Phosphorothioate

Phosphoramidate

Boranophosphate

2', 5'-Phosphodiester

Amide-linked

Phosphonoacetate

Morpholino

Peptide Nucleic Acid

RNA, DNA, 2'-O-Me, 2'F-RNA, 2'F-ANA, 4'S-RNA

LNA, 4'S-FANA, MOE, 2'-O-Allyl, 2'-O-Ethylamine, CNEt-RNA

Tricyclo-DNA, CeNA, ANA, HNA

*Fig. 36*
Di-siRNA^NTC
Di-siRNA^ApoE
GalNAc^NTC
GalNAc^ApoE
ApoE Protein (% NTC control)
150
100
50
0
Hippocampus
Cortex
Liver

OLIGONUCLEOTIDES FOR TISSUE SPECIFIC ApoE MODULATION

CROSS-REFERENCE TO RELATED APPLICATIONS

This application claims the benefit of U.S. Provisional Application Ser. No. 62/819,189, filed Mar. 15, 2019; 62/864,797, filed Jun. 21, 2019, and 62/951,441, filed Dec. 20, 2019, the entire disclosure of each of which is hereby incorporated herein by reference.

STATEMENT REGARDING FEDERALLY SPONSORED RESEARCH OR DEVELOPMENT

This invention was made with government support under Grant No. NS104022 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 2, 2020, is named 701996_UM9-240_ST25.txt and is 9,799 bytes in size.

FIELD OF THE INVENTION

This disclosure relates to novel apolipoprotein E (ApoE) targeting sequences, novel branched oligonucleotides, and novel methods for treating and preventing neurodegeneration.

BACKGROUND

Patients with neurodegenerative diseases including Alzheimer's disease (AD) and Amyotrophic Lateral Sclerosis (ALS) have limited treatment options. Abnormalities in cholesterol transport are consistently linked to neurodegeneration and worsening clinical symptoms in AD and ALS, making it a pathway of particular interest as a target for gene therapies.

Apolipoprotein E (ApoE) facilitates cholesterol transport in the systemic circulation and in the central nervous system (CNS). In human plasma and CNS, total ApoE levels and specific ApoE isoforms (i.e. E2, E3, E4) are associated with the onset and progression of AD and ALS. In addition, total ApoE levels in CNS have been found to be predictive of neurodegeneration progression.

In mice, global reduction of ApoE reduces pathological features of neurodegeneration, suggesting that non-selective modulating ApoE may be one treatment approach for neurodegenerative diseases. It is possible that close-to complete modulation of ApoE is necessary to have a measurable effect on neurodegeneration, a distinctive feature of presented compounds. Thus, there is an urgent need in the art for agents capable of CNS-modulation of ApoE expression.

SUMMARY

The present disclosure provides oligonucleotide compounds that exhibit potent and efficacious silencing activity on ApoE expression. In certain embodiments, the oligonucleotides of the disclosure are capable of inhibition in tissues of the central nervous system (CNS).

In one aspect, the disclosure provides an RNA molecule, such as an RNA molecule comprising 15 to 50 bases in length (e.g., an RNA molecule comprising from 15 to 40 bases in length, such as 15, 16, 17, 18, 19, 20, 21, 23, 24, 25, 26, 27, 28, 29, 30, 31, 32, 33, 34, 35, 36, 37, 38, 39, or 40 bases in length), comprising a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, the RNA molecule comprises a region of complementarity which is substantially complementary to one or more of 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

In some embodiments, the RNA molecule comprises single stranded (ss) RNA or double stranded (ds) RNA.

In some embodiments, the RNA molecule comprises a dsRNA comprising a sense strand and an antisense strand, wherein the antisense strand comprises the region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, the RNA molecule comprises 15 to 25 base pairs in length.

In some embodiments, the region of complementarity is complementary to at least 10, 11, 12 or 13 contiguous nucleotides of 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2). For example, the region of complementarity may be complementary to a segment of from 10 to 30 contiguous nucleotides of GUUUAAUAAAGAUUCACCAAGUUUCACGCAAA (SEQ ID NO: 1) or UGGACCCUAGUUUAAUAAAGAUUCACCAAG (SEQ ID NO: 2) (e.g., a segment of 10, 11, 12, 13, 14, 15, 16, 17, 18, 19, 20, 21, 22, 23, 24, 25, 26, 27, 28, 29, or 30 contiguous nucleotides of GUUUAAUAAAGAUUCACCAAGUUUCACGCAAA (SEQ ID NO: 1) or UGGACCCUAGUUUAAUAAAGAUUCACCAAG (SEQ ID NO: 2)).

In some embodiments, the region of complementarity contains no more than 3 mismatches with 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, the region of complementarity is fully complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, the dsRNA is blunt-ended.

In some embodiments, the dsRNA comprises at least one single stranded nucleotide overhang.

In some embodiments, the dsRNA comprises a naturally occurring nucleotide.

In some embodiments, the dsRNA comprises at least one modified nucleotide.

In some embodiments, the modified nucleotide comprises a 2'-O-methyl modified nucleotide, a nucleotide comprising a 5'-phosphorothioate group, or a terminal nucleotide linked to a cholesteryl derivative or dodecanoic acid bisdecylamide group.

In some embodiments, the modified nucleotide comprises a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, morpholino nucleotide, a phosphoramidate, or a non-natural base comprising nucleotide.

In some embodiments, the dsRNA comprises at least one 2'-O-methyl modified nucleotide and at least one nucleotide comprising a 5' phosphorothioate group.

In some embodiments, the dsRNA is at least 75% chemically modified. In some embodiments, the dsRNA is at least 80% chemically modified. In some embodiments, the dsRNA is fully chemically modified.

In some embodiments, the dsRNA comprises a cholesterol moiety.

In some embodiments, the RNA molecule comprises a 5' end, a 3' end and has complementarity to a target, wherein: (1) the RNA molecule comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-2 to 1-7 from the 3' end, are connected to adjacent nucleotides via phosphorothioate linkages.

In some embodiments, the dsRNA has a 5' end, a 3' end and complementarity to a target, and comprising a first oligonucleotide and a second oligonucleotide, wherein: (1) the first oligonucleotide comprises a sequence substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In some embodiments, the RNA molecule comprises a 5' end, a 3' end and has complementarity to a target, wherein: (1) the RNA molecule comprises a region of three contiguous 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; (4) the nucleotides at positions 1-2 to 1-7 from the 3' end, are connected to adjacent nucleotides via phosphorothioate linkages; and (5) the nucleotides at positions 1-2 from the 5' end are connected to each other via phosphorothioate linkages.

In some embodiments, the dsRNA has a 5' end, a 3' end and complementarity to a target, and comprising a first oligonucleotide and a second oligonucleotide, wherein: (1) the first oligonucleotide comprises sequence substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2); (2) a portion of the first oligonucleotide is complementary to a portion of the second oligonucleotide (3) the second oligonucleotide comprises a region of three contiguous 2'-methoxy-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In some embodiments, the second oligonucleotide is linked to a hydrophobic molecule at the 3' end of the second oligonucleotide.

In some embodiments, the linkage between the second oligonucleotide and the hydrophobic molecule comprises polyethylene glycol or triethylene glycol.

In some embodiments, the nucleotides at positions 1 and 2 from the 3' end of second oligonucleotide are connected to adjacent nucleotides via phosphorothioate linkages.

In some embodiments, the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

In one aspect, the disclosure provides a pharmaceutical composition for inhibiting the expression of Apolipoprotein E (ApoE) gene in an organism, comprising the dsRNA recited above and a pharmaceutically acceptable carrier.

In some embodiments, the dsRNA inhibits the expression of said ApoE gene by at least 50%. In some embodiments, the dsRNA inhibits the expression of said ApoE gene by at least 90%.

In one aspect, the disclosure provides a method for inhibiting expression of ApoE gene in a cell, the method comprising: (a) introducing into the cell a double-stranded ribonucleic acid (dsRNA) as recited above; and (b) maintaining the cell produced in step (a) for a time sufficient to obtain degradation of the mRNA transcript of the ApoE gene, thereby inhibiting expression of the ApoE gene in the cell.

In one aspect, the disclosure provides a method of treating or managing a neurodegenerative disease comprising administering to a patient in need of such treatment or management a therapeutically effective amount of the dsRNA recited above.

In some embodiments, the dsRNA is administered to a brain of the patient. In some embodiments, the dsRNA is locally administered to the brain or spinal fluid, e.g., by intracerebroventricular (ICV) injection. In other embodiments, the dsRNA is administered intravenously and is capable of crossing the blood brain barrier (BBB) for delivery to the brain.

In some embodiments, administering the dsRNA causes a decrease in ApoE gene mRNA in a hippocampus. In some embodiments, administering the dsRNA causes a decrease in ApoE gene mRNA in a spinal cord.

In some embodiments, the dsRNA inhibits the expression of said ApoE gene by at least 50%.

In some embodiments, the dsRNA inhibits the expression of said ApoE gene by at least 90%.

In one aspect, the disclosure provides a vector for inhibiting the expression of ApoE gene in a cell, said vector comprising a regulatory sequence operably linked to a nucleotide sequence that encodes an RNA molecule substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2), wherein said RNA molecule comprises 10 to 35 bases in length, and wherein said RNA molecule, upon contact with a cell expressing said ApoE gene, inhibits the expression of said ApoE gene by at least 50%.

In some embodiments, the RNA molecule inhibits the expression of said ApoE gene by at least 90%.

In some embodiments, the RNA molecule comprises ssRNA or dsRNA.

In some embodiments, the dsRNA comprises a sense strand and an antisense strand, wherein the antisense strand comprises the region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In one aspect, the disclosure provides a cell comprising the vector recited above.

In one aspect, the disclosure provides an RNA molecule comprising 15 to 35 bases in length, comprising a region of complementarity which is substantially complementary 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2), wherein the RNA molecule targets an open reading frame (ORF) or 3' untranslated region (UTR) of ApoE gene mRNA.

In some embodiments, the RNA molecule comprises ssRNA or dsRNA.

In some embodiments, the dsRNA comprises a sense strand and an antisense strand, wherein the antisense strand comprises the region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In one aspect, the disclosure provides a branched (e.g., di-branched) RNA compound comprising two or more RNA molecules that each comprise 15 to 35 bases in length, the RNA compound further comprising a region of complementarity which is substantially complementary to ApoE mRNA, wherein the two RNA molecules are covalently connected to one another (e.g., by one or more moieties independently selected from a linker, a spacer and a branching point).

In some embodiments, the RNA molecule comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, the RNA molecule comprises a region of complementarity which is substantially complementary to one or more of 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

In some embodiments, the RNA molecule comprises ssRNA or dsRNA.

In some embodiments, the RNA molecule comprises an antisense molecule or a GAPMER molecule.

In some embodiments, the antisense molecule comprises an antisense oligonucleotide.

In some embodiments, the antisense molecule enhances degradation of the region of complementarity.

In some embodiments, the degradation comprises nuclease degradation.

In some embodiments, the nuclease degradation is mediated by RNase H.

In one aspect, there is provided a branched oligonucleotide compound comprising two or more nucleic acids, such as two or more nucleic acids that each comprise from 15 to 40 bases in length, wherein:

each nucleic acid independently comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2), and the two or more nucleic acids are connected to one another by one or more moieties comprising a linker, a spacer or a branching point.

In some embodiments, each nucleic acid independently comprises a region of complementarity which is substantially complementary to one or more of 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

In some embodiments, each nucleic acid comprises 15 to 25 base pairs in length.

In some embodiments, each nucleic acid comprises single stranded (ss) RNA or double stranded (ds) RNA.

In some embodiments, each nucleic acid comprises a dsRNA comprising a sense strand and an antisense strand, wherein each antisense strand independently comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, each region of complementarity is independently complementary to at least 10, 11, 12 or 13 contiguous nucleotides of 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, each region of complementarity independently contains no more than 3 mismatches with 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, each region of complementarity is fully complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, each dsRNA independently comprises at least one modified nucleotide.

In some embodiments, the modified nucleotide comprises a 2'-O-methyl modified nucleotide, a nucleotide comprising a 5'-phosphorothioate group, or a terminal nucleotide linked to a cholesteryl derivative or dodecanoic acid bisdecylamide group.

In some embodiments, the modified nucleotide comprises a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In some embodiments, each of the two or more nucleic acids is an RNA molecule comprising a 5' end, a 3' end and has complementarity to a target, wherein:

(1) the RNA molecule comprises alternating 2'-methoxy-ribonucleotides and 2'-fluoro-ribonucleotides;
(2) the nucleotides at positions 2 and 14 from the 5' end are not 2'-methoxy-ribonucleotides;
(3) the nucleotides are connected via phosphodiester or phosphorothioate linkages; and
(4) the nucleotides at positions 1-2 to 1-7 from the 3' end, are connected to adjacent nucleotides via phosphorothioate linkages.

In some embodiments, each nucleic acid is a dsRNA having a 5' end, a 3' end and complementarity to a target, and comprising a first oligonucleotide and a second oligonucleotide, wherein:

(1) the first oligonucleotide comprises a sequence substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2);

(2) a portion of the first oligonucleotide is complementary to a portion of the second oligonucleotide;

(3) the second oligonucleotide comprises alternating 2'-methoxy-ribonucleotides and 2'-fluoro-ribonucleotides;

(4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In some embodiments, each of the two or more nucleic acids comprise an RNA molecule, wherein the RNA molecule comprises a 5' end, a 3' end and has complementarity to a target, wherein:

(1) the RNA molecule comprises a region of three contiguous 2'-fluoro-ribonucleotides;

(2) the nucleotides at positions 2 and 14 from the 5' end are not 2'-methoxy-ribonucleotides;

(3) the nucleotides are connected via phosphodiester or phosphorothioate linkages; (4) the nucleotides at positions 1-2 to 1-7 from the 3' end, are connected to adjacent nucleotides via phosphorothioate linkages; and (5) the nucleotides at positions 1-2 from the 5' end are connected to each other via phosphorothioate linkages.

In one aspect, the disclosure provides a compound of formula (I):

$$L—(N)_n \quad (I)$$

wherein

L comprises an ethylene glycol chain, an alkyl chain, a peptide, RNA, DNA, a phosphate, a phosphonate, a phosphoramidate, an ester, an amide, a triazole, or combinations thereof, wherein formula (I) optionally further comprises one or more branch point B, and one or more spacer S, wherein B is independently for each occurrence a polyvalent organic species or derivative thereof;

S comprises independently for each occurrence an ethylene glycol chain, an alkyl chain, a peptide, RNA, DNA, a phosphate, a phosphonate, a phosphoramidate, an ester, an amide, a triazole, or combinations thereof;

N comprises a double stranded nucleic acid, such as a double stranded nucleic acid comprising from 15 to 35 bases in length (e.g., 15, 16, 17, 18, 19, 20, 21, 22, 23, 24, 25, 26, 27, 28, 29, 30, 31, 32, 33, 34, or 35 bases in length), wherein the double stranded nucleic acid comprises a sense strand and an antisense strand, wherein the antisense strand comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2), the sense strand and antisense strand each independently comprise one or more chemical modifications; and n is 2, 3, 4, 5, 6, 7 or 8.

In some embodiments, the compound has a structure selected from formulas (I-1)-(I-9):

(I-1)

N—L—N (I-2)

N—S—L—S—N (I-3)

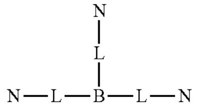

(I-4)

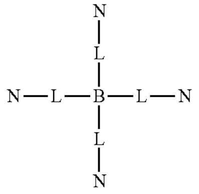

(I-5)

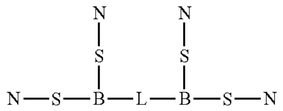

(I-6)

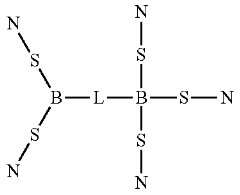

(I-7)

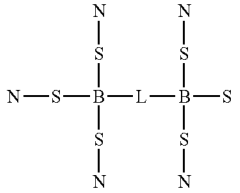

(I-8)

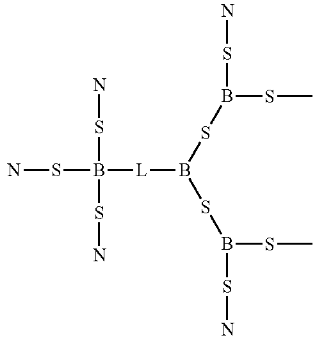

-continued
(I-9)
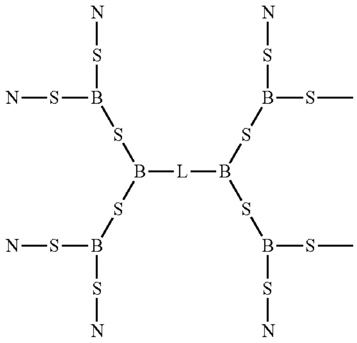
In an embodiment the antisense strand comprises a 5' terminal group R selected from the group consisting of:
$R^1$
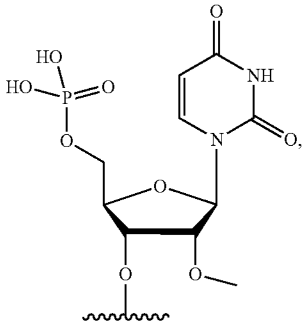
$R^2$
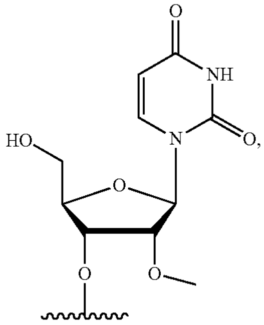
$R^3$
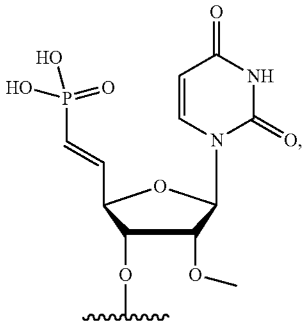
-continued
$R^4$
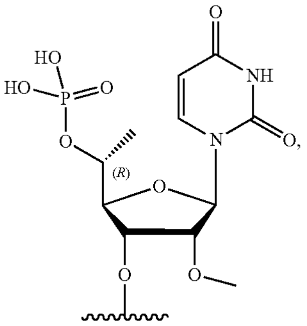
$R^5$
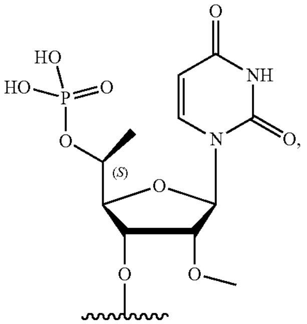
$R^6$
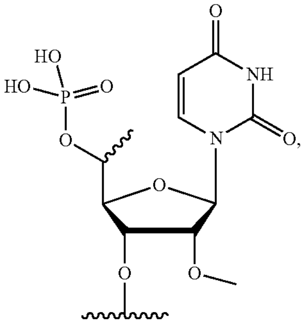
$R^7$
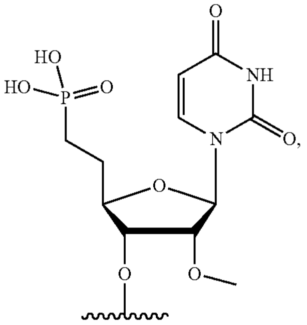
and -continued $R^8$

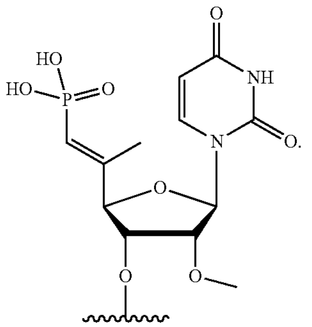

In some embodiments, the compound has the structure of formula (II):

(II)

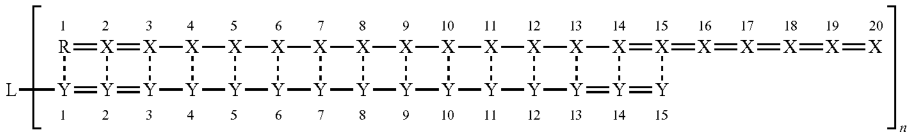

wherein

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

— represents a phosphodiester internucleoside linkage;

= represents a phosphorothioate internucleoside linkage; and

--- represents, individually for each occurrence, a base-pairing interaction or a mismatch.

In some embodiments, the compound has the structure of formula (III):

(III)

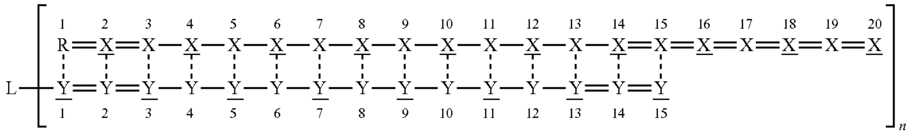

wherein

X̲, for each occurrence, independently, is a nucleotide comprising a 2'-deoxy-2'-fluoro modification;

X, for each occurrence, independently, is a nucleotide comprising a 2'-O-methyl modification;

Y̲, for each occurrence, independently, is a nucleotide comprising a 2'-deoxy-2'-fluoro modification; and Y, for each occurrence, independently, is a nucleotide comprising a 2'-O-methyl modification.

In some embodiments, the compound has the structure of formula (IV):

(IV)

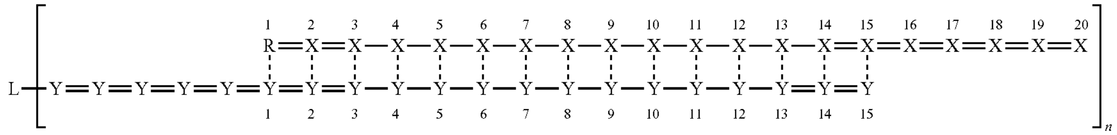

wherein

X, for each occurrence, independently, is selected from adenosine, guanosine, uridine, cytidine, and chemically-modified derivatives thereof;

Y, for each occurrence, independently, is selected from adenosine, guanosine, uridine, cytidine, and chemically-modified derivatives thereof;

— represents a phosphodiester internucleoside linkage;

= represents a phosphorothioate internucleoside linkage; and

--- represents, individually for each occurrence, a base-pairing interaction or a mismatch.

In some embodiments, the compound has a structure of formula (V):

(V)

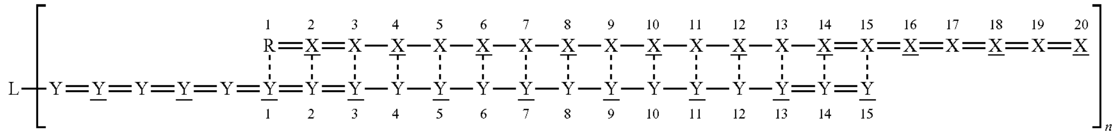

wherein

X̲, for each occurrence, independently, is a nucleotide comprising a 2'-deoxy-2'-fluoro modification;

X, for each occurrence, independently, is a nucleotide comprising a 2'-O-methyl modification;

Y̲, for each occurrence, independently, is a nucleotide comprising a 2'-deoxy-2'-fluoro modification; and Y, for each occurrence, independently, is a nucleotide comprising a 2'-O-methyl modification.

In some embodiments, moiety L is of structure L1:

(L1)

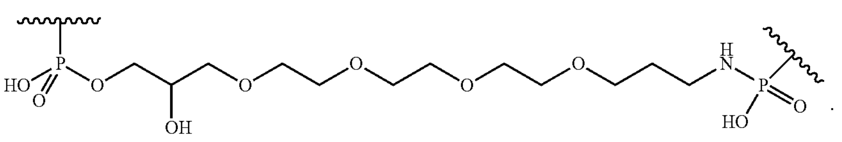

In some embodiments, when L is of structure L1, R is R3 and n is 2.

In some embodiments, L is of structure L2:

(L2)

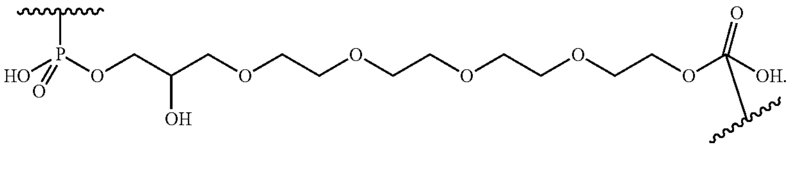

In some embodiments, when L is of structure L2, R is R3 and n is 2.

In one aspect, the disclosure provides a delivery system for therapeutic nucleic acids having the structure of Formula (VI):

$$L—(cNA)_n \quad (VI)$$

wherein

L comprises an ethylene glycol chain, an alkyl chain, a peptide, RNA, DNA, a phosphate, a phosphonate, a phosphoramidate, an ester, an amide, a triazole, or combinations thereof, wherein formula (VI) optionally further comprises one or more branch point B, and one or more spacer S, wherein B is independently for each occurrence a polyvalent organic species or derivative thereof, S comprises independently for each occurrence an ethylene glycol chain, an alkyl chain, a peptide, RNA, DNA, a phosphate, a phosphonate, a phosphoramidate, an ester, an amide, a triazole, or combinations thereof;

each cNA, independently, is a carrier nucleic acid comprising one or more chemical modifications;

each cNA, independently, comprises at least 15 contiguous nucleotides of 5' GUUUAAUAAAGAUUCACCAAGUUUCACGCAAA 3' (SEQ ID NO: 1) or 5'

UGGACCCUAGUUUAAUAAAGAUUCACCAAG 3' (SEQ ID NO: 2); and n is 2, 3, 4, 5, 6, 7 or 8.

In some embodiments, each cNA, independently, comprises from 15 to 25 contiguous nucleotides of 5' GUUUAAUAAAGAUUCACCAAGUUUCACGCAAA 3' (SEQ ID NO: 1) or 5' UGGACCC-UAGUUUAAUAAAGAUUCACCAAG 3' (SEQ ID NO: 2) (e.g., 15, 16, 17, 18, 19, 20, 21, 22, 23, 24, or 25 contiguous nucleotides).

In some embodiments, each cNA, independently, comprises from 15 to 21 contiguous nucleotides of 5' GUUUAAUAAAGAUUCACCAAGUUUCACGCAAA 3' (SEQ ID NO: 1) or 5' UGGACCC-UAGUUUAAUAAAGAUUCACCAAG 3' (SEQ ID NO: 2) (e.g., 15, 16, 17, 18, 19, 20, or 21 contiguous nucleotides).

In some embodiments, each cNA comprises 15 contiguous nucleotides of 5' GUUUAAUAAAGAUUCAC-CAAGUUUCACGCAAA 3' (SEQ ID NO: 1) or 5' UGGACCCUAGUUUAAUAAAGAUUCACCAAG 3' (SEQ ID NO: 2). In some embodiments, each can comprises 16 contiguous nucleotides of 5' GUUUAAUAAAGAUU-CACCAAGUUUCACGCAAA 3' (SEQ ID NO: 1) or 5' UGGACCCUAGUUUAAUAAAGAUUCACCAAG 3' (SEQ ID NO: 2).

In some embodiments, the delivery system has a structure selected from formulas (VI-1)-(VI-9):

(VI-1)

ANc—L—cNA (VI-2)

ANc—S—L—S—cNA (VI-3)

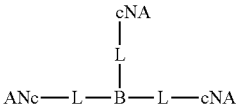

(VI-4)

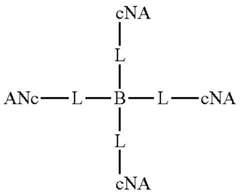

(VI-5)

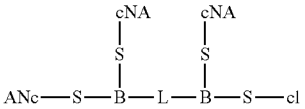

(VI-6)

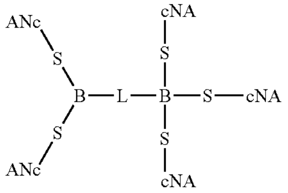

(VI-7)

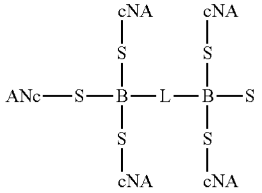

-continued (VI-8)

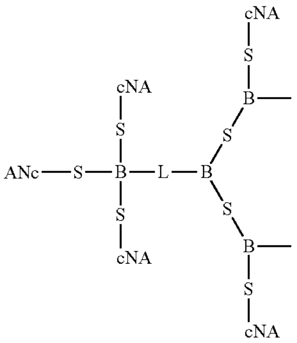

(VI-9)

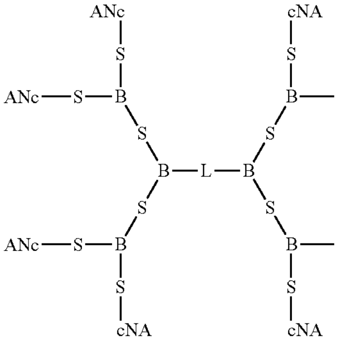

In some embodiments, each cNA independently, comprises chemically-modified nucleotides.

In some embodiments, the delivery system further comprises n therapeutic nucleic acids (NA), wherein each NA is hybridized to at least one cNA.

In some embodiments, each NA, independently, comprises at least 16 contiguous nucleotides. In some embodiments, each NA independently comprises from 16 to 30 contiguous nucleotides (e.g., 16, 17, 18, 19, 20, 21, 22, 23, 24, 25, 26, 27, 28, 29, or 30 contiguous nucleotides). In some embodiments, each NA independently comprises from 18 to 24 contiguous nucleotides (e.g., 18, 19, 20, 21, 22, 23, or 24 contiguous nucleotides).

In some embodiments, each NA, independently, comprises 16-21 contiguous nucleotides.

In some embodiments, each NA comprises 20 contiguous nucleotides. In some embodiments, each NA comprises 21 contiguous nucleotides.

In some embodiments, each cNA comprises 15 contiguous nucleotides of 5' GUUUAAUAAAGAUUCAC-CAAGUUUCACGCAAA 3' (SEQ ID NO: 1) or 5' UGGACCCUAGUUUAAUAAAGAUUCACCAAG 3' (SEQ ID NO: 2) and each NA comprises 20 contiguous nucleotides.

In some embodiments, each cNA comprises 16 contiguous nucleotides of 5' GUUUAAUAAAGAUUCAC-CAAGUUUCACGCAAA 3' (SEQ ID NO: 1) or 5' UGGACCCUAGUUUAAUAAAGAUUCACCAAG 3' (SEQ ID NO: 2) and each NA comprises 21 contiguous nucleotides.

In some embodiments, each NA comprises an unpaired overhang of at least 2 nucleotides. The nucleotides of the overhang may be connected via phosphorothioate linkages.

In some embodiments, each NA, independently, is selected from the group consisting of: DNA, siRNAs, antagomiRs, miRNAs, gapmers, mixmers, and guide RNAs.

In one aspect, the disclosure provides a pharmaceutical composition for inhibiting the expression of Apolipoprotein E (ApoE) gene in an organism, comprising one of the above compounds or systems, and a pharmaceutically acceptable carrier.

In some embodiments, the compound or system inhibits the expression of the ApoE gene by at least 50%.

In some embodiments, the compound or system inhibits the expression of the ApoE gene by at least 90%.

In one aspect, the disclosure provides a method for inhibiting expression of ApoE gene in a cell, the method comprising:

(a) introducing into the cell one of the above compounds or systems; and (b) maintaining the cell produced in step (a) for a time sufficient to obtain degradation of the mRNA transcript of the ApoE gene, thereby inhibiting expression of the ApoE gene in the cell.

In one aspect, the disclosure provides a method of treating or managing a neurodegenerative disease comprising administering to a patient in need of such treatment or management a therapeutically effective amount of one of the above compounds or systems.

In some embodiments, the compound or system is administered to the brain of the patient.

In some embodiments, the sRNA is administered to a brain of the patient. In some embodiments, the dsRNA is locally administered to the brain or spinal fluid, e.g., by intracerebroventricular (ICV) injection. In other embodiments, the dsRNA is administered intravenously and is capable of crossing the blood brain barrier (BBB) for delivery to the brain.

In some embodiments, administering the compound or system causes a decrease in ApoE gene mRNA in the hippocampus.

In some embodiments, administering the compound or system causes a decrease in ApoE gene mRNA in the spinal cord.

In some embodiments, the dsRNA inhibits the expression of the ApoE gene by at least 50%.

In some embodiments, the dsRNA inhibits the expression of the ApoE gene by at least 90%.

In one aspect, there is provided a branched oligonucleotide compound comprising two or more nucleic acids, such as two or more nucleic acids that each comprise 15 to 40 bases in length (e.g., 15, 16, 17, 18, 19, 20, 21, 22, 23, 24, 25, 26, 27, 28, 29, 30, 31, 32, 33, 34, 35, 36, 37, 38, 39, or 40 bases in length), wherein each nucleic acid comprises a region of complementarity which is substantially complementary to ApoE mRNA, wherein the two nucleic acids are covalently connected to one another (e.g., by one or more moieties comprising a linker, a spacer or a branching point).

In some embodiments, each nucleic acid independently comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2).

In some embodiments, each nucleic acid independently comprises a region of complementarity which is substantially complementary to one or more of 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

In some embodiments, each of the nucleic acids comprises independently single stranded (ss) RNA or double stranded (ds) RNA.

In some embodiments, each of the nucleic acids comprises independently an antisense molecule or a GAPMER molecule.

In one aspect, there is provided a method of treating or managing an amyloid-related disease, the method comprising administering to a patient diagnosed as having or at risk for developing the disease a therapeutically effective amount of one of the above compounds or systems.

In some embodiments, the disease is selected from the group consisting of Alzheimer's disease, cerebral amyloid angiopathy, mild cognitive impairment, moderate cognitive impairment, and combinations thereof.

In some embodiments, the compound or system is administered to the brain of the patient, for example by intracerebroventricular injection.

In a non-limiting embodiment, the administration of the compound or system inhibits, delays, prevents, or reduces cognitive decline. In a further non-limiting embodiment, the administration of the compound or system inhibits, delays, prevents, or reduces beta-amyloid plaque formation. In an exemplary embodiment, the administration of the compound or system inhibits, delays, prevents, or reduces neurodegeneration.

In a further aspect, there is provided a method of treating or managing Alzheimer's disease, the method comprising administering to a patient diagnosed as having or at risk for developing the disease a therapeutically effective amount of a branched oligonucleotide compound comprising two or more nucleic acids, such as two or more nucleic acids that each comprise 15 to 40 bases in length (e.g., 15, 16, 17, 18, 19, 20, 21, 22, 23, 24, 25, 26, 27, 28, 29, 30, 31, 32, 33, 34, 35, 36, 37, 38, 39, or 40 bases in length), wherein each nucleic acid comprises a region of complementarity which is substantially complementary to ApoE mRNA, wherein the two nucleic acids are covalently connected to one another (e.g., by one or more moieties comprise a linker, a spacer or a branching point).

In some embodiments, each nucleic acid of the branched oligonucleotide compound independently comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2). In a further embodiment, each nucleic acid of the branched oligonucleotide independently comprises a region of complementarity which is substantially complementary to one or more of 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

In some embodiments, each of the nucleic acids comprises single stranded (ss) RNA or double stranded (ds) RNA.

In a further embodiment, each of the nucleic acids comprises an antisense molecule or a GAPMER molecule.

In some embodiments, the branched oligonucleotide is administered to the brain of the patient, for example by intracerebroventricular injection.

In a non-limiting embodiment, the administration of the branched oligonucleotide inhibits, delays, prevents, or reduces cognitive decline. In a further non-limiting embodiment, the administration of the compound or system inhibits, delays, prevents, or reduces beta-amyloid plaque formation. In an exemplary embodiment, the administration of the branched oligonucleotide inhibits, delays, prevents, or reduces neurodegeneration.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A depicts a screen identifying hit sequences targeting ApoE in mouse primary astrocytes.

FIG. 1B depicts dose response curves of hit sequences from the primary screen in mouse primary astrocytes.

FIG. 1C depicts a dose response showing protein silencing in mouse primary astrocytes.

FIG. 2A depicts a screen identifying hit sequences targeting ApoE in HepG2 cells.

FIG. 2B depicts dose response curves of hit sequences from the primary screen in HepG2 cells.

FIGS. 3A-3B illustrate oligonucleotides targeting ApoE

FIG. 3A depicts targeting sequences in the mouse and human ApoE genes and oligonucleotides targeting such sequences (SEQ ID NOS 37, 10, 12, 38, 11, 13, 39, 14, 4, 40, 15, and 5, respectively, in order of appearance).

FIG. 3B illustrates example chemical modifications to the oligonucleotides.

FIG. 4A illustrates mRNA silencing in all regions of the brain 1-month post injection.

FIG. 4B illustrates protein silencing in all regions of the brain 1-month post injection.

FIG. 4C is a Western blot showing protein silencing throughout the brain.

FIG. 5A depicts a quantification of protein silencing in the hippocampus 1-month post injection.

FIG. 5B is a Western blot showing target protein silencing.

FIG. 6A is a quantification of protein silencing in the spinal cord 1-month post injection.

FIG. 6B is a Western blot showing target ApoE (37 kDa) protein silencing as compared to control vinculin (116 kDa).

FIG. 7A is a quantification of protein silencing in the liver 1-month post injection.

FIG. 7B is a Western blot (ProteinSimple) showing target ApoE (37 kDa) protein silencing as compared to control vinculin (116 kDa).

FIG. 8A is a Western blot showing ApoE protein silencing in the liver vs. control vinculin.

FIG. 8B is a Western blot showing no effect on the protein levels in the brain.

FIG. 8C is a quantification of protein silencing in the liver and brain.

FIG. 9A depicts a quantification of total serum cholesterol after silencing CNS ApoE.

FIG. 9B depicts a quantification of total serum cholesterol after silencing systemic ApoE and a quantification of cholesterol in LDL and HDL fractions after silencing systemic ApoE.

FIG. 10A illustrates protein silencing in the brain and liver after injection with CNS-siRNA$^{ApoE}$.

FIG. 10B illustrates silencing in the brain (none) and liver after injection with GalNAc-siRNA$^{ApoE}$.

FIG. 15A shows a Mono-Phosphoamidate linker approach and FIG. 15B shows a Di-Phosphate linker approach.

(FIG. 20B) asymmetrical branched oligonucleotides with 3' and 5' linkages to the linkers or spaces described previously. This can be applied the 3' and 5' ends of the sense strand or the antisense strands or a combination thereof; (FIG. 20C) branched oligonucleotides made up of three separate strands. The long dual sense strand can be synthesized with 3' phosphoramidites and 5' phosphoramidites to allow for 3'-3' adjacent or 5'-5' adjacent ends.

FIG. 35A: mRNA silencing 2-months post injection with Di-siRNA$^{ApoE}$. FIG. 35B: mRNA silencing 2-months post injection with GalNAc-siRNA$^{ApoE}$.

FIG. 36A: protein silencing 2-month post injection with Di-siRNA$^{ApoE}$. FIG. 36B: protein silencing 2-months post injection with GalNAc-siRNA$^{ApoE}$.

FIG. 39A: average number of cortex plaques per animal in Di-siRNA$^{APOE}$ treated mice compared to Di-siRNA$^{NTC}$ treated mice. FIG. 39B: average number of cortex plaques per animal in GalNAc-siRNA$^{ApoE}$ treated mice compared to GalNAc-siRNA$^{NTC}$ treated mice.

FIG. 40A: sex-specific analysis of Di-siRNA$^{NTC}$ and Di-siRNA$^{APoE}$ treated mice. FIG. 40B and FIG. 40C: number of plaques in each slice for each individual mouse.

FIG. 42A: quantification of protein silencing in the hippocampus and liver 1 month post injection. FIG. 42B: quantification of protein silencing in the spinal cord.

FIG. 44A depicts a primary screen identifying hit sequences targeting ApoE in HepG2 cells. FIG. 44B illustrates the effectiveness and potency of hit sequences from the primary screen in HepG2 cells. FIG. 44C depicts dose response curves of hit sequences from the primary screen in HepG2 cells.

DETAILED DESCRIPTION OF CERTAIN EXEMPLARY EMBODIMENTS

Figure 1A:
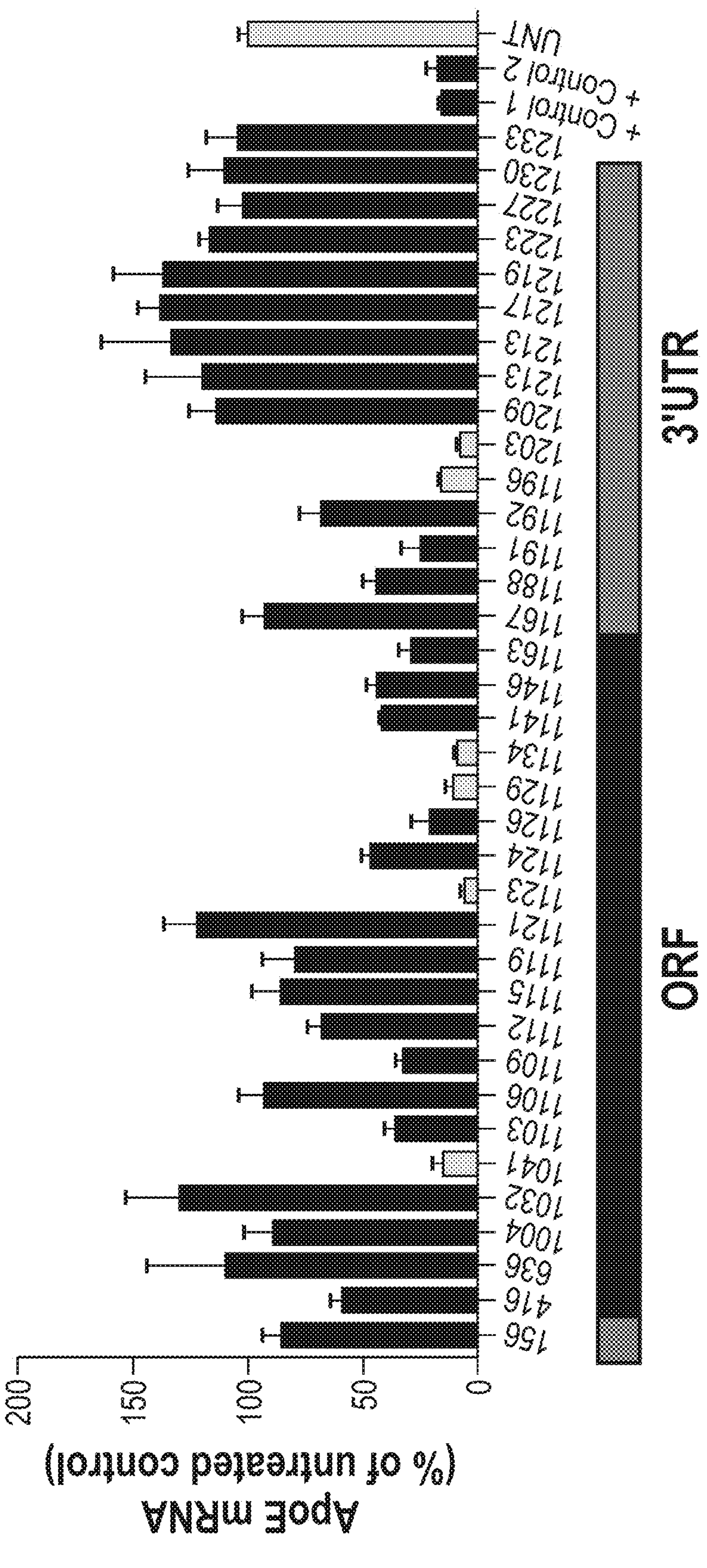
FIGS. 1A-1C illustrate the identification of novel targeting sequences showing silencing in both mRNA and protein based mouse cell models.

Novel ApoE target sequences are provided. Also provided are novel interfering RNA molecules, such as siRNAs, that target the novel ApoE target sequences of the invention.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of a consecutive glutamine residues linked to peptide bonds. In one embodiment the consecutive region includes at least 5 glutamine residues (SEQ ID NO: 7).

The term "expanded polyglutamine domain" or "expanded polyglutamine segment," as used herein, refers to a segment or domain of a protein that includes at least 35 consecutive glutamine residues linked by peptide bonds (SEQ ID NO: 8). Such expanded segments are found in subjects afflicted with a polyglutamine disorder, as described herein, whether or not the subject has shown to manifest symptoms.

The term "trinucleotide repeat" or "trinucleotide repeat region" as used herein, refers to a segment of a nucleic acid sequence) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE mental retardation, Friedreich's ataxia and myotonic dystrophy. Exemplary trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-μ, wherein T is an mRNA targeting moiety, L is a linking moiety, and μ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the invention are described in further detail in the following subsections.

I. Novel Target Sequences

In certain exemplary embodiments, the RNA silencing agents of the invention are capable of targeting an APOE mRNA target recited in Tables 1, 2, or 7. In certain exemplary embodiments, RNA silencing agents of the invention are capable of targeting 5' GUUUAAUAAAGAUUCACCAAGUUUCACGCAAA 3' (SEQ ID NO: 1). In certain exemplary embodiments, RNA silencing agents of the invention are capable of targeting one or more of the target sequences 5' GAUUCACCAAGUUUA 3' (SEQ ID NO: 4) and 5' CAAGUUUCACGCAAA 3' (SEQ ID NO: 5). In certain exemplary embodiments, RNA silencing agents of the invention are capable of targeting 5' UGGACCCUAGUUUAAUAAAGAUUCACCAAG 3' (SEQ ID NO: 2). In certain exemplary embodiments, RNA silencing agents of the invention are capable of targeting the target sequence 5' CCUAGUUUAAUAAAGAUUCA 3' (SEQ ID NO: 6).

Genomic sequence for each target sequence can be found in, for example, the publicly available database maintained by the NCBI.

II. siRNA Design

In some embodiments, siRNAs are designed as follows. First, a portion of the target gene (e.g., the ApoE gene), e.g., one or more of the target sequences set forth in Table 1, Table 2, or Table 7 is selected. Cleavage of mRNA at these sites should eliminate translation of corresponding protein. Sense strands were designed based on the target sequence. (See FIG. 3A). Preferably the portion (and corresponding sense strand) includes about 19 to 25 nucleotides, e.g., 19, 20, 21, 22, 23, 24 or 25 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably, the RNAi agents of the invention do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2-, 3-, 4-, 5-, 6- or 7-nucleotide overhangs are generated, i.e., the 3' end of the sense strand extends 1, 2, 3, 4, 5, 6 or 7 nucleotides further than the 5' end of the antisense strand and/or the 3' end of the antisense strand extends 1, 2, 3, 4, 5, 6 or 7 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the ApoE target sequences set forth at FIG. 3 is described in detail below. siRNAs can be designed according to the above exemplary teachings for any other target sequences found in the ApoE gene. Moreover, the technology is applicable to targeting any other target sequences, e.g., non-disease-causing target sequences.

To validate the effectiveness by which siRNAs destroy mRNAs (e.g., ApoE mRNA), the siRNA can be incubated with cDNA (e.g., ApoE cDNA) in a *Drosophila*-based in vitro mRNA expression system. Radiolabeled with $^{32}P$, newly synthesized mRNAs (e.g., ApoE mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

III. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., ApoE genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the gene encoding ApoE, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs as known in the art, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to poly alkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^{3}H$, $^{32}P$ or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-ApoE RNA Silencing Agents

In one embodiment, the present invention provides novel anti-ApoE RNA silencing agents (e.g., siRNA and shRNAs), methods of making said RNA silencing agents, and methods (e.g., research and/or therapeutic methods) for using said improved RNA silencing agents (or portions thereof) for RNA silencing of ApoE protein. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications), although consecutive 2'-fluoro modifications and consecutive 2'-methoxy modifications are also contemplated; and (5) single-stranded, fully phosphorothioated tails of 5-8 bases. The number of phosphorothioate modifications is varied from 6 to 17 total in different embodiments.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not purimidines are modified) in wide range of cell types (e.g., HeLa, neurons, hepatocytes, trophoblasts).

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the invention can be described in the following aspects and embodiments.

In a first aspect, provided herein is an oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides;

(2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide and a second oligonucleotide, wherein: (1) the first oligonucleotide is an oligonucleotide described herein (e.g., comprising one of the target sequences of FIG. 3A); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In a third aspect, provided herein is oligonucleotide having the structure:

X-A(-L-B-L-A)j(-S-B-S-A)r(-S-B)t-OR wherein: X is a 5' phosphate group; A, for each occurrence, independently is a 2'-methoxy-ribonucleotide; B, for each occurrence, independently is a 2'-fluoro-ribonucleotide; L, for each occurrence independently is a phosphodiester or phosphorothioate linker; S is a phosphorothioate linker; and R is selected from hydrogen and a capping group (e.g., an acyl such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein: (1) the first oligonucleotide is selected from the oligonucleotides of the third aspect; (2) a portion of the first oligonucleotide is complementary to a portion of the second oligonucleotide; and (3)

the second oligonucleotide has the structure:

C-L-B(-S-A-S-B)m'(-P-A-P-B)n'(-P-A-S-B)q'(-S-A)r'(-S-B)t'-OR wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-4 repeat units of ethyleneglycol, a phosphodiester, and a phosphorothioate; S is a phosphorothioate linker; P is a phosphodiester linker; R is selected from hydrogen and a capping group (e.g., an acyl such as acetyl); m' is 00r 1; n' is 4, 5 or 6; q' is 00r 1; r' is 00r 1; and t' is 00r 1.

a) Design of Anti-ApoE siRNA Molecules

An siRNA molecule of the invention is a duplex consisting of a sense strand and complementary antisense strand, the antisense strand having sufficient complementary to an ApoE mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Usually, siRNAs can be designed by using any method known in the art, for instance, by using the following protocol:

1. The siRNA should be specific for a target sequence, e.g., a target sequence set forth in FIG. 3A. In one embodiment, a target sequence is found in a wild-type ApoE allele. In another embodiment, a target sequence is found in both a mutant ApoE allele, and a wild-type ApoE allele. In another embodiment, a target sequence is found in a wild-type ApoE allele. The first strand should be complementary to the target sequence, and the other strand is substantially complementary to the first strand. (See FIG. 3 for exemplary sense and antisense strands.) Exemplary target sequences are selected from the 5' untranslated region (5'-UTR) of a target gene. Cleavage of mRNA at these sites should eliminate translation of corresponding ApoE protein. Target sequences from other regions of the ApoE gene are also suitable for targeting. A sense strand is designed based on the target sequence. Further, siRNAs with lower G/C content (35-55%) may be more active than those with G/C content higher than 55%. Thus, in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention, provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s)

with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6(log 10[Na+])+0.41(% G+C)−(600/N), where N is the number of bases in the hybrid, and [Na+] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant ApoE mRNA), the siRNA may be incubated with target cDNA (e.g., ApoE cDNA) in a *Drosophila*-based in vitro mRNA expression system. Radiolabeled with $^{32}P$, newly synthesized target mRNAs (e.g., ApoE mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-ApoE siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth at FIG. 3A, and an antisense strand comprising a sequence set forth at FIG. 3A.

Sites of siRNA-mRNA complementation are selected which result in optimal mRNA specificity and maximal mRNA cleavage.

b) siRNA-Like Molecules siRNA-like molecules of the invention have a sequence (i.e., have a strand having a sequence) that is “sufficiently complementary” to a target sequence of an ApoE mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central “bulge” (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the “bulge” is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an ApoE target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide “loop” in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second “stem” portions are connected by a portion having a sequence that has insufficient sequence complementarity to anneal or hybridize to other portions of the shRNA. This latter portion is referred to as a “loop” portion in the shRNA molecule. The shRNA molecules are processed to generate siRNAs. shRNAs can also include one or more bulges, i.e., extra nucleotides that create a small nucleotide “loop” in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the ApoE target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., ApoE mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-μ, wherein T is an mRNA targeting moiety, L is a linking moiety, and is an miRNA recruiting moiety. Any one or more moiety may be double stranded. Preferably, however, each moiety is single stranded.

Moieties within the tethers can be arranged or linked (in the 5' to 3' direction) as depicted in the formula T-L-μ (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: p-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-p-methyladenosine, 2'-O-methylthymidine, 2'-O-methylguanosine or 2'-O-methyluridine.

e) Gene Silencing Oligonucleotides

In certain exemplary embodiments, gene expression (i.e., ApoE gene expression) can be modulated using oligonucleotide-based compounds comprising two or more single stranded antisense oligonucleotides that are linked through their 5'-ends that allow the presence of two or more accessible 3'-ends to effectively inhibit or decrease ApoE gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula $HO—(CH_2)_o—CH(OH)—(CH_2)_p—OH$, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula $HO—(CH_2)m—C(O)NH—CH_2—CH(OH)—CH_2—NHC(O)—(CH_2)_m—OH$, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length.

Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

V. Modified Anti-ApoE RNA Silencing Agents

In certain aspects of the invention, an RNA silencing agent (or any portion thereof) of the invention as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the invention features RNA silencing agents that are at least 80% chemically modified. In a preferred embodiment of the present invention, the RNA silencing agents may be fully chemically modified, i.e., 100% of the nucleotides are chemically modified.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2-amino-cytidine, 2-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, bomeol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10,13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, bomeol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, $Eu^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-kB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNF D), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

VI. Branched Oligonucleotides

Figure 11:
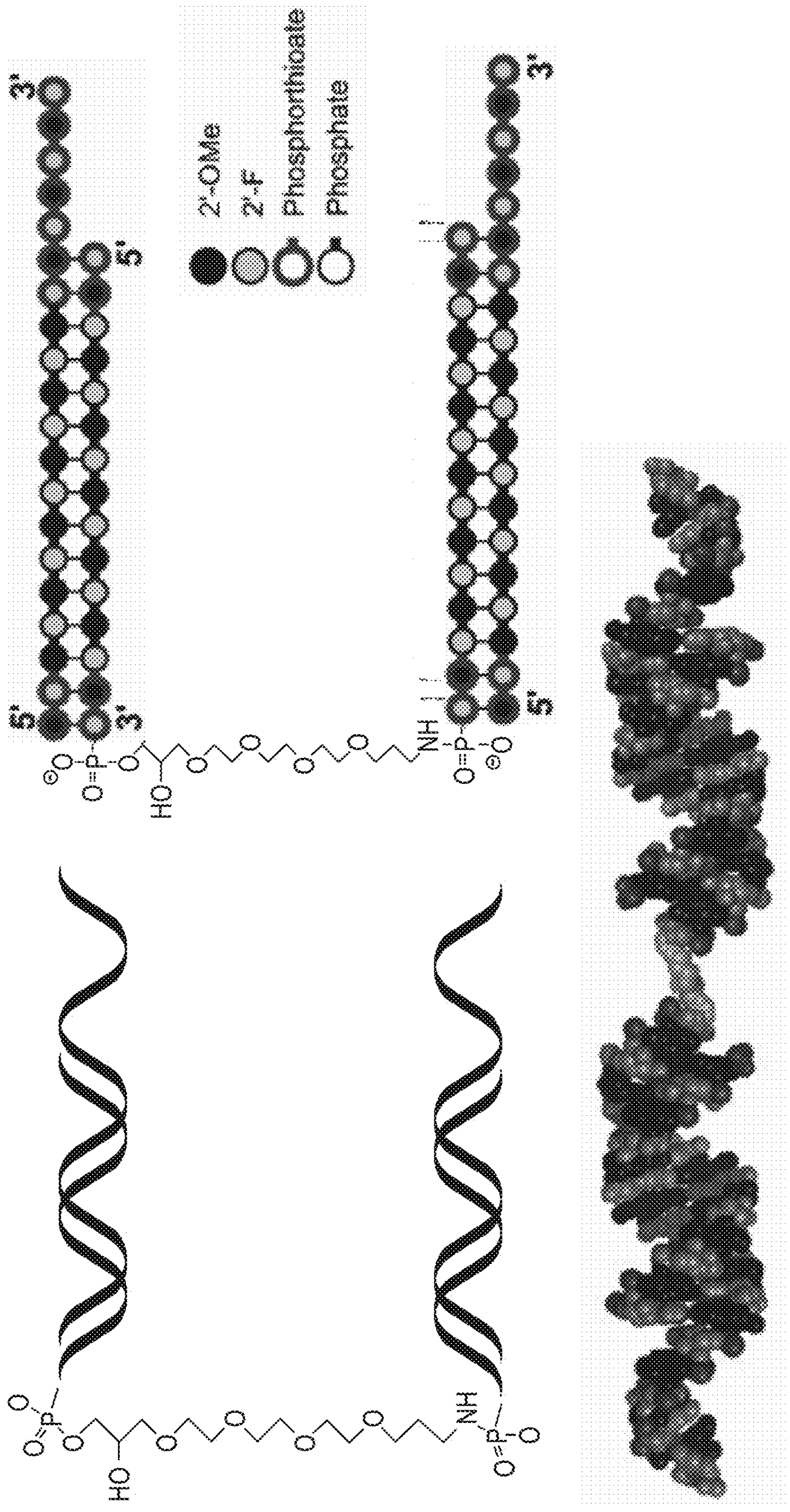
FIG. 11 shows the structure of Di-hsiRNAs. Black—2'-O-methyl, grey—2'-fluoro, red dash—phosphorothioate bond, linker—tetraethylene glycol. Di-hsiRNAs are two asymmetric siRNAs attached through the linker at the 3' ends of the sense strand. Hybridization to the longer antisense strand creates protruding single stranded fully phosphorothioated regions, essential for tissue distribution, cellular uptake and efficacy. The structures presented utilize teg linger of four monomers. The chemical identity of the linker can be modified without the impact on efficacy. It can be adjusted by length, chemical composition (fully carbon), saturation or the addition of chemical targeting ligands.

Two or more RNA silencing agents as disclosed supra, for example oligonucleotide constructs such as anti-ApoE siRNAs, may be connected to one another by one or more moieties independently selected from a linker, a spacer and a branching point, to form a branched oligonucleotide RNA silencing agent. FIG. 11 illustrates an example di-branched Di-siRNA scaffolding for delivering two siRNAs. In representative embodiments, the nucleic acids of the branched oligonucleotide each comprise an antisense strand (or portions thereof), wherein the antisense strand has sufficient complementarity to a heterozygous single nucleotide polymorphism to mediate an RNA-mediated silencing mechanism (e.g. RNAi). In other embodiments, there is provided a second type of branched oligonucleotides featuring nucleic acids that comprise a sense strand (or portions thereof) for silencing ApoE antisense transcripts, where the sense strand has sufficient complementarity to an antisense transcript to mediate an RNA-mediated silencing mechanism. In further embodiments, there is provided a third type of branched oligonucleotides including nucleic acids of both types, that is, a first oligonucleotide comprising an antisense strand (or portions thereof) and a second oligonucleotide comprising a sense strand (or portions thereof).

In exemplary embodiments, the branched oligonucleotides may have two to eight RNA silencing agents attached through a linker. The linker may be hydrophobic. In some embodiments, branched oligonucleotides of the present application have two to three oligonucleotides. In some embodiments, the oligonucleotides independently have substantial chemical stabilization (e.g., at least 40% of the constituent bases are chemically-modified). In an exemplary embodiment, the oligonucleotides have full chemical stabilization (i.e., all the constituent bases are chemically-modified). In some embodiments, branched oligonucleotides comprise one or more single-stranded phosphorothioated tails, each independently having two to twenty nucleotides. In a non-limiting embodiment, each single-stranded tail has eight to ten nucleotides.

In certain embodiments, branched oligonucleotides are characterized by three properties: (1) a branched structure, (2) full metabolic stabilization, and (3) the presence of a single-stranded tail comprising phosphorothioate linkers. In a specific embodiment, branched oligonucleotides have 2 or 3 branches. It is believed that the increased overall size of the branched structures promotes increased uptake. Also, without being bound by a particular theory of activity, multiple adjacent branches (e.g., 2 or 3) are believed to allow each branch to act cooperatively and thus dramatically enhance rates of internalization, trafficking and release.

Figure 17:
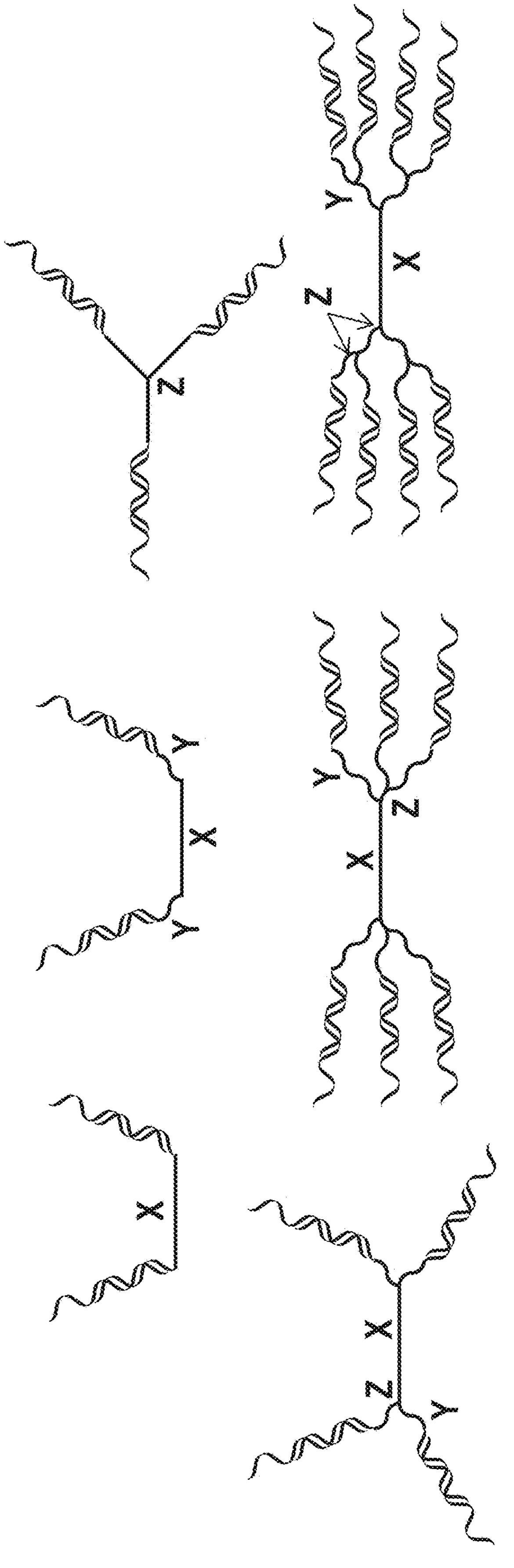
FIG. 17 shows oligonucleotide branching motifs. The double-helices represented oligonucleotides. The combination of different linkers, spacer and branching points allows generation of a wide diversity of branched hsiRNA structures.
Figure 18:
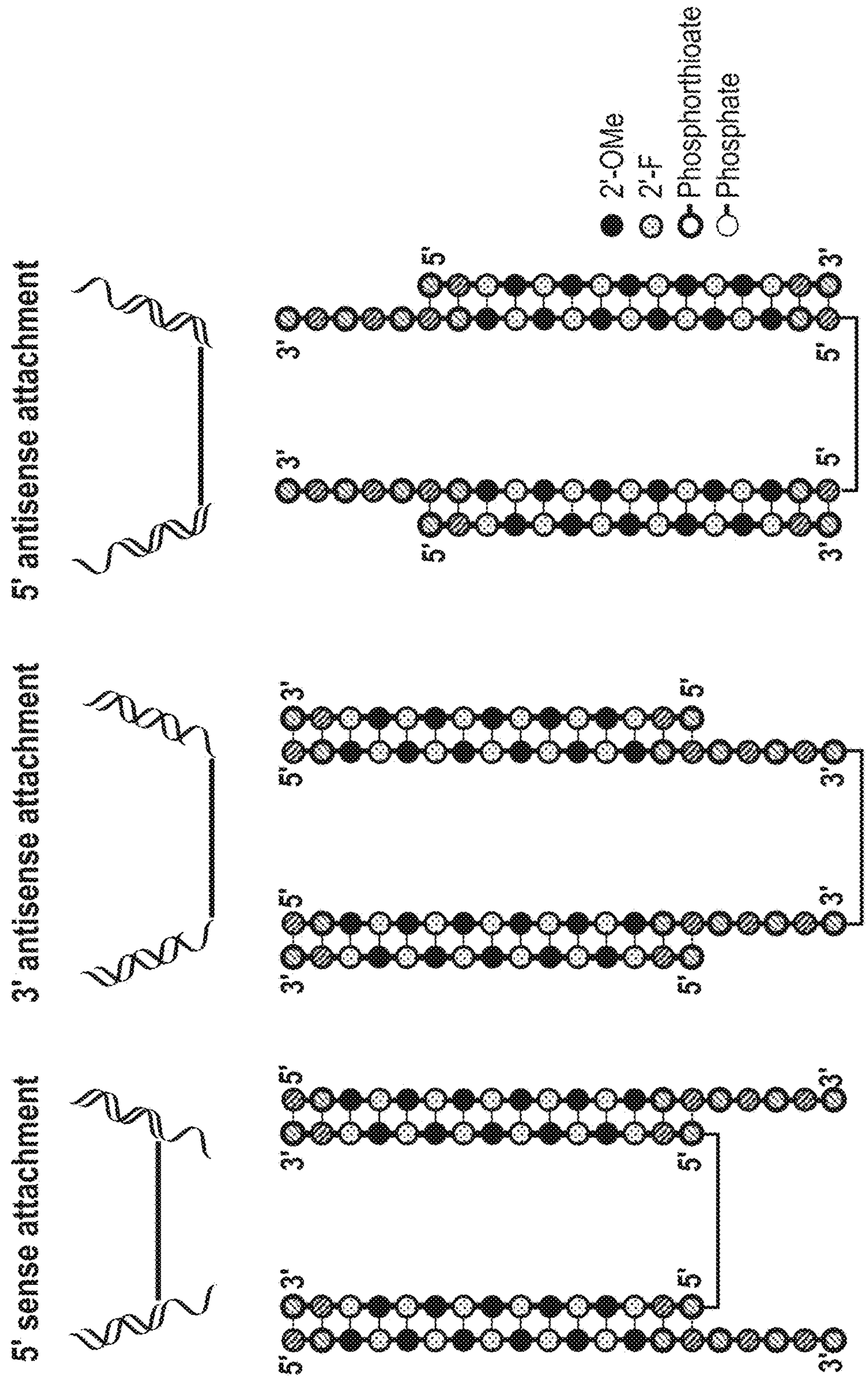
FIG. 18 shows structurally diverse branched oligonucleotides.
Figure 19:
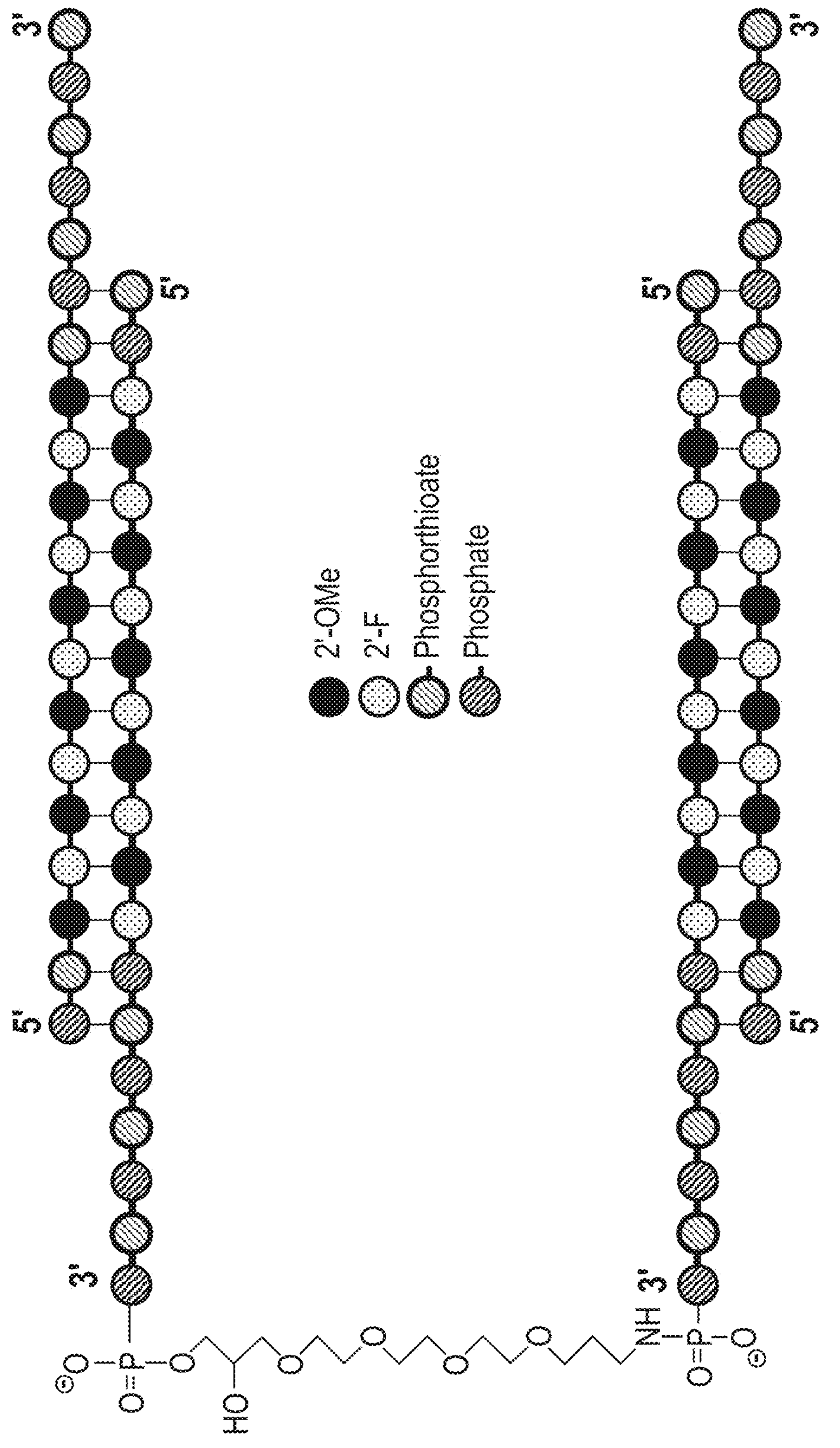
FIG. 19 shows an asymmetric compound of the invention having four single-stranded phosphorothioate regions.
Figure 20A:
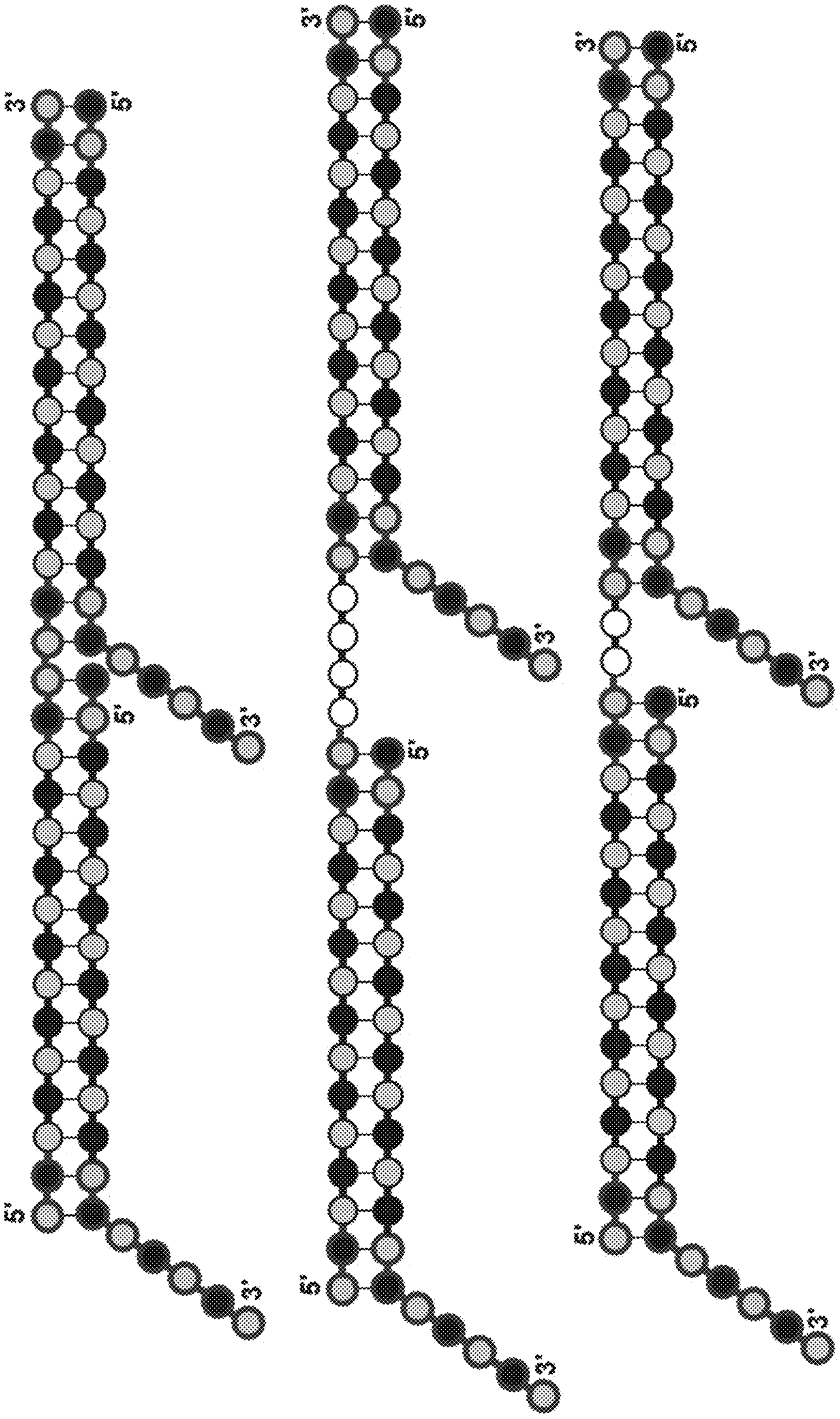
FIGS. 20A-20C shows branched oligonucleotides of the invention, (FIG. 20A) formed by annealing three oligonucleotides. The longer linking oligonucleotides may comprise a cleavable region in the form of unmodified RNA, DNA or UNA.
Figure 20B:
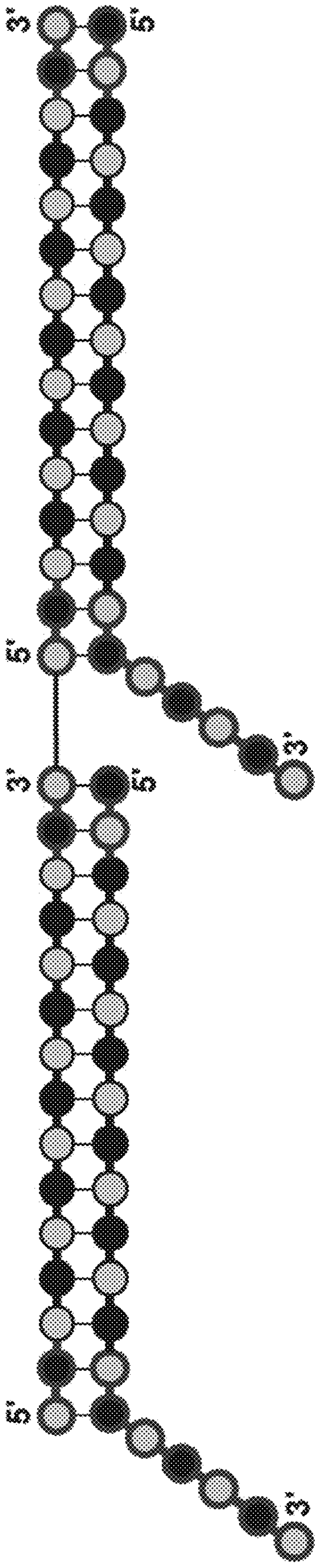
Figure 20C:
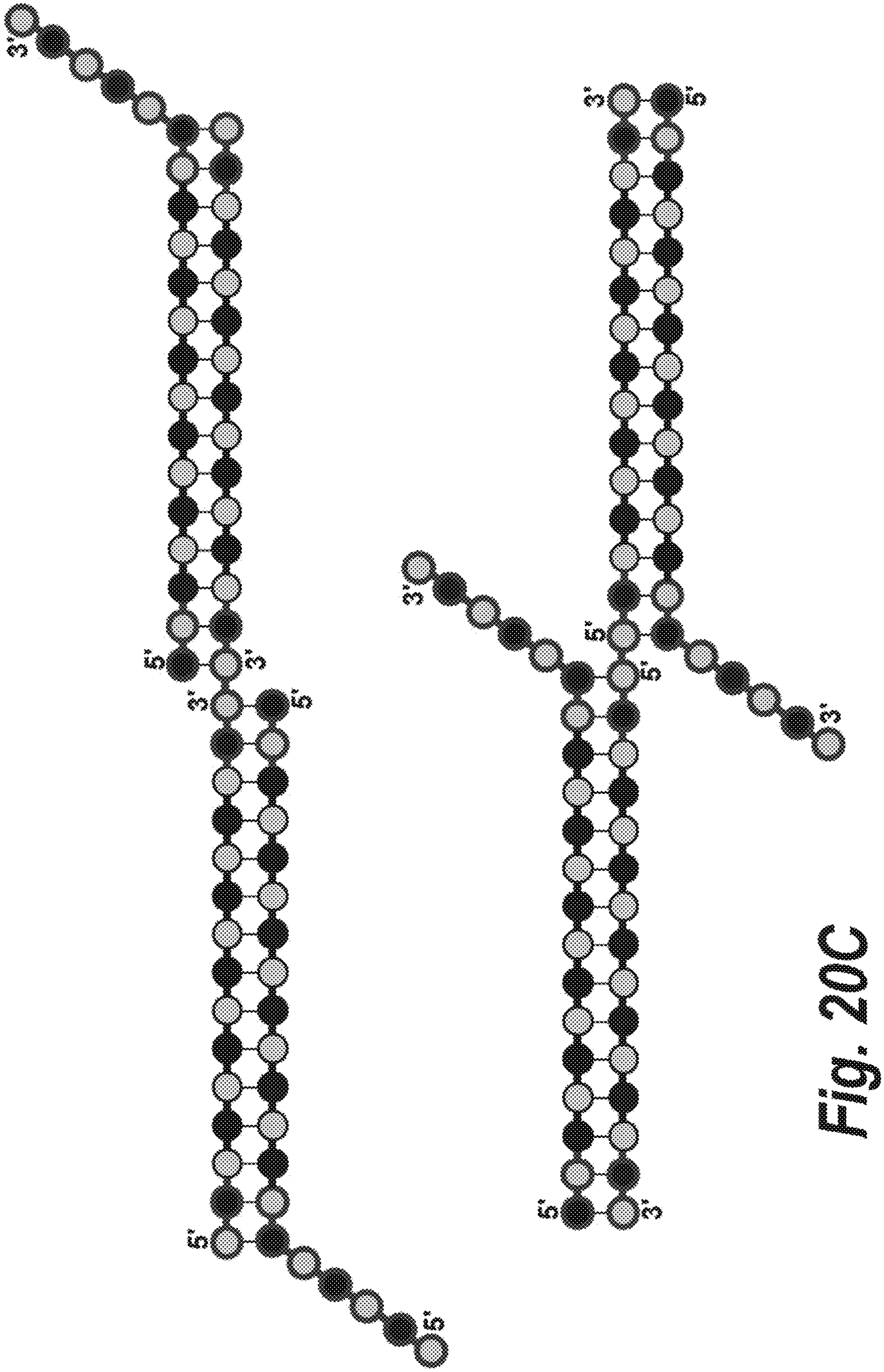

Branched oligonucleotides are provided in various structurally diverse embodiments. As shown in FIG. 17, for example, in some embodiments nucleic acids attached at the branching points are single stranded or double stranded and consist of miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature (Tm~37° C.) for fast dissociation upon internalization of the branched structure into the cell.

Figure 21:
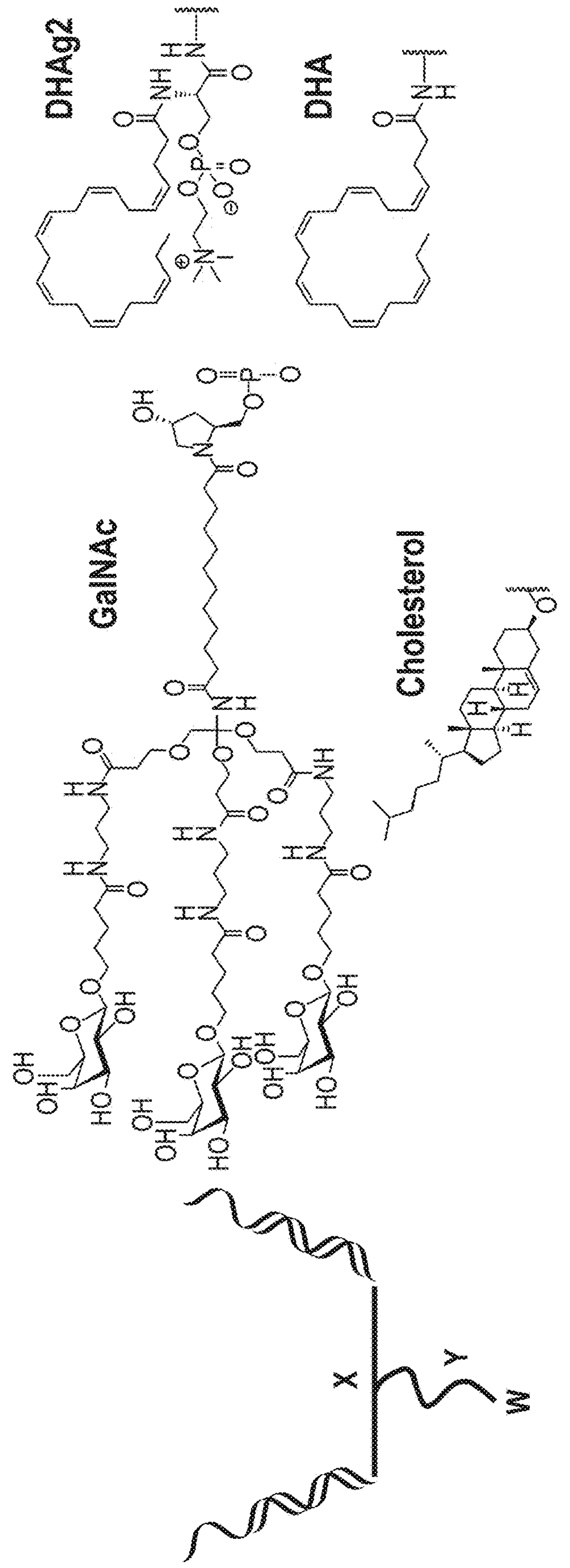
FIG. 21 shows branched oligonucleotides of the invention with conjugated bioactive moieties.
Figure 22:
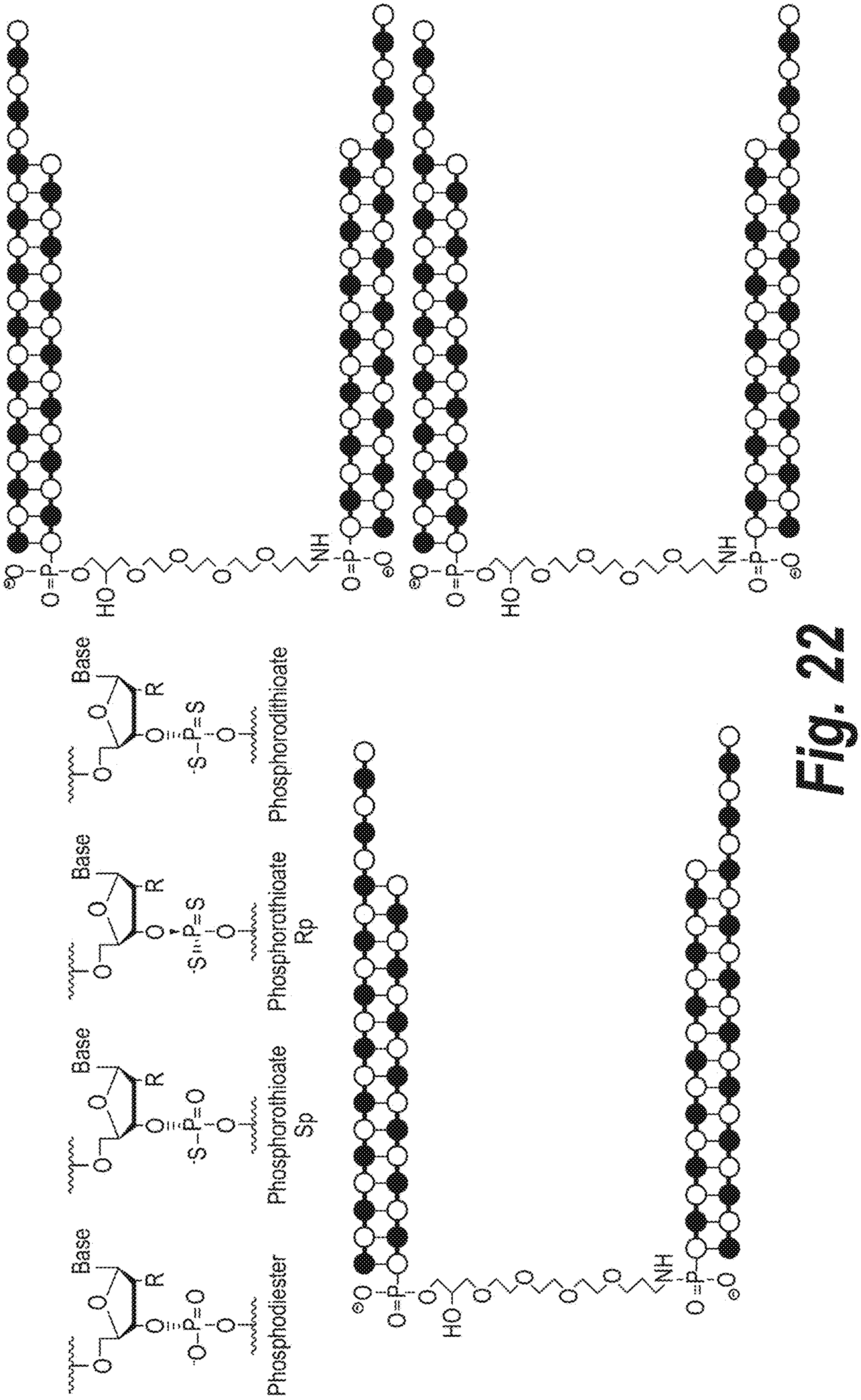
FIG. 22 shows the relationship between phosphorothioate content and stereoselectivity.
Figure 23:
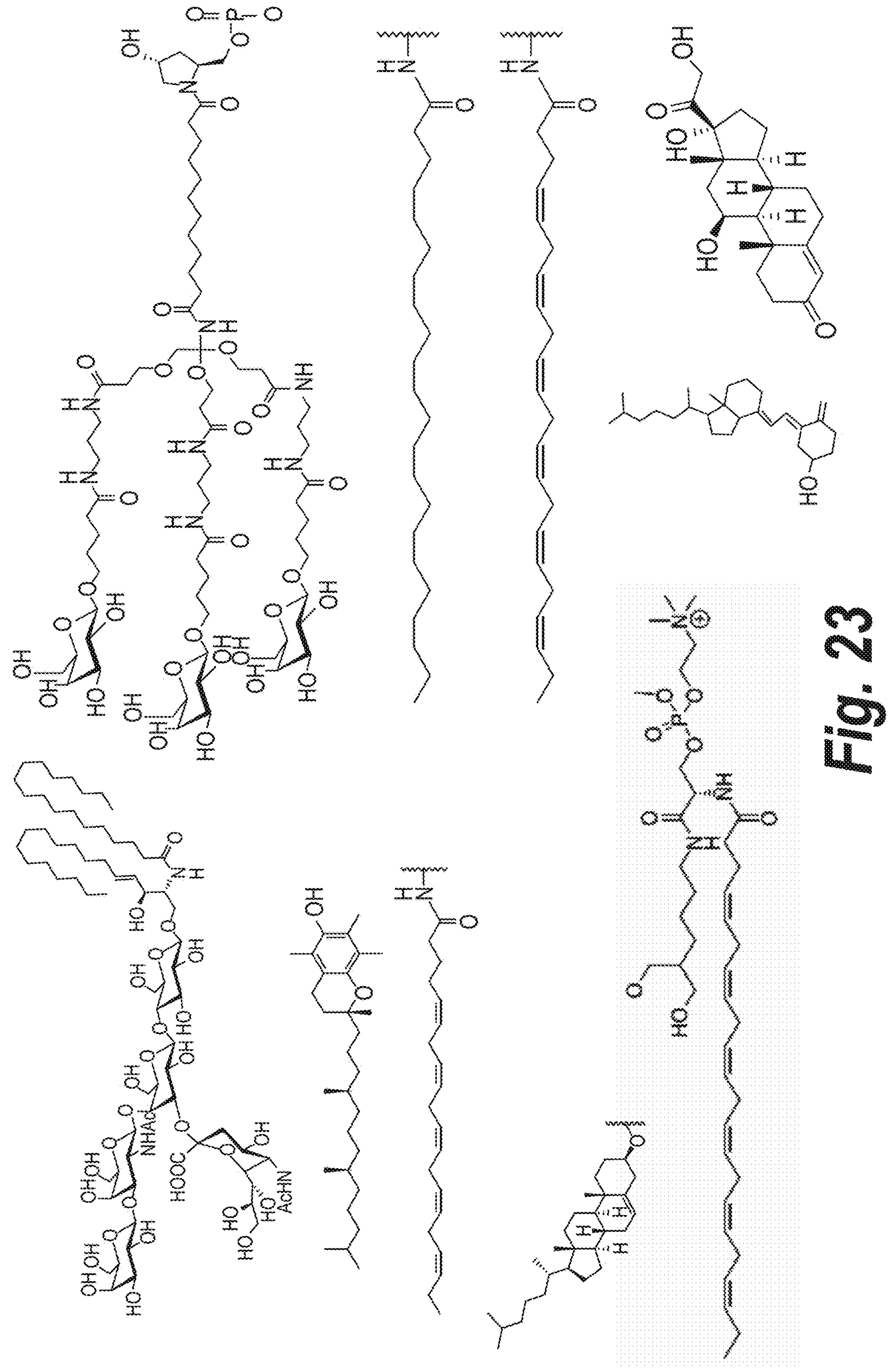
FIG. 23 depicts exemplary hydrophobic moieties.
Figure 24:
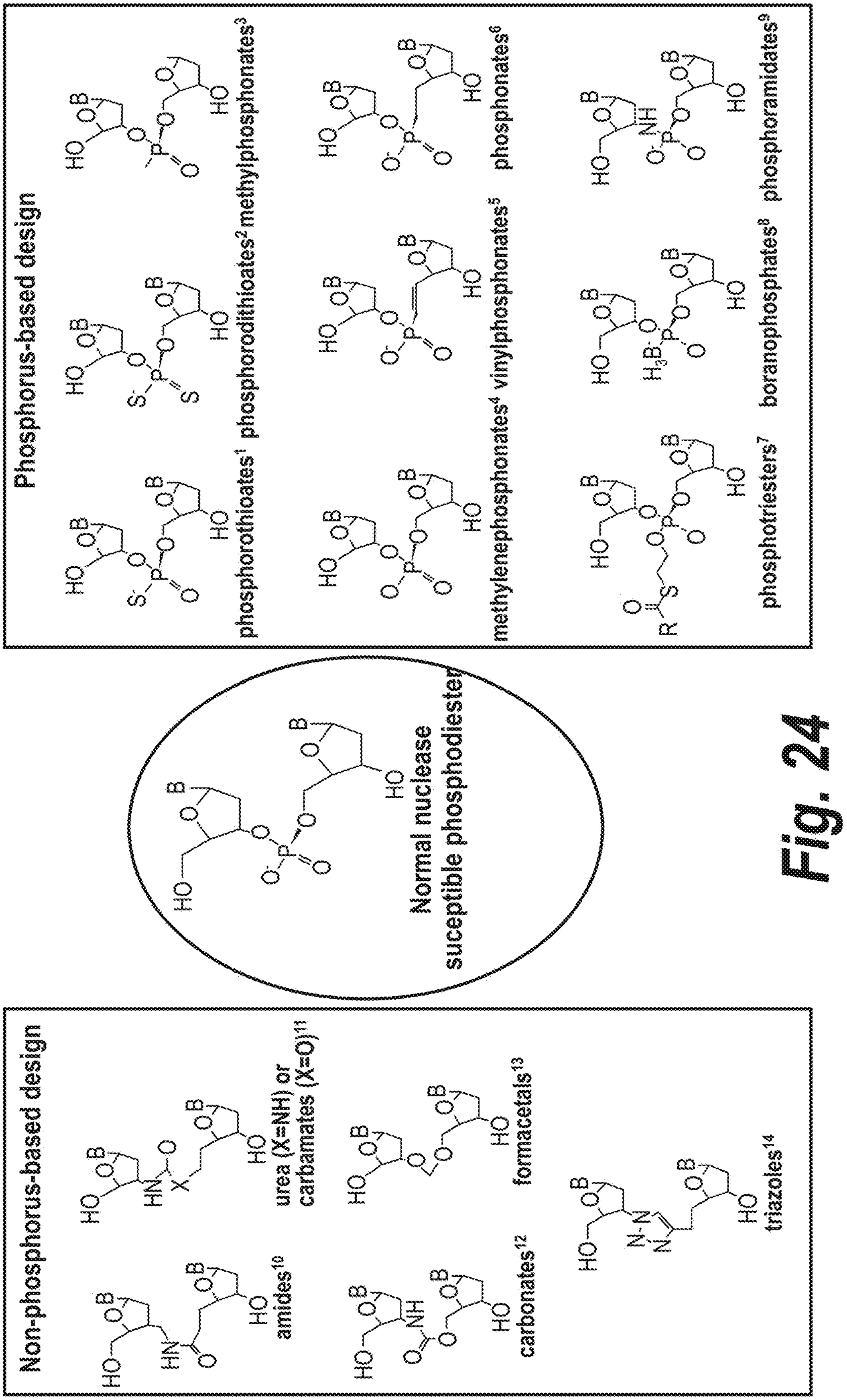
FIG. 24 depicts exemplary internucleotide linkages.
Figure 25:
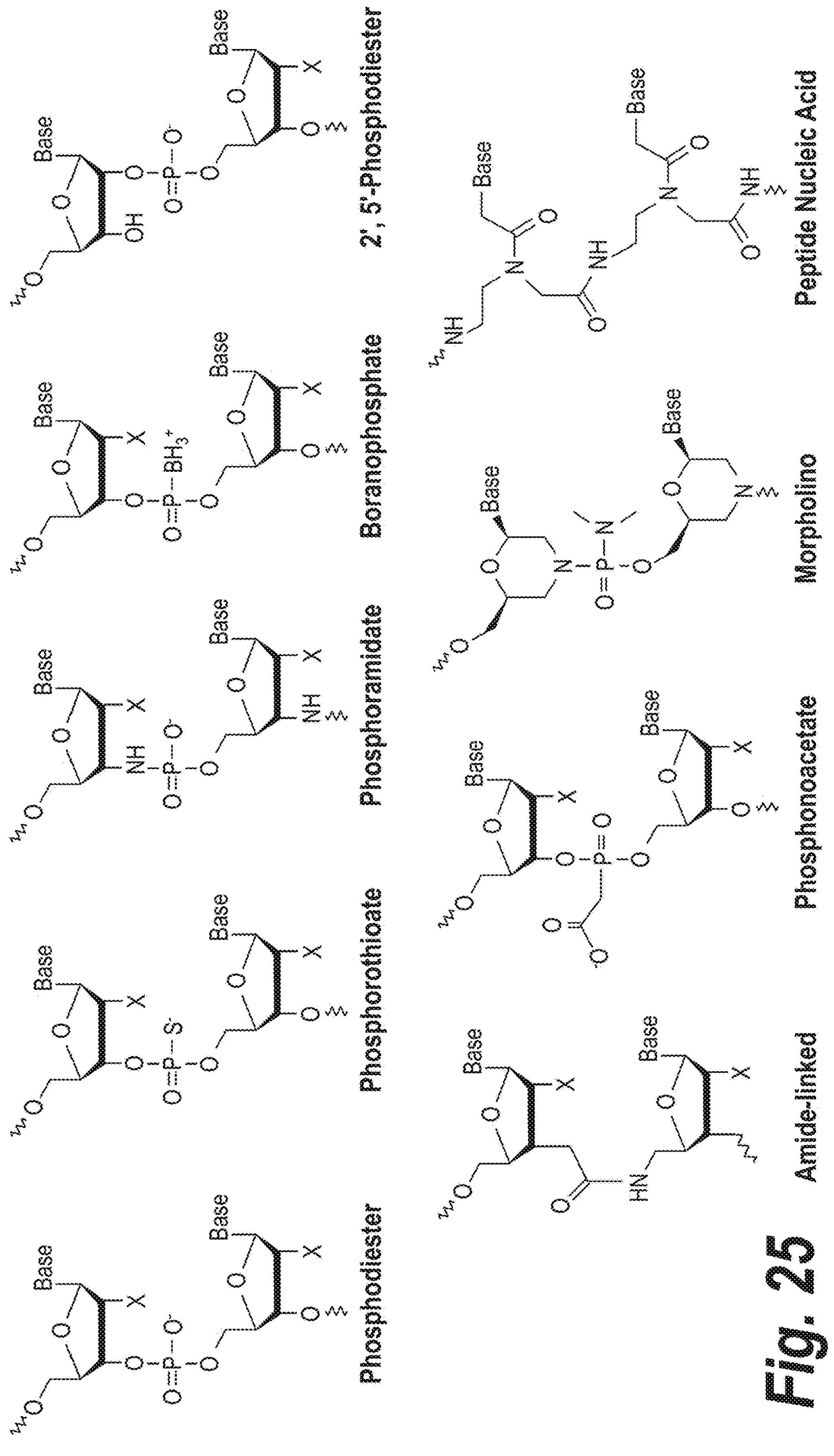
FIG. 25 depicts exemplary internucleotide backbone linkages.
Figure 26:
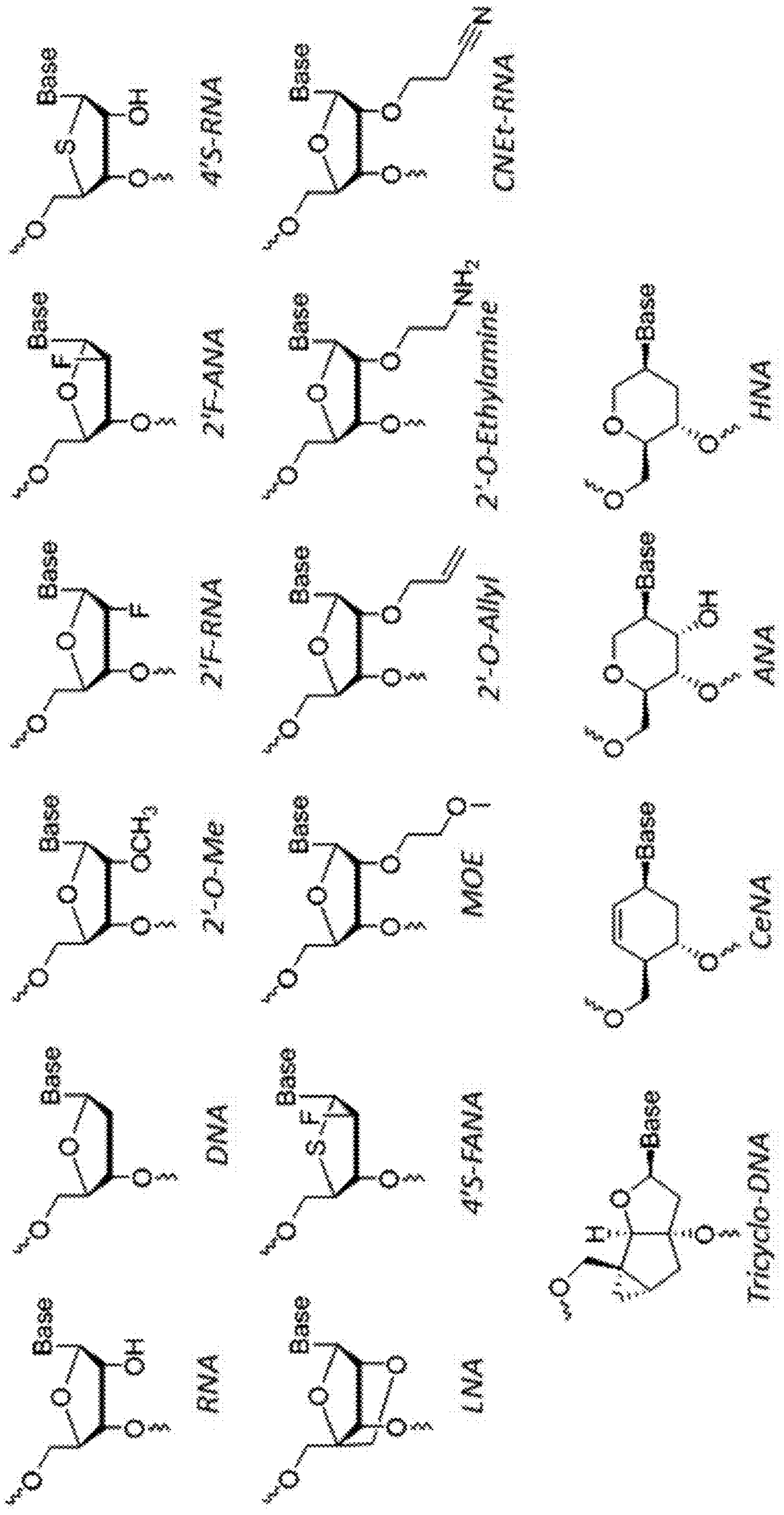
FIG. 26 depicts exemplary sugar modifications.
Figure 27:
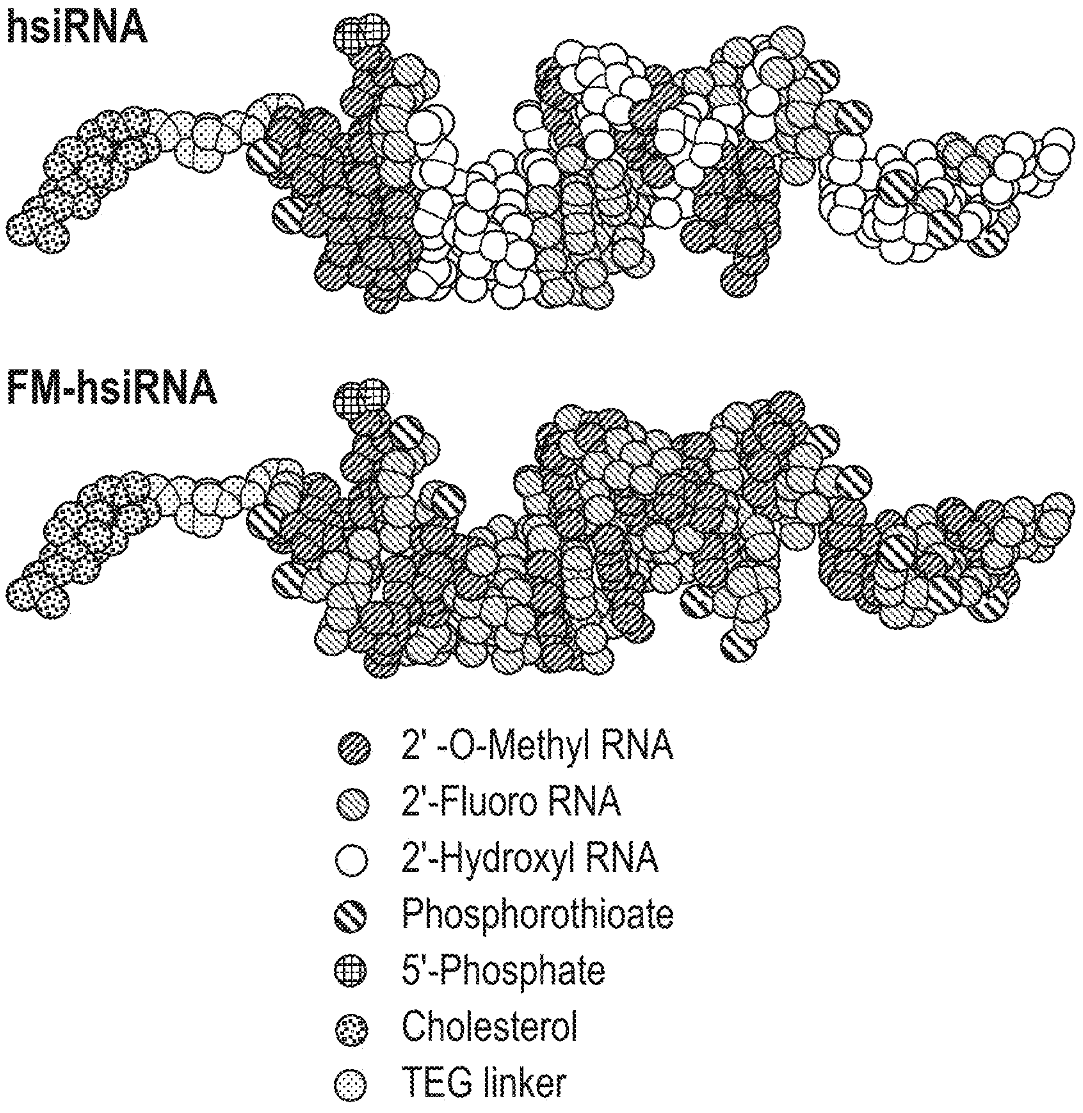
FIG. 27 illustrates the structures of hsiRNA and fully metabolized (FM) hsiRNA.
Figure 28:
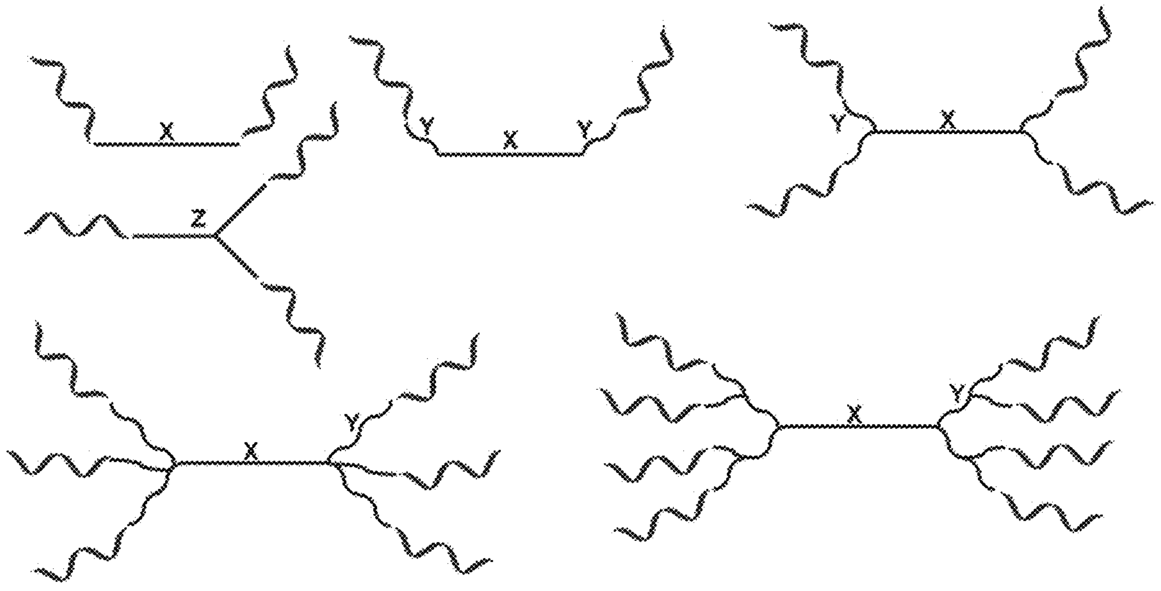
FIG. 28 depicts the chemical diversity of single stranded fully modified oligonucleotides. The single stranded oligonucleotides can consist of gapmers, mixmers, miRNA inhibitors, SSOs, PMOs, or PNAs.

As shown in FIG. 21, Di-siRNA branched oligonucleotides may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

The presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides comprise a variety of therapeutic nucleic acids, including ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Non-limiting embodiments of branched oligonucleotide configurations are disclosed in FIGS. 11, 17-19, 25-27, and 50-52. Non-limiting examples of linkers, spacers and branching points are disclosed in FIG. 13.

Linkers

In an embodiment of the branched oligonucleotide, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole. In another embodiment, each linker is a structure selected from the formulas of FIG. 17.

VII. Compound of Formula (I)

In another aspect, provided herein is a branched oligonucleotide compound of formula (I):

$$L\text{-}(N)_n \qquad (I)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (I) optionally further comprises one or more branch point B, and one or more spacer S; wherein B is independently for each occurrence a polyvalent organic species or derivative thereof, S is independently for each occurrence selected from an ethylene glycol chain, an alkyl chain, a peptide, RNA, DNA, a phosphate, a phosphonate, a phosphoramidate, an ester, an amide, a triazole, and combinations thereof.

Moiety N is an RNA duplex comprising a sense strand and an antisense strand; and n is 2, 3, 4, 5, 6, 7 or 8. In some embodiments, the antisense strand of N comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2). In further embodiments, N includes strands that are capable of targeting one or more of the target sequences 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6). The sense strand and antisense strand may each independently comprise one or more chemical modifications.

In some embodiments, the compound of formula (I) has a structure selected from formulas (I-1)-(I-9) of Table 3.

TABLE 3

| | |
|---|---|
| N—L—N | (I-1) |
| N—S—L—S—N | (I-2) |
| 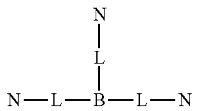 | (I-3) |
| 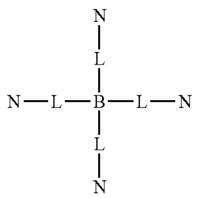 | (I-4) |

TABLE 3-continued

| | |
|---|---|
| 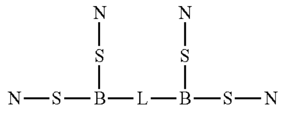 | (I-5) |
| 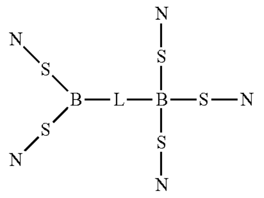 | (I-6) |
| 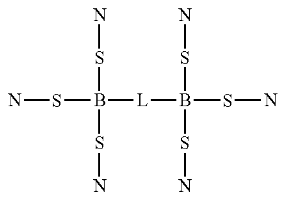 | (I-7) |
| 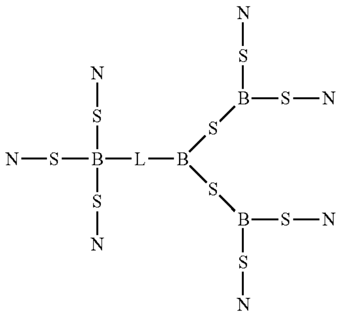 | (I-8) |
| 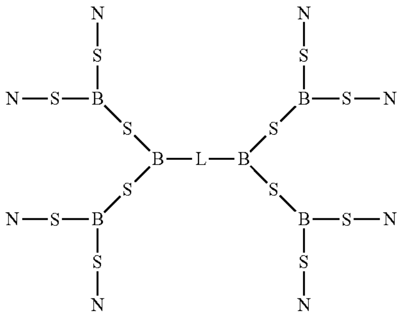 | (I-9) |

In one embodiment, the compound of formula (I) is formula (I-1). In another embodiment, the compound of formula (I) is formula (I-2). In another embodiment, the compound of formula (I) is formula (1-3). In another embodiment, the compound of formula (I) is formula (1-4). In another embodiment, the compound of formula (I) is formula (I-5). In another embodiment, the compound of formula (I) is formula (I-6). In another embodiment, the compound of formula (I) is formula (1-7). In another embodiment, the compound of formula (I) is formula (1-8). In another embodiment, the compound of formula (I) is formula (1-9).

In an embodiment of the compound of formula (I), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of formula (I), each linker is an ethylene glycol chain. In another embodiment, each linker is an alkyl chain. In another embodiment of the compound of formula (I), each linker is a peptide. In another embodiment of the compound of formula (I), each linker is RNA. In another embodiment of the compound of formula (I), each linker is DNA. In another embodiment of the compound of formula (I), each linker is a phosphate. In another embodiment, each linker is a phosphonate. In another embodiment of the compound of formula (I), each linker is a phosphoramidate. In another embodiment of the compound of formula (I), each linker is an ester. In another embodiment of the compound of formula (I), each linker is an amide. In another embodiment of the compound of formula (I), each linker is a triazole. In another embodiment of the compound of formula (I), each linker is a structure selected from the formulas of FIG. 17.

Figure 16:
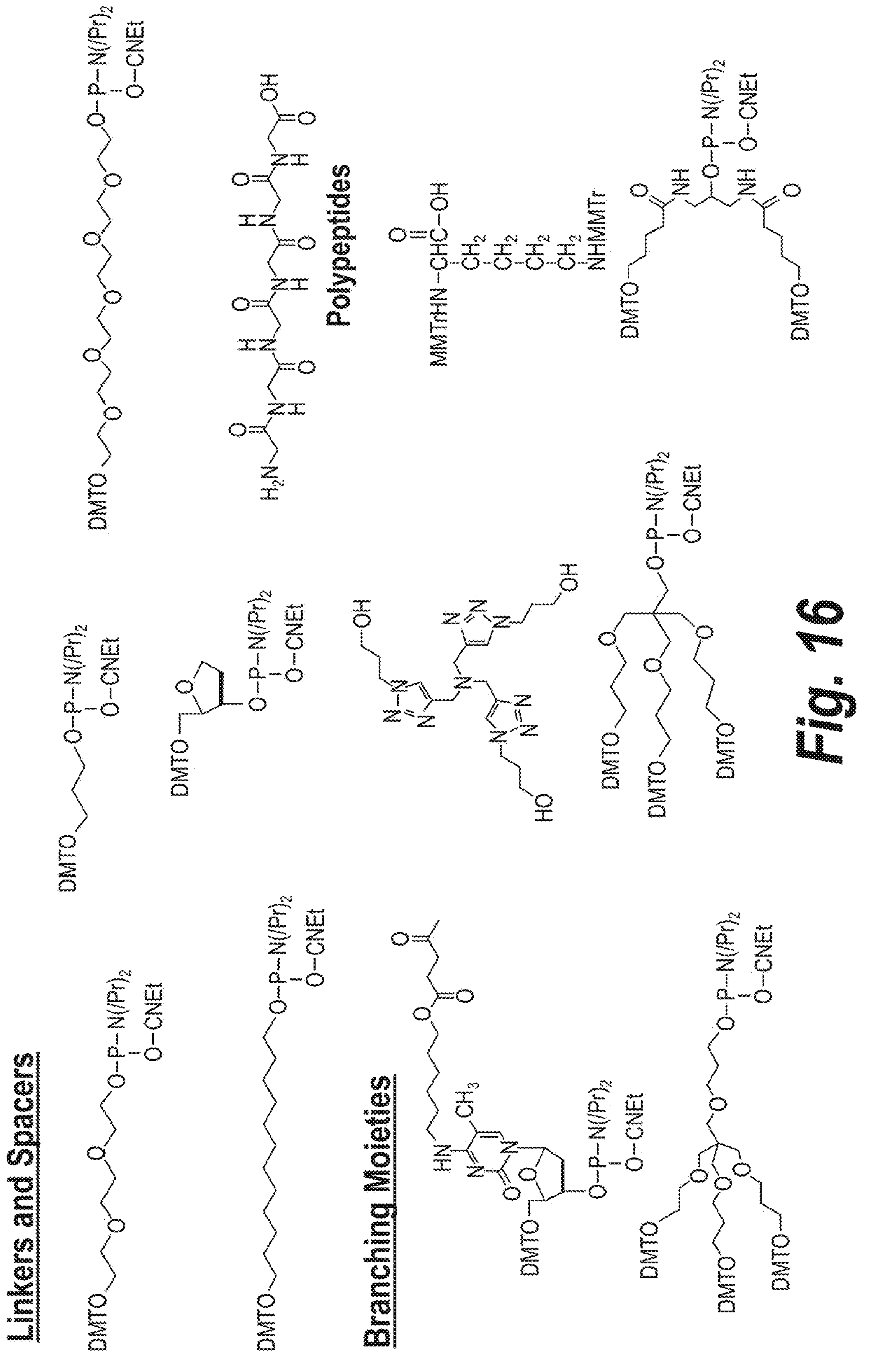
FIG. 16 shows exemplary amidite linkers, spacers and branching moieties.

In one embodiment of the compound of formula (I), B is a polyvalent organic species. In another embodiment of the compound of formula (I), B is a derivative of a polyvalent organic species. In one embodiment of the compound of formula (I), B is a triol or tetrol derivative. In another embodiment, B is a tri- or tetra-carboxylic acid derivative. In another embodiment, B is an amine derivative. In another embodiment, B is a tri- or tetra-amine derivative. In another embodiment, B is an amino acid derivative. In another embodiment of the compound of formula (I), B is selected from the formulas of FIG. 16.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of formula (I), each nucleic acid comprises one or more chemically-modified nucleotides. In an embodiment of the compound of formula (I), each nucleic acid consists of chemically-modified nucleotides. In certain embodiments of the compound of formula (I), >95%, >90%, >85%, >80%, >75%, >70%, >65%, >60%, >55% or >50% of each nucleic acid comprises chemically-modified nucleotides.

In some embodiments, each antisense strand independently comprises a 5' terminal group R selected from the groups of Table 4.

TABLE 4

| | |
|---|---|
| 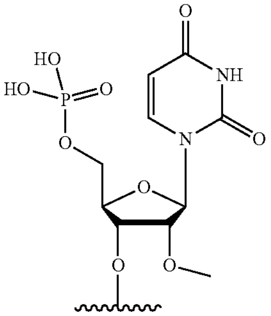 | $R^1$ |

TABLE 4-continued

| | |
|---|---|
| 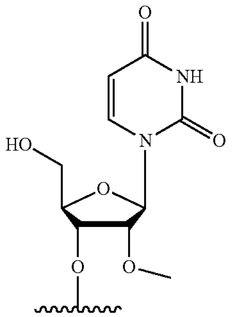 | $R^2$ |
| 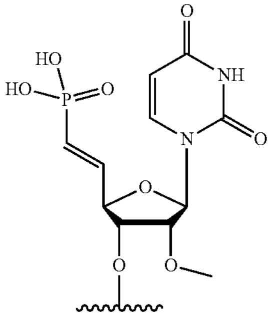 | $R^3$ |
| 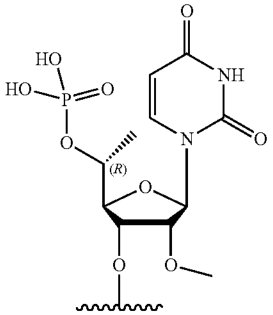 | $R^4$ |
| 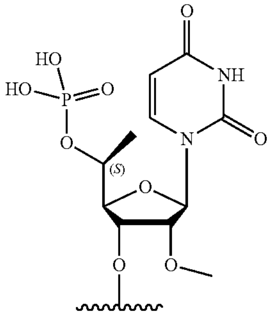 | $R^5$ |
| 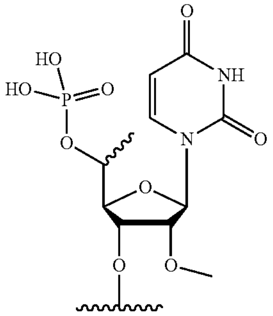 | $R^6$ |

TABLE 4-continued

| | |
|---|---|
| 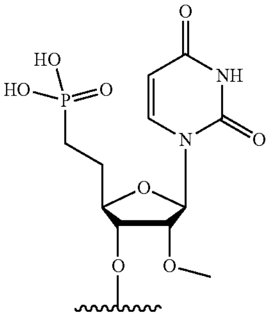 | $R^7$ |
| 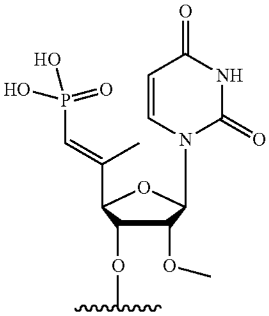 | $R^8$ |

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (II)

In some embodiments, the compound of formula (I) has the structure of formula (II):

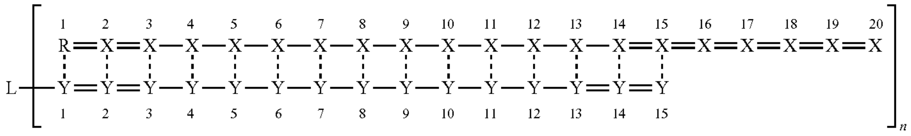

(II)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and --- represents, individually for each occurrence, a base-pairing interaction or a mismatch.

In certain embodiments, the structure of formula (II) does not contain mismatches. In one embodiment, the structure of formula (II) contains 1 mismatch. In another embodiment, the compound of formula (II) contains 2 mismatches. In another embodiment, the compound of formula (II) contains 3 mismatches. In another embodiment, the compound of formula (II) contains 4 mismatches. In some embodiments, each nucleic acid consists of chemically-modified nucleotides.

In certain embodiments, >95%, >90%, >85%, >80%, >75%, >70%, >65%, >60%, >55% or >50% of X's of the structure of formula (II) are chemically-modified nucleotides. In other embodiments, >95%, >90%, >85%, >80%, >75%, >70%, >65%, >60%, >55% or >50% of X's of the structure of formula (II) are chemically-modified nucleotides.

Structure of Formula (III)

In some embodiments, the compound of formula (I) has the structure of formula (III):

(III)

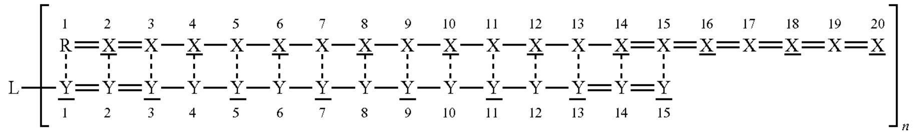

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In some embodiments, X is chosen from the group consisting of 2'-deoxy-2'-fluoro modified adenosine, guanosine, uridine or cytidine. In some embodiments, X is chosen from the group consisting of 2'-O-methyl modified adenosine, guanosine, uridine or cytidine. In some embodiments, Y is chosen from the group consisting of 2'-deoxy-2'-fluoro modified adenosine, guanosine, uridine or cytidine. In some embodiments, Y is chosen from the group consisting of 2'-O-methyl modified adenosine, guanosine, uridine or cytidine.

In certain embodiments, the structure of formula (III) does not contain mismatches. In one embodiment, the structure of formula (III) contains 1 mismatch. In another embodiment, the compound of formula (III) contains 2 mismatches. In another embodiment, the compound of formula (III) contains 3 mismatches. In another embodiment, the compound of formula (III) contains 4 mismatches.

Structure of Formula (IV)

In some embodiments, the compound of formula (I) has the structure of formula (IV):

(IV)

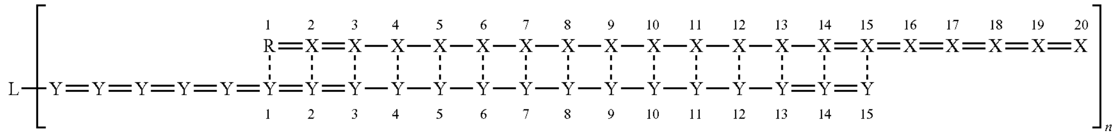

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and --- represents, individually for each occurrence, a base-pairing interaction or a mismatch.

In certain embodiments, the structure of formula (IV) does not contain mismatches. In one embodiment, the structure of formula (IV) contains 1 mismatch. In another embodiment, the compound of formula (IV) contains 2 mismatches. In another embodiment, the compound of formula (IV) contains 3 mismatches. In another embodiment, the compound of formula (IV) contains 4 mismatches. In some embodiments, each nucleic acid consists of chemically-modified nucleotides.

In certain embodiments, >95%, >90%, >85%, >80%, >75%, >70%, >65%, >60%, >55% or >50% of X's of the structure of formula (IV) are chemically-modified nucleotides. In other embodiments, >95%, >90%, >85%, >80%, >75%, >70%, >65%, >60%, >55% or >50% of X's of the structure of formula (IV) are chemically-modified nucleotides.

Structure of Formula (V)

In some embodiments, the compound of formula (I) has the structure of formula (V):

(V)

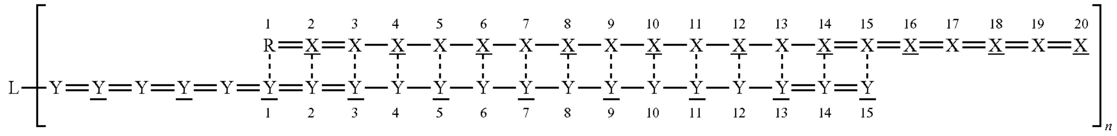

wherein X, for each occurrence, independently, is a nucleotide comprising a 2'-deoxy-2'-fluoro modification; X, for each occurrence, independently, is a nucleotide comprising a 2'-O-methyl modification; Y, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In some embodiments, X is chosen from the group consisting of 2'-O-methyl modified adenosine, guanosine, uridine or cytidine. In some embodiments, Y is chosen from the group consisting of 2'-deoxy-2'-fluoro modified adenosine, guanosine, uridine or cytidine. In some embodiments, Y is chosen from the group consisting of 2'-O-methyl modified adenosine, guanosine, uridine or cytidine.

In certain embodiments, the structure of formula (V) does not contain mismatches. In one embodiment, the structure of formula (V) contains 1 mismatch. In another embodiment, the compound of formula (V) contains 2 mismatches. In another embodiment, the compound of formula (V) contains 3 mismatches. In another embodiment, the compound of formula (V) contains 4 mismatches.

Variable Linkers

In an embodiment of the compound of formula (I), L has the structure of L1:

(L1)

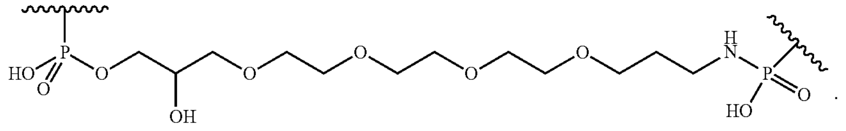

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VI), L has the structure of L1.

In an embodiment of the compound of formula (I), L has the structure of L2:

(L2)

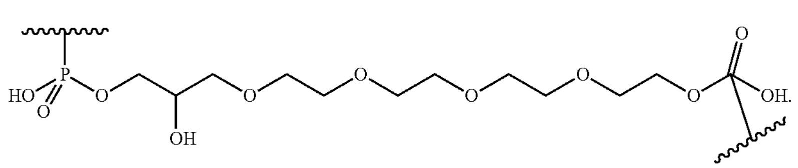

In an embodiment of L2, R is R3 and n is 2. In an embodiment of the structure of formula (II), L has the structure of L2. In an embodiment of the structure of formula (III), L has the structure of L2. In an embodiment of the structure of formula (IV), L has the structure of L2. In an embodiment of the structure of formula (V), L has the structure of L2. In an embodiment of the structure of formula (VI), L has the structure of L2. In an embodiment of the structure of formula (VI), L has the structure of L2.

Delivery System

In a third aspect, provided herein is a delivery system for therapeutic nucleic acids having the structure of formula (VI):

$$L—(cNA)_n \quad (VI)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein formula (VI) optionally further comprises one or more branch point B, and one or more spacer S; wherein B is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8.

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In some embodiments, the compound of formula (VI) has a structure selected from formulas (VI-1)-(VI-9) of Table 5:

TABLE 5

| | |
|---|---|
| ANc—L—cNA | (VI-1) |
| ANc—S—L—S—cNA | (VI-2) |
| 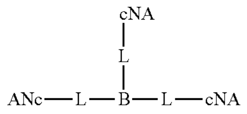 | (VI-3) |
| 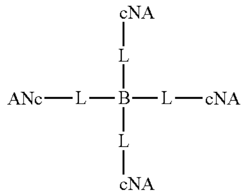 | (VI-4) |
| 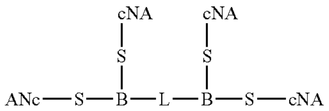 | (VI-5) |
| 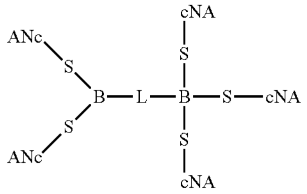 | (VI-6) |

TABLE 5-continued (VI-7)

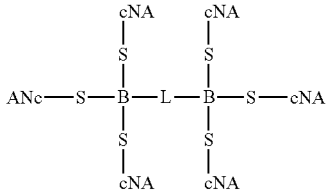

(VI-8)

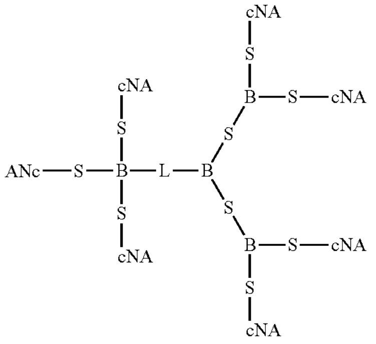

(VI-9)

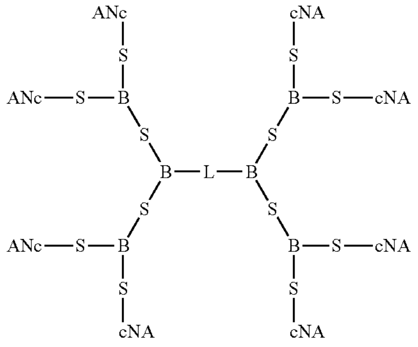

In some embodiments, the compound of formula (VI) is the structure of formula (VI-1). In some embodiments, the compound of formula (VI) is the structure of formula (VI-2). In some embodiments, the compound of formula (VI) is the structure of formula (VI-3). In some embodiments, the compound of formula (VI) is the structure of formula (VI-4). In some embodiments, the compound of formula (VI) is the structure of formula (VI-5). In some embodiments, the compound of formula (VI) is the structure of formula (VI-6). In some embodiments, the compound of formula (VI) is the structure of formula (VI-7). In some embodiments, the compound of formula (VI) is the structure of formula (VI-8). In some embodiments, the compound of formula (VI) is the structure of formula (VI-9).

In some embodiments, the compound of formulas (VI) (including, e.g., formulas (VI-1)-(VI-9), each cNA independently comprises at least 15 contiguous nucleotides. In some embodiments, each cNA independently consists of chemically-modified nucleotides.

In some embodiments, the delivery system further comprises n therapeutic nucleic acids (NA), wherein each NA comprises a region of complementarity which is substantially complementary to 5' GUUUAAUAAAGAUUCACCAAGUUUCACGCAAA 3' (SEQ ID NO: 1) or 5' UGGACCCUAGUUUAAUAAAGAUUCACCAAG 3' (SEQ ID NO: 2). In further embodiments, NA includes strands that are capable of targeting one or more of the target sequences 5' GAUUCACCAAGUUUA 3' (SEQ ID NO: 4), 5' CAAGUUUCACGCAAA 3' (SEQ ID NO: 5), and 5' CCUAGUUUAAUAAAGAUUCA 3' (SEQ ID NO: 6).

Also, each NA is hybridized to at least one cNA. In one embodiment, the delivery system is comprised of 2 NAs. In another embodiment, the delivery system is comprised of 3 NAs. In another embodiment, the delivery system is comprised of 4 NAs. In another embodiment, the delivery system is comprised of 5 NAs. In another embodiment, the delivery system is comprised of 6 NAs. In another embodiment, the delivery system is comprised of 7 NAs. In another embodiment, the delivery system is comprised of 8 NAs.

In some embodiments, each NA independently comprises at least 16 contiguous nucleotides. In some embodiments, each NA independently comprises 16-20 contiguous nucleotides. In some embodiments, each NA independently comprises 16 contiguous nucleotides. In another embodiment, each NA independently comprises 17 contiguous nucleotides. In another embodiment, each NA independently comprises 18 contiguous nucleotides. In another embodiment, each NA independently comprises 19 contiguous nucleotides. In another embodiment, each NA independently comprises 20 contiguous nucleotides.

In some embodiments, each NA comprises an unpaired overhang of at least 2 nucleotides. In another embodiment, each NA comprises an unpaired overhang of at least 3 nucleotides. In another embodiment, each NA comprises an unpaired overhang of at least 4 nucleotides. In another embodiment, each NA comprises an unpaired overhang of at least 5 nucleotides. In another embodiment, each NA comprises an unpaired overhang of at least 6 nucleotides. In some embodiments, the nucleotides of the overhang are connected via phosphorothioate linkages.

In some embodiments, each NA, independently, is selected from the group consisting of: DNA, siRNAs, antagomiRs, miRNAs, gapmers, mixmers, or guide RNAs. In one embodiment, each NA, independently, is a DNA. In another embodiment, each NA, independently, is a siRNA. In another embodiment, each NA, independently, is an antagomiR. In another embodiment, each NA, independently, is a miRNA. In another embodiment, each NA, independently, is a gapmer. In another embodiment, each NA, independently, is a mixmer. In another embodiment, each NA, independently, is a guide RNA. In some embodiments, each NA is the same. In some embodiments, each NA is not the same.

In some embodiments, the delivery system further comprising n therapeutic nucleic acids (NA) has a structure selected from formulas (I), (II), (III), (IV), (V), (VI), and embodiments thereof described herein. In one embodiment, the delivery system has a structure selected from formulas (I), (II), (III), (IV), (V), (VI), and embodiments thereof described herein further comprising 2 therapeutic nucleic acids (NA). In another embodiment, the delivery system has a structure selected from formulas (I), (II), (III), (IV), (V), (VI), and embodiments thereof described herein further comprising 3 therapeutic nucleic acids (NA). In one embodiment, the delivery system has a structure selected from formulas (I), (II), (III), (IV), (V), (VI), and embodiments thereof described herein further comprising 4 therapeutic nucleic acids (NA). In one embodiment, the delivery system has a structure selected from formulas (I), (II), (III), (IV), (V), (VI), and embodiments thereof described herein further comprising 5 therapeutic nucleic acids (NA). In one embodiment, the delivery system has a structure selected from formulas (I), (II), (III), (IV), (V), (VI), and embodiments thereof described herein further comprising 6 therapeutic nucleic acids (NA). In one embodiment, the delivery system has a structure selected from formulas (I), (II), (III), (IV), (V), (VI), and embodiments thereof described herein further comprising 7 therapeutic nucleic acids (NA). In one embodiment, the delivery system has a structure selected from formulas (I), (II), (III), (IV), (V), (VI), and embodiments thereof described herein further comprising 8 therapeutic nucleic acids (NA).

In one embodiment, the delivery system has a structure selected from formulas (I), (II), (III), (IV), (V), (VI), further comprising a linker of structure L1 or L2 wherein R is $R^3$ and n is 2. In another embodiment, the delivery system has a structure selected from formulas (I), (II), (III), (IV), (V), (VI), further comprising a linker of structure L1 wherein R is $R^3$ and n is 2. In another embodiment, the delivery system has a structure selected from formulas (I), (II), (III), (IV), (V), (VI), further comprising a linker of structure L2 wherein R is $R^3$ and n is 2.

In an embodiment of the delivery system, the target of delivery is selected from the group consisting of brain, liver, skin, kidney, spleen, pancreas, colon, fat, lung, muscle, and thymus. In one embodiment, the target of delivery is the brain. In another embodiment, the target of delivery is the striatum of the brain. In another embodiment, the target of delivery is the cortex of the brain. In another embodiment, the target of delivery is the striatum of the brain. In one embodiment, the target of delivery is the liver. In one embodiment, the target of delivery is the skin. In one embodiment, the target of delivery is the kidney. In one embodiment, the target of delivery is the spleen. In one embodiment, the target of delivery is the pancreas. In one embodiment, the target of delivery is the colon. In one embodiment, the target of delivery is the fat. In one embodiment, the target of delivery is the lung. In one embodiment, the target of delivery is the muscle. In one embodiment, the target of delivery is the thymus. In one embodiment, the target of delivery is the spinal cord.

In certain embodiments, compounds of the invention are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phoshorothioated single oligonucleotides containing at least 3, optimally 5-20 phosphorothioated bonds.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2nd edition).

Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an ApoE target sequence) is tested for its ability to specifically degrade mutant mRNA (e.g., ApoE mRNA and/or the production of ApoE protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant ApoE cDNA). Standard siRNA, modified siRNA or vectors able to produce siRNA from U-looped mRNA are co-transfected. Selective reduction in target mRNA (e.g., ApoE mRNA) and/or target protein (e.g., ApoE protein) is measured. Reduction of target mRNA or protein can be compared to levels of target mRNA or protein in the absence of an RNAi agent or in the presence of an RNAi agent that does not target ApoE mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VIII. Methods of Treatment

In one aspect, the present invention provides for both prophylactic and therapeutic methods of treating a subject at risk of (or susceptible to) a disease or disorder caused, in whole or in part, by abnormalities in cholesterol transport. In one embodiment, the disease or disorder is such that ApoE levels in the central nervous system (CNS) have been found to be predictive of neurodegeneration progression. In another embodiment, the disease or disorder is a polyglutamine disorder. In a preferred embodiment, the disease or disorder one in which reduction of ApoE in the CNS reduces clinical manifestations seen in neurodegenerative diseases such as AD and ALS.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a CNS cell expressing ApoE with a therapeutic agent (e.g., a RNAi agent or vector or transgene encoding same) that is specific for a target sequence within the gene (e.g., SEQ ID NOs:1, 2 or 3), such that sequence specific interference with the gene is achieved. These methods can be performed in vitro (e.g., by culturing the cell with the agent) or, alternatively, in vivo (e.g., by administering the agent to a subject).

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the invention can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

In embodiments of this aspect, the prophylactic and therapeutic methods are directed to treating or managing neurodegenerative diseases or disorders in which reduction of ApoE in the CNS reduces abnormal amyloid accumulation. In a non-limiting example, the RNA silencing agent is a branched oligonucleotide as described in sections VI and VII herein which is administered to a patient diagnosed as having or at risk for developing an amyloid-related neurodegenerative disease or disorder such as Alzheimer's disease, cerebral amyloid angiopathy, or mild-to-moderate cognitive impairment. The patient can be treated following diagnosis, at varying stage of the disease, or as a prophylactic measure in instances where genetic traits, family history, or other factors put the patient at risk for the neurodegenerative disease or disorder. Successful dosage amounts and schedules may be established and monitored by metrics indicative of effective treatment, for example the extent of inhibition, delay, prevention or reduction of symptoms such as cognitive decline, beta-amyloid plaque formation in the brain, and neurodegeneration which are detected following the initiation of treatment.

In one embodiment, the patient is diagnosed as having or at risk for developing Alzheimer's disease, and the patient is otherwise in good health. Treatment is carried out by administering a Di-siRNA$^{ApoE}$, i.e., a branched oligonucleotide including two nucleic acids each between 15 and 35 bases in length. Each nucleic acid features a region of complementarity which is substantially complementary to a portion of ApoE mRNA, e.g., one or more of the target sequences set forth in Table 1, Table 2, or Table 7. The two nucleic acids are connected to one another by, for example, a linker, spacer, or branching point. Each of the nucleic acids may independently be single stranded (ss) RNA or double stranded (ds) RNA. For example, each of the nucleic acids may independently be an antisense molecule or a GAPMER.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4\times10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. In another embodiment, the dosage can be in the order of about 10 mg to about 50 mg per organ, or preferably about 20 mg to about 30 mg per organ. The dosage can be an amount effective to treat or prevent a neurodegenerative disease or disorder, e.g., AD or ALS. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 g to 10 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 g to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

IX. Pharmaceutical Compositions and Methods of Administration

The invention pertains to uses of the above-described agents for prophylactic and/or therapeutic treatments as described infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 μg to 1000 mg may be administered; in some embodiments, 10, 30, 100 or 1000 μg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-ApoE RNA silencing agent of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the invention can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood MJ. (2011). Delivery of siRNA to the mouse brain by systemic injection of targeted exosomes. Nat Biotechnol. 2011 April; 29(4):341-5. doi: 10.1038/nbt.1807; E1-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mäger I, Wood M J. (2013). Exosomes for targeted siRNA delivery across biological barriers. Adv Drug Deliv Rev. 2013 March; 65(3): 391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

X. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. In Vitro Identification of Hyper-Functional ApoE Targeting Sequences 1.1 Identification of siRNAs Targeting Mouse ApoE that Cause a Dose-Dependent Decrease in mRNA and Protein The mouse ApoE gene was used as a target for mRNA knockdown. A panel of cholesterol-conjugated siRNAs targeting the mouse ApoE gene was developed and screened in primary mouse astrocytes in vitro compared to untreated control cells. The siRNAs were each tested at a concentration of 1.5 μM and the mRNA was evaluated with the QuantiGene gene expression assay (ThermoFisher, Waltham, MA) at the 72 hours timepoint. FIG. 1A reports the results of the screen.

Figure 1B:
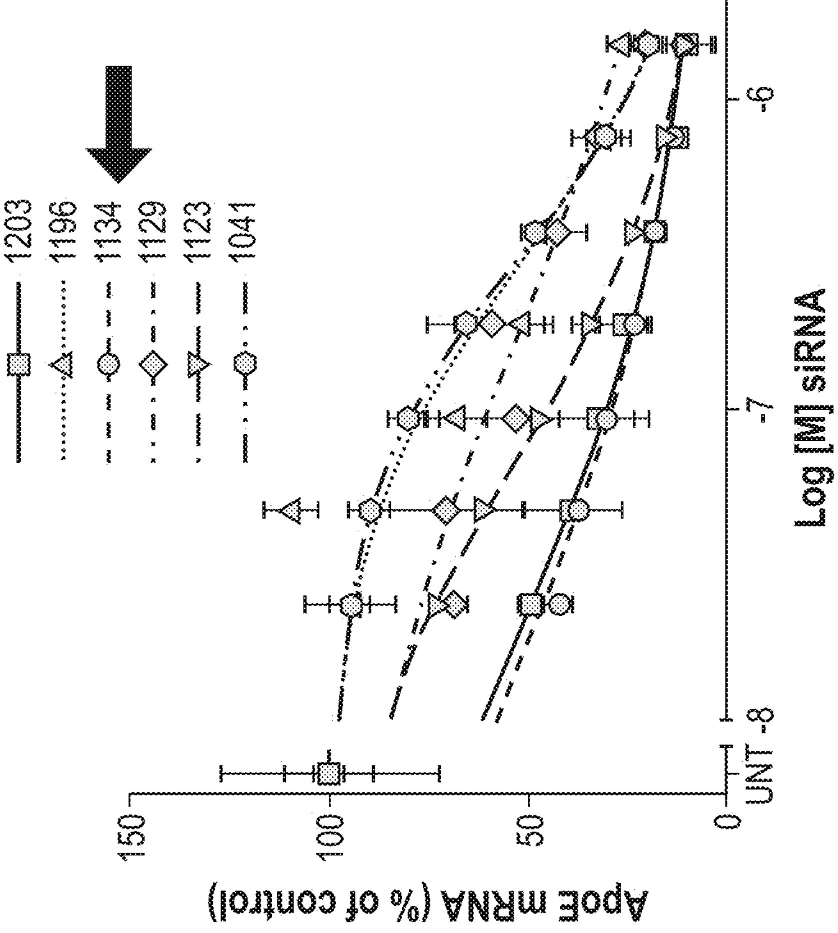
Figure 1C:
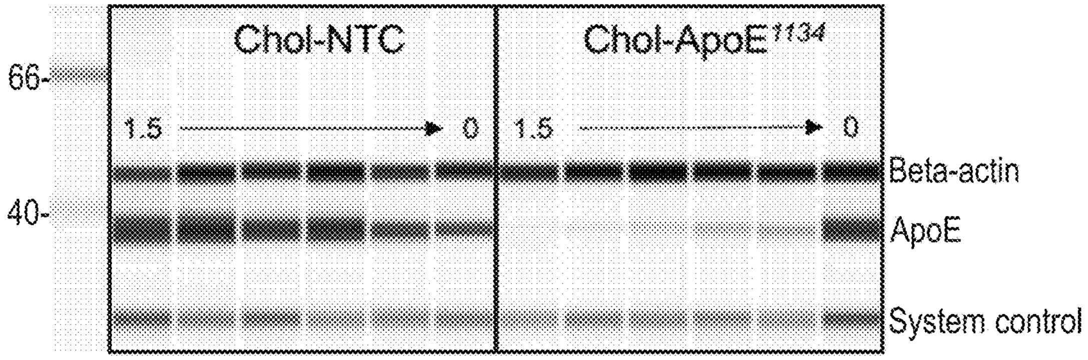

As illustrated in FIG. 1B, dose response curves and IC50 values were obtained for the hit compounds identified in the screen, and 1134 and 1203 were chosen for further studies based on their high efficacy and potency. FIG. 1C illustrates a dose response for 1134 showing protein silencing in mouse primary astrocyte evaluated after 1 week with the ProteinSimple (San Jose, CA) protein quantitation assay. Table 1 below describes the two targets, 1134 and 1203.

TABLE 1

Mouse ApoE mRNA targets, antisense strands, and sense strands.

| ID | Targeting sequence (32 BP) | Antisense sequence (5'-3') | Sense sequence (5'-3') |
|---|---|---|---|
| 1134 | GUUUAAUAAAG AUUCACCAAGU UUCACGCAAA (SEQ ID NO: 1) | UUGGAUAUGGA UGUUGUUGCAG (SEQ ID NO: 10) | GCAACAACAUC CAUAUCCAA (SEQ ID NO: 12) |
| 1203 | CCUUGCUUAAU AAAGAUUCUCC GAGCACAUU (SEQ ID NO: 9) | UCUCGGAGAAU CUUUAUUAAGC (SEQ ID NO: 11) | UUAAUAAAGAU UCUCCGAGA (SEQ ID NO: 13) |

Figure 2A:
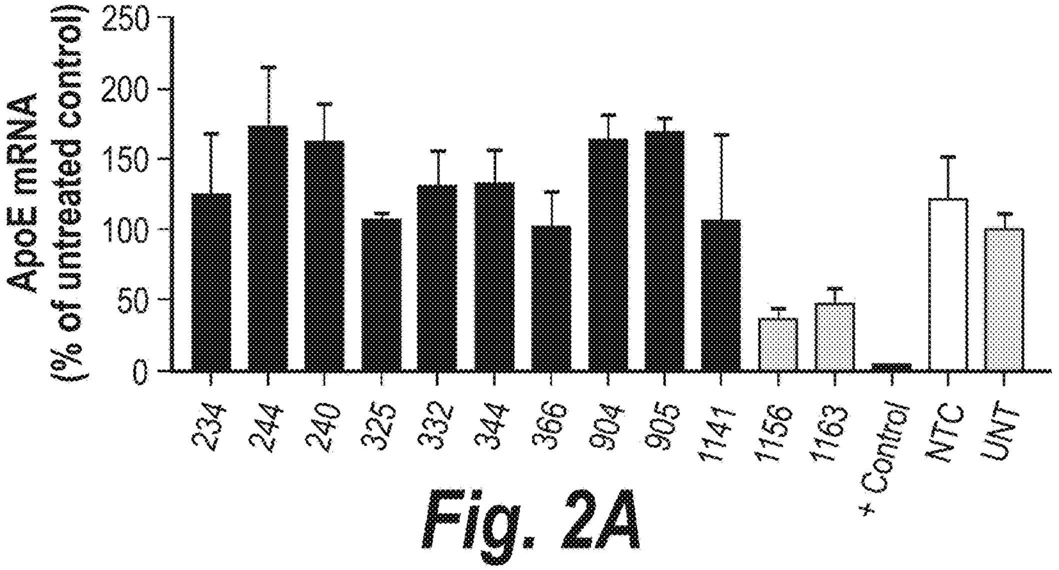
FIGS. 2A-2B illustrate the identification of novel targeting sequences showing mRNA silencing in mRNA based human cell models.
Figure 2B:
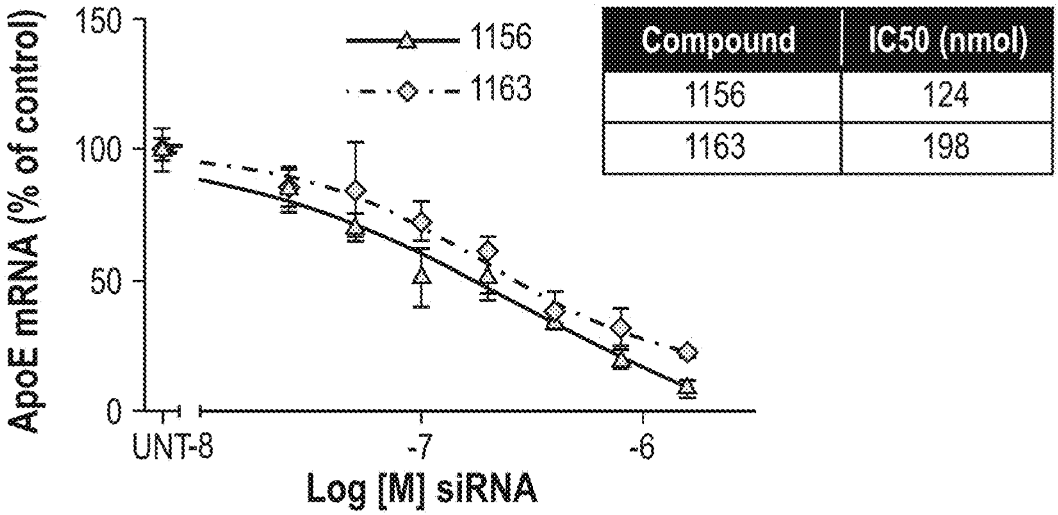

1.2 Identification of siRNAs Targeting Human ApoE that Cause a Dose-Dependent Decrease in mRNA and Protein The human ApoE gene was used as a target for mRNA knockdown. A panel of siRNAs targeting the human ApoE gene was developed and screened in human HepG2 cells in vitro compared to untreated control cells. The siRNAs were each tested at a concentration of 1.5 μM and the mRNA was evaluated with the Quantigene gene expression assay (ThermoFisher, Waltham, MA) at the 72 hours timepoint. FIG. 2A reports the results of the screen and 1156 and 1163 were chosen for further studies based on their high efficacy and potency. Then, and as illustrated in FIG. 2B, dose response curves and IC50 values were obtained for the hit compounds from the screen. Table 2 below describes the two targets, 1156 and 1163.

TABLE 2

Human ApoE mRNA targets, antisense strands, and sense strands.

| ID | Targeting sequence (32 BP) | Antisense sequence (5'-3') | Sense sequence (5'-3') |
|---|---|---|---|
| 1156 | GUUUAAUAAAG AUUCACCAAGU UUCACGCAAA (SEQ ID NO: 1) | UAAACUUGGUG AAUCUUUAU (SEQ ID NO: 14) | GAUUCACCAAG UUUA (SEQ ID NO: 4) |
| 1163 | GUUUAAUAAAG AUUCACCAAGU UUCACGCAAA (SEQ ID NO: 1) | UUUGCGUGAAA CUUGGUGAA (SEQ ID NO: 15) | CAAGUUUCACG CAAA (SEQ ID NO: 5) |

Figure 43:
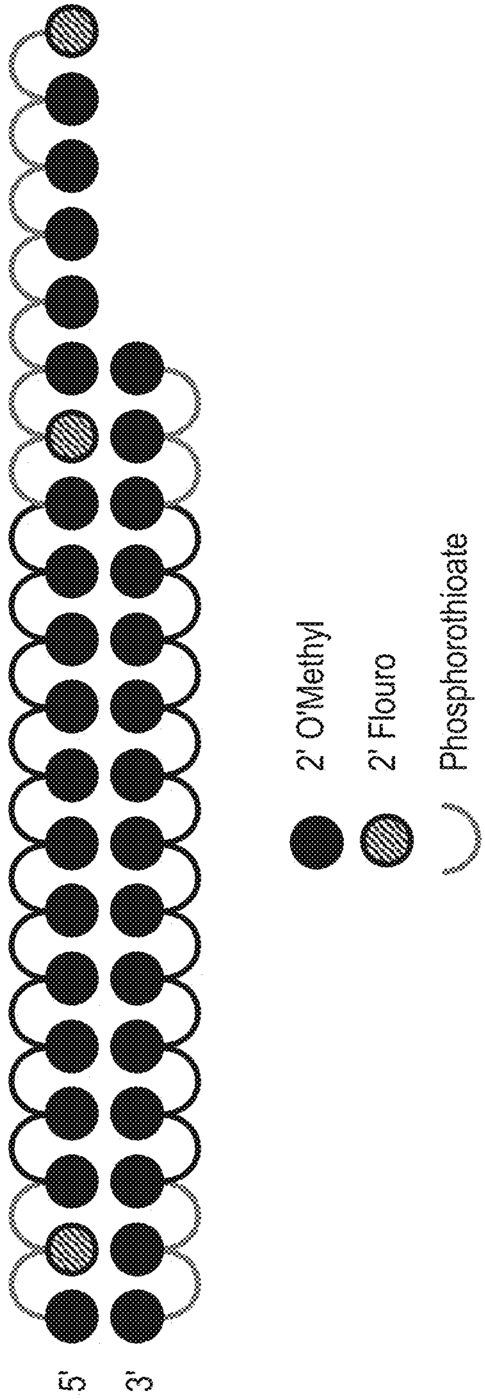
FIG. 43 illustrates an siRNA bearing a methyl-rich substitution pattern.
Figure 44A:
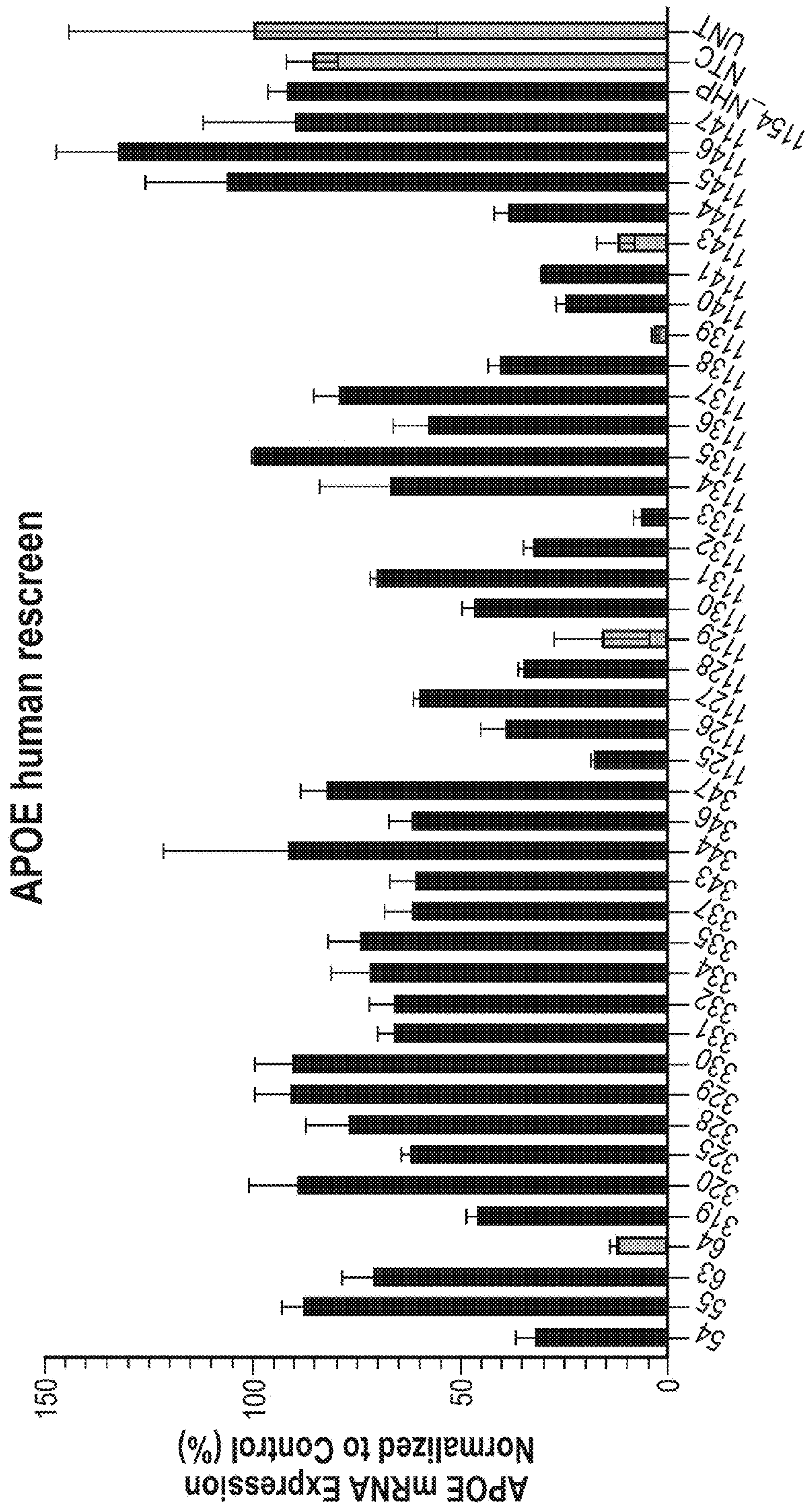
FIGS. 44A-44C illustrate the identification of novel targeting sequences showing mRNA silencing in mRNA based human cell models.
Figure 44B:
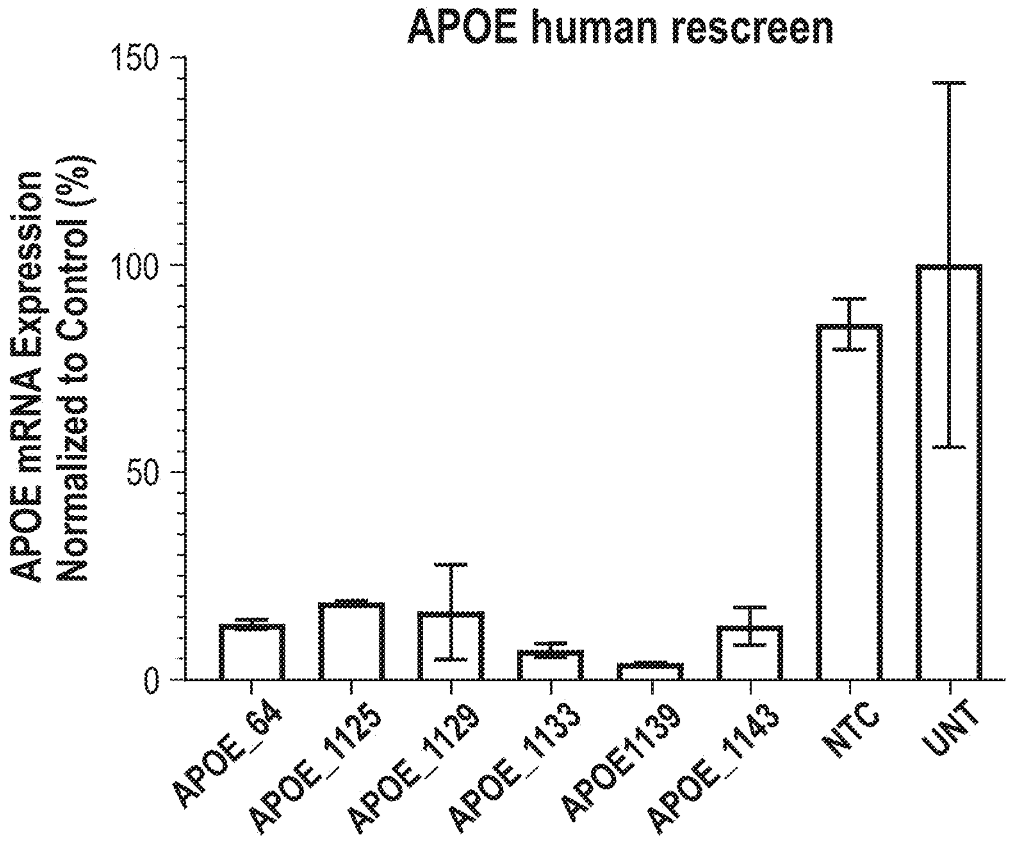
Figure 44C:
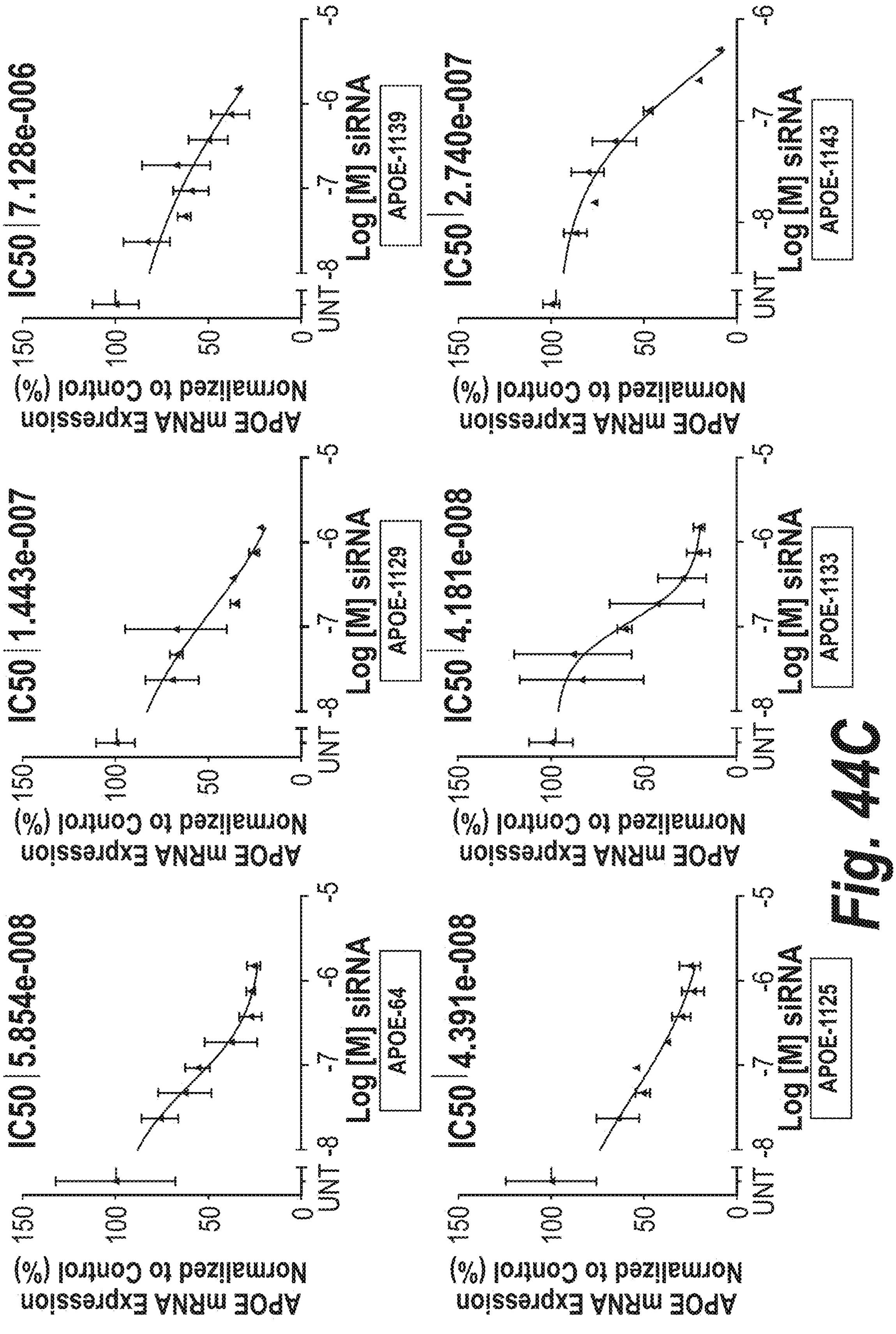

A second screen of the human ApoE gene, this time with siRNAs bearing the methyl-rich chemistry pattern of FIG. 43, was conducted by testing a number of target regions of the gene. FIG. 44A reports the results of the screen and 64, 1125, 1129, 1133, 1139, and 1143 were chosen for further studies based on their high efficacy and potency, as illustrated in FIG. 44B. Then, and as illustrated in FIG. 44C, dose response curves and IC50 values were obtained for the hit compounds from the screen (first row, left to right: 64, 1129, 1139; second row, left to right: 1125, 1133, 1143). Table 7 below describes the target sequences.

TABLE 7

Second screen, Human ApoE mRNA targeting regions, targeting sequences, antisense strands, and sense strands.

| ID | Targeting region | Targeting sequence | Sense sequence (5'-3') | Antisense (5'-3') |
|---|---|---|---|---|
| 64 | CAGGCAGGAAG AUGAAGGUUCU GUGGGCUG (SEQ ID NO: 16) | AGGAAGAUGAA GGUUCUGUG (SEQ ID NO: 20) | GAUGAAGGUUC UGUG (SEQ ID NO: 25) | CACAGAACCUU CAUCUUCCU (SEQ ID NO: 31) |
| 1125 | UCCUGGGGUGG ACCCUAGUUUA AUAAAGAU (SEQ ID NO: 17) | GGGUGGACCCU AGUUUAAUA (SEQ ID NO: 21) | GACCCUAGUUU AAUA (SEQ ID NO: 26) | UAUUAAACUAG GGUCCACCC (SEQ ID NO: 32) |
| 1129 | GGGGUGGACCC UAGUUUAAUAA AGAUUCAC (SEQ ID NO: 18) | GGACCCUAGUU UAAUAAAGA (SEQ ID NO: 22) | CUAGUUUAAUA AAGA (SEQ ID NO: 27) | UCUUUAUUAAA CUAGGGUCC (SEQ ID NO: 33) |
| 1133 | UGGACCCUAGU UUAAUAAAGAU UCACCAAG (SEQ ID NO: 2) | CCUAGUUUAAU AAAGAUUCA (SEQ ID NO: 6) | UUUAAUAAAGA UUCA (SEQ ID NO: 28) | UGAAUCUUUAU UAAACUAGG (SEQ ID NO: 34) |

TABLE 7 -continued

Second screen, Human ApoE mRNA targeting regions, targeting sequences, antisense strands, and sense strands.

| ID | Targeting region | Targeting sequence | Sense sequence (5'-3') | Antisense (5'-3') |
|---|---|---|---|---|
| 1139 | CUAGUUUAAUA AAGAUUCACCA AGUUUCAC (SEQ ID NO: 3) | UUAAUAAAGAU UCACCAAGU (SEQ ID NO: 23) | AAAGAUUCACC AAGU (SEQ ID NO: 29) | ACUUGGUGAAU CUUUAUUAA (SEQ ID NO: 35) |
| 1143* | GUUUAAUAAAG AUUCACCAAGU UUCACGCA (SEQ ID NO: 19) | UAAAGAUUCAC CAAGUUUCA (SEQ ID NO: 24) | AUUCACCAAGU UUCA (SEQ ID NO: 30) | UGAAACUUGGU GAAUCUUUA (SEQ ID NO: 36) |

*same targeting region as 1163

1.3 ApoE Targeting Sequences (Mouse and Human)

Figure 3B:
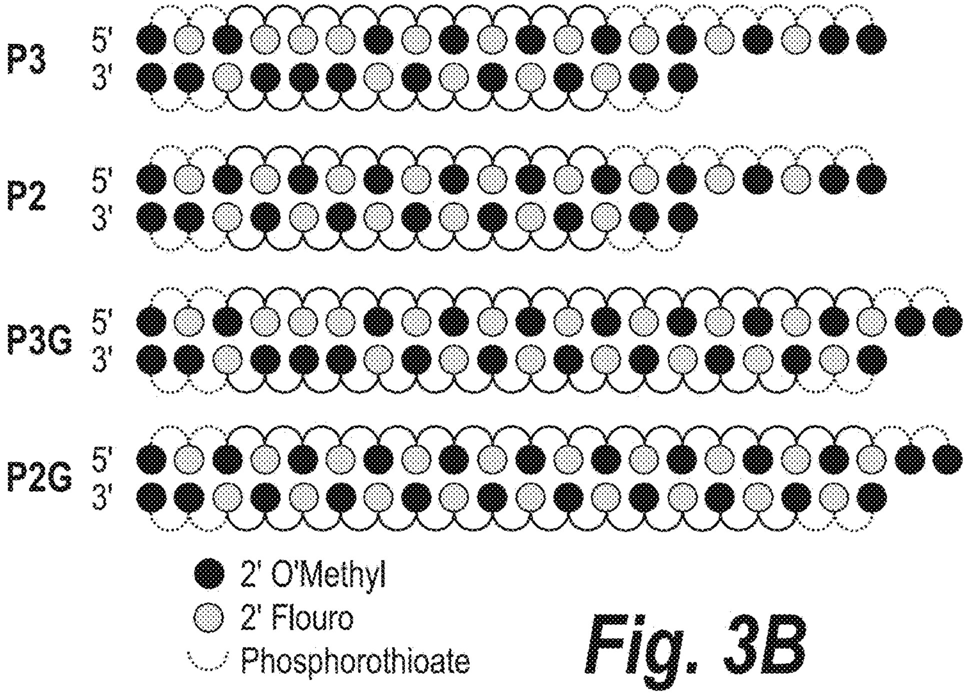

FIG. 3A is a table illustrating the targeting sequences identified in the mouse and human ApoE genes and antisense and sense sequences of oligonucleotides that target such sequences. As illustrated in FIG. 3B, the oligonucleotide sequences can be used in the context of a number of chemical modifications (P2, P3, P2G, P3G) and with different chemical conjugates (e.g. GalNAc, CNS-siRNA, cholesterol). The oligonucleotides can also be used in the context of antisense oligonucleotide gene silencing.

Figure 4A:
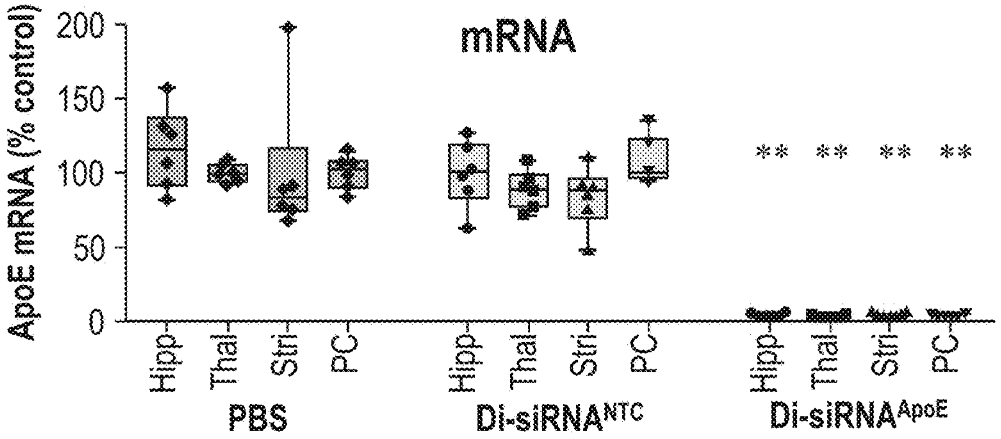
FIGS. 4A-4C illustrate the silencing of mRNA and protein expression throughout the mouse brain 1-month post injection of CNS-siRNA$^{ApoE}$.
Figure 4B:
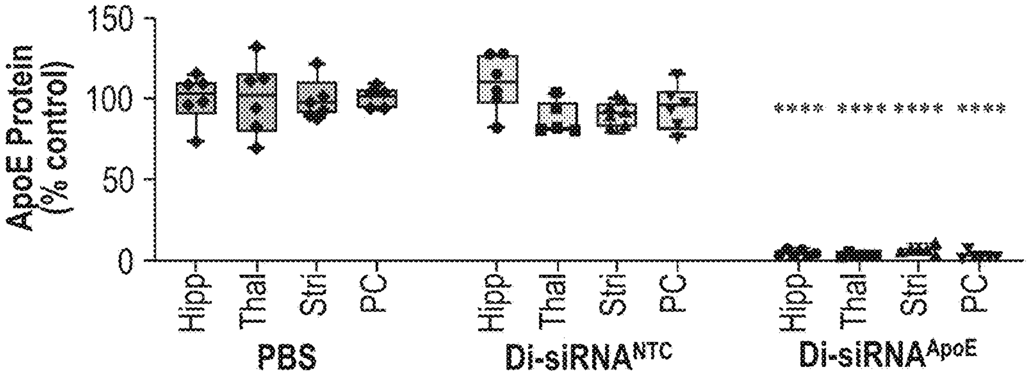
Figure 4C:
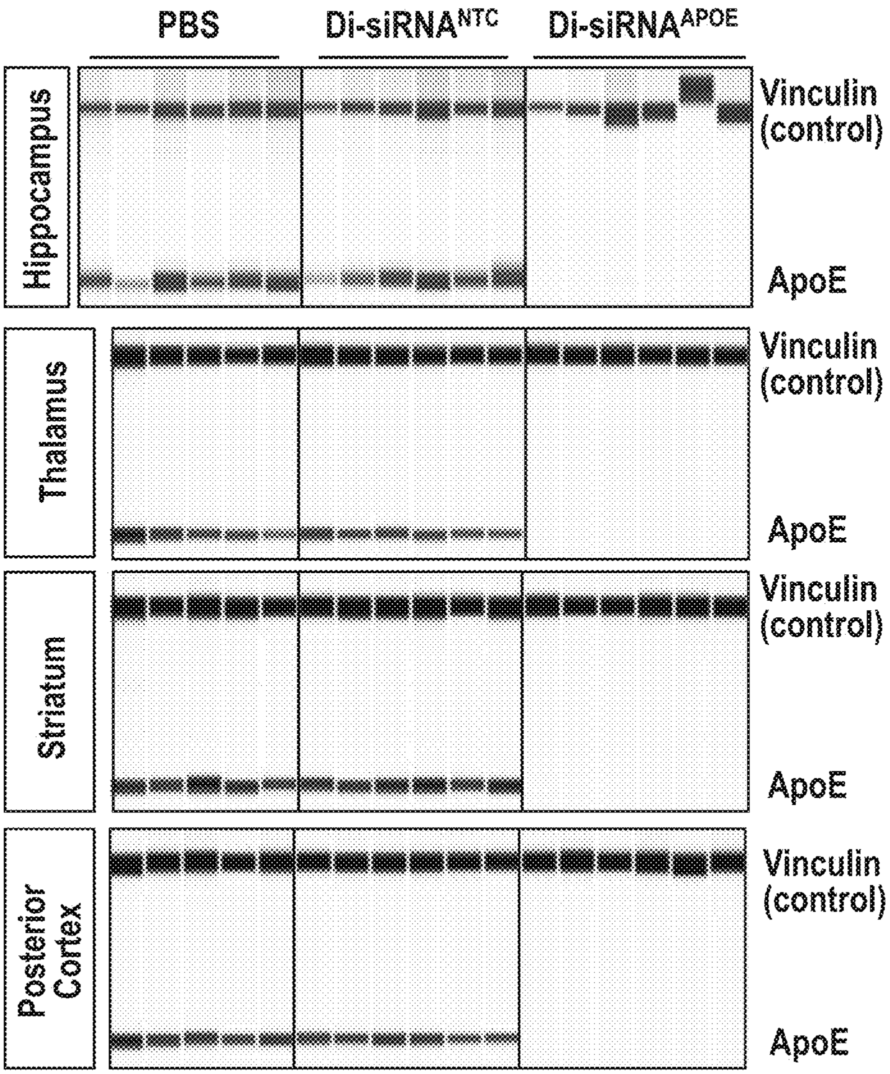

Example 2. In Vivo Efficacy of Tissue-Specific ApoE Targeting siRNAs in Mice 2.1 CNS-siRNA$^{ApoE}$ Silences mRNA and Protein Expression Throughout the Mouse Brain 1-Month Post Injection Di-siRNA$^{ApoE}$ at a dosage of 475 μg was administered via ICV injection to a first group of wild-type mice. A second control group were injected with phosphate-buffered saline (PBS), and a third control group were injected with Di-siRNA$^{NTC}$ (non-targeting control). Each group included six mice. One month after the injection, mRNA silencing was evaluated with QuantiGene in all regions of the brain (FIG. 4A) and protein silencing was evaluated with ProteinSimple (FIG. 4B). Protein silencing throughout the brain was also evaluated with a Western blot (FIG. 4C).

It can be seen that the novel siRNA sequences targeting ApoE show potent in vivo mRNA and protein silencing. Previous reports using oligonucleotides to silence ApoE use sequences that demonstrate a ~50% target mRNA and protein silencing after ICV injection. Without being bound to any particular theory, it is possible that many conclusions made using previous sequences are invalid given the low degree of silencing. In contrast, the novel sequences offer a significant advantage in studying the role of ApoE in neurodegeneration.

2.2 CNS-siRNA$^{ApoE}$ Silences ApoE Protein in the Hippocampus at Low Doses

Figure 5A:
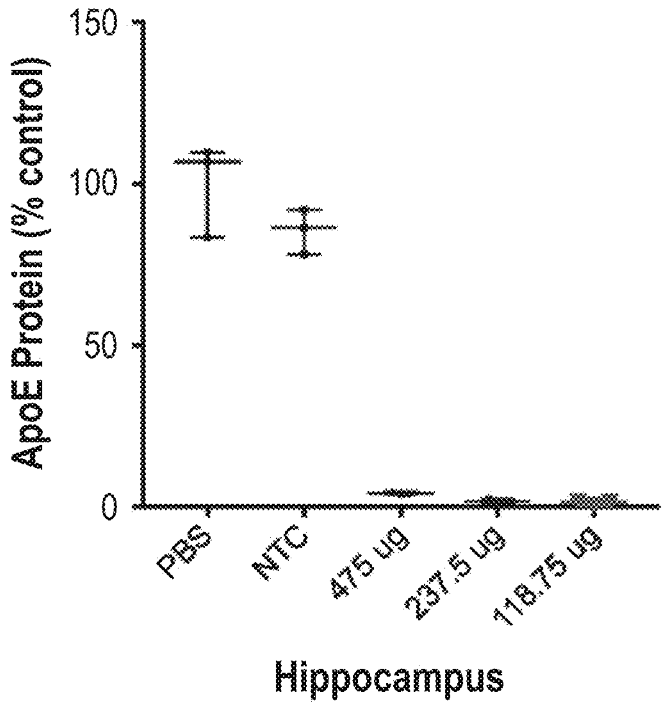
FIGS. 5A-5B show that CNS-siRNA$^{ApoE}$ silences ApoE protein in the hippocampus at low doses.
Figure 5B:
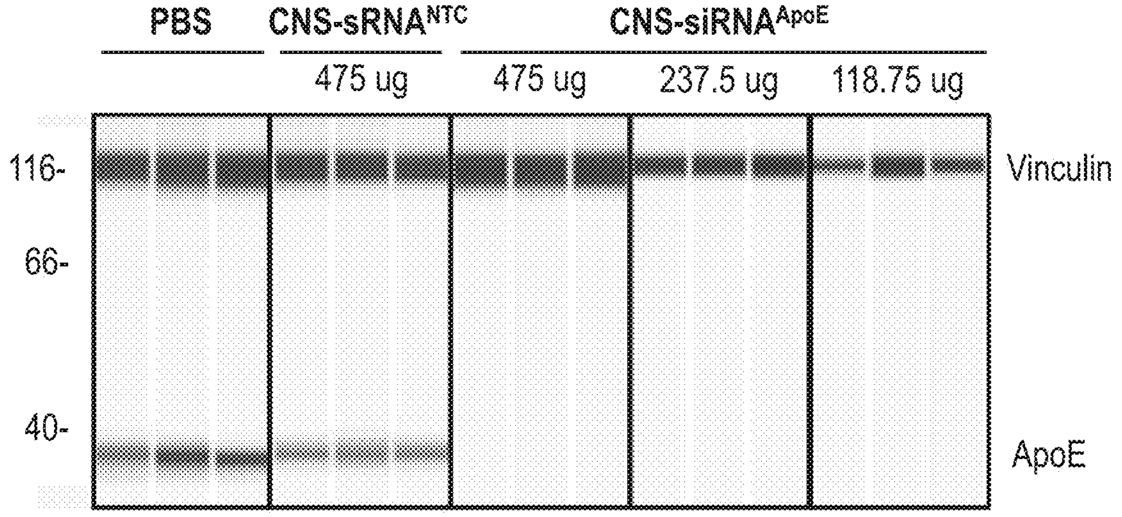

Groups of wild-type mice were administered doses of 475, 237.5, and 118.75 μg of Di-siRNA$^{ApoE}$, respectively. Each group included 3 mice. One month after injection, protein silencing in the hippocampus was quantified and compared to control mice injected with PBS or NTC. As seen in the graph of FIG. 5A and Western blot of FIG. 5B, the novel siRNAs targeting ApoE show protein silencing in vivo at lower doses. Previous reports using oligonucleotides to silence ApoE use sequences that demonstrate an approximately 50% target mRNA and protein silencing after ICV injection of oligonucleotides at a dose of about 400 μg.

2.3 CNS-siRNA$^{ApoE}$ Silences ApoE Throughout the Spinal Cord at Low Doses

Figure 6A:
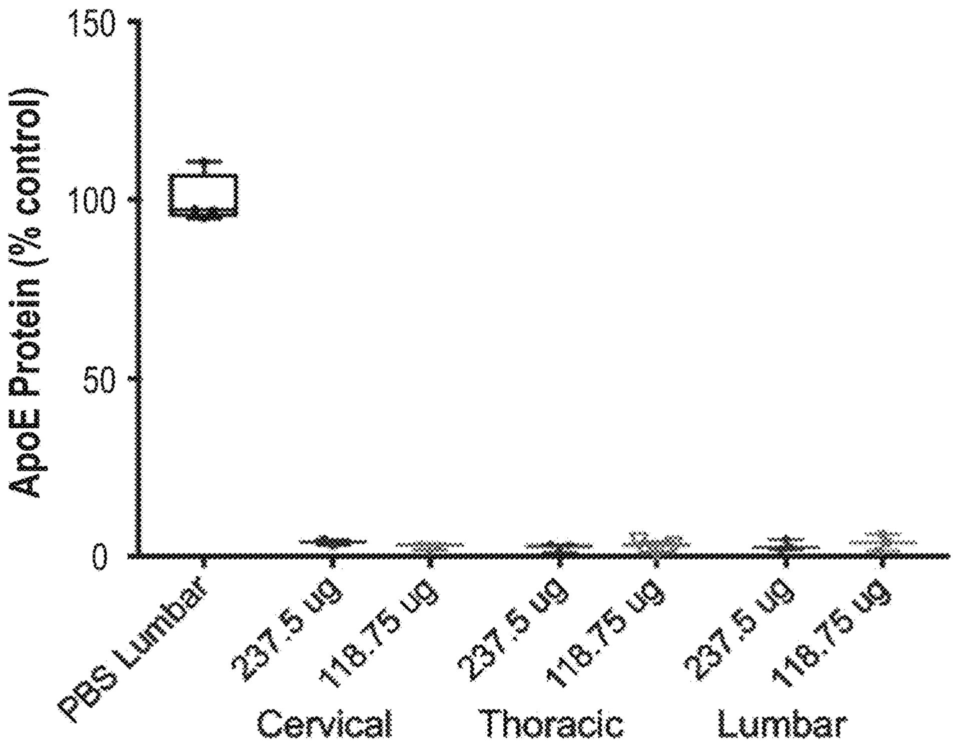
FIGS. 6A-6B show that CNS-siRNA$^{ApoE}$ silences throughout the spinal cord at low doses.
Figure 6B:
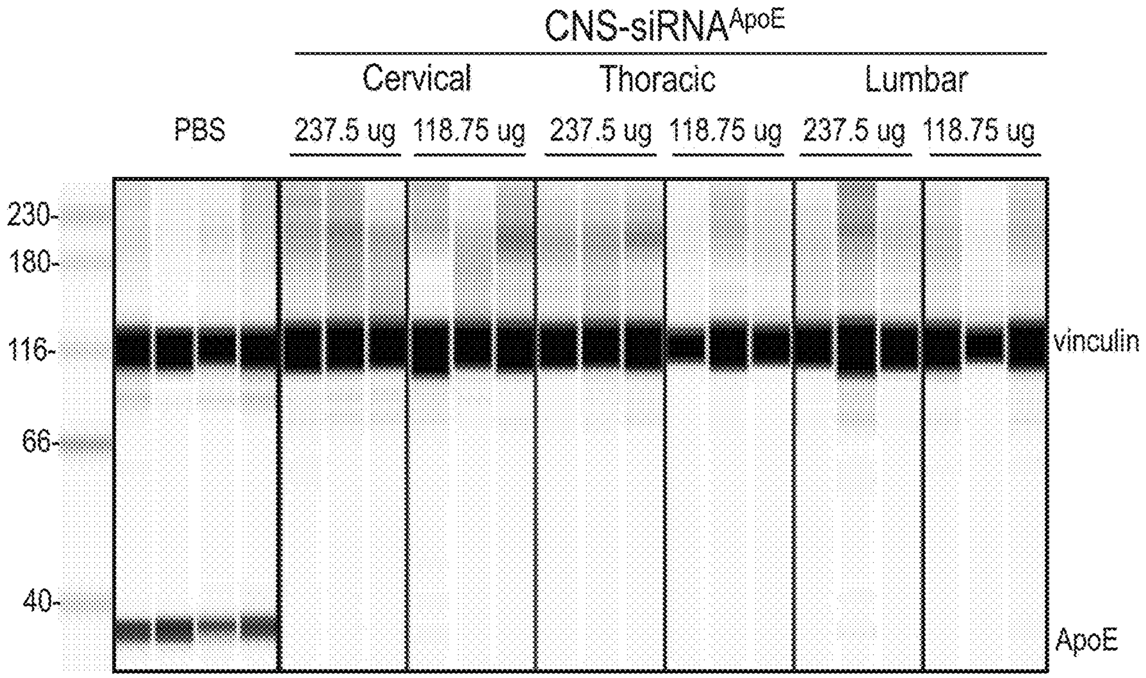

FIG. 6A is a quantification of protein silencing in the spinal cord 1 month post injection. Di-siRNA$^{ApoE}$ doses: 237.5 and 118.75 μg. FIG. 6B is a Western blot (ProteinSimple) showing target ApoE (37 kDa) protein silencing as compared to control vinculin (116 kDa). Following ICV injection, ApoE 1134 silenced protein expression throughout all regions of the spinal cord (Cervical, Thoracic, Lumbar). Previous silencing of ApoE in the spinal cord had not been shown. The ability to silence spinal cord ApoE has many implications for the treatment of spinal cord related neurodegenerative disorders including Amyotrophic Lateral Sclerosis (ALS).

Figure 7A:
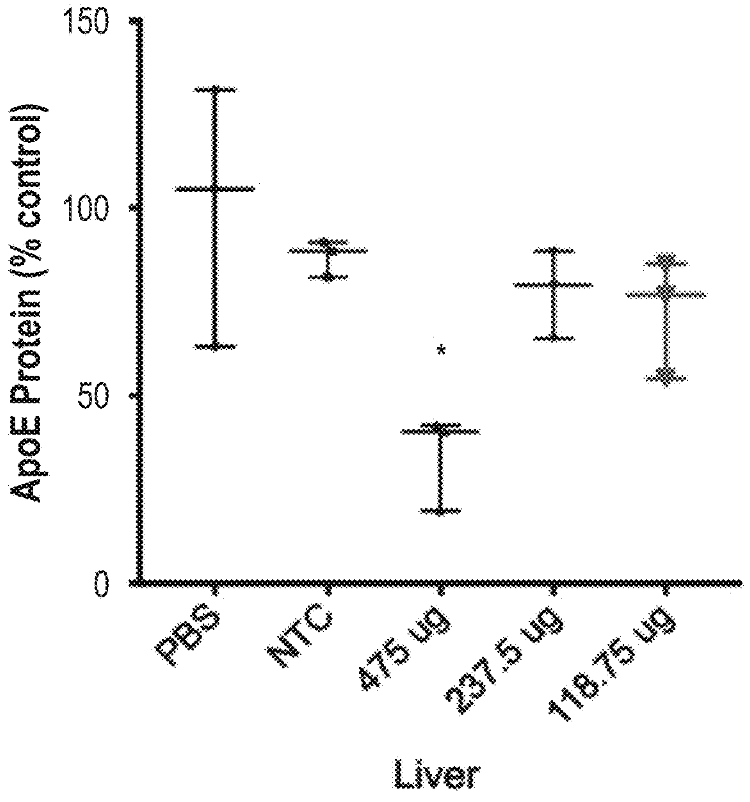
FIGS. 7A-7B show that brain-specific (non-hepatic) silencing of ApoE with CNS-siRNA$^{ApoE}$ is possible at lower doses.
Figure 7B:
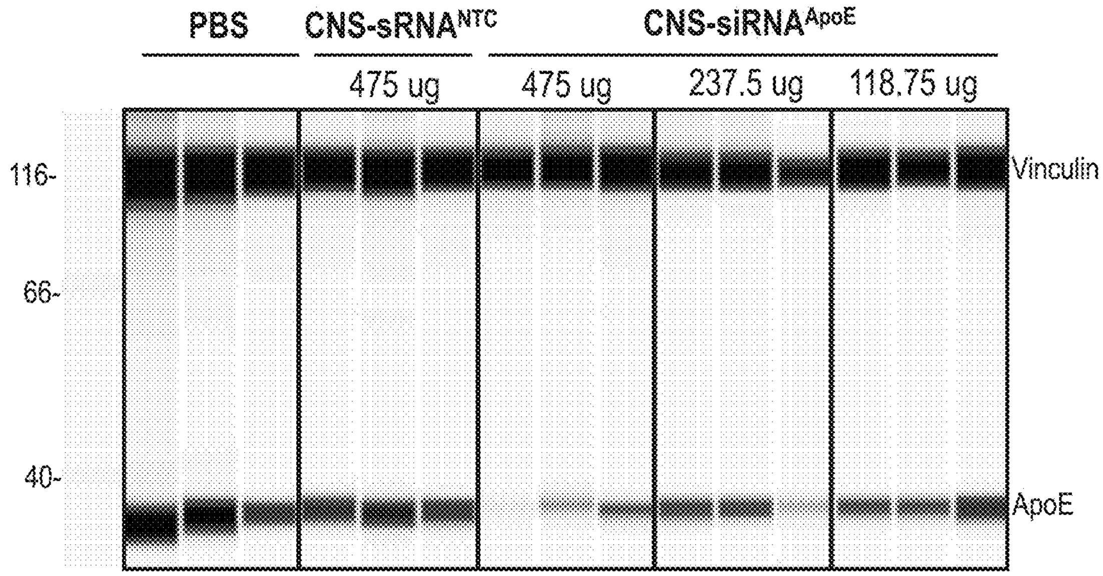

2.4 Brain-Specific (Non-Hepatic) Silencing of ApoE with CNS-siRNA$^{ApoE}$ is Possible at Lower Doses FIG. 7A is a quantification of protein silencing in the liver 1 month post injection. Di-siRNA$^{ApoE}$ doses: 475, 237.5, and 118.75 μg. FIG. 7B is a Western blot (ProteinSimple) showing target ApoE (37 kDa) protein silencing as compared to control vinculin (116 kDa). The dose response to ICV injection of CNS-ApoE showed reduced hepatic protein expression after 475 μg, but no reduction after 237.5 or 118.75 μg. Taken with the silencing data in the brain and spinal cord following the injection of 237.5 and 118.75 μg, this data further suggests that the siRNAs achieve CNS-specific silencing of ApoE. Furthermore, this data also suggests that the two pools of ApoE (CNS and systemic) do not influence each other. Residual hepatic expression does not appear to replenish the silenced CNS (brain or spinal cord) ApoE.

Figure 8A:
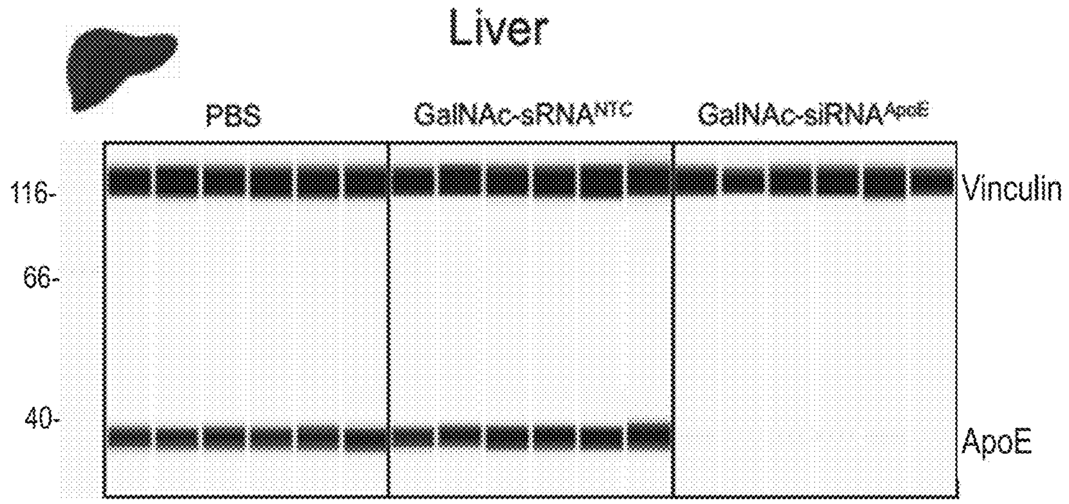
FIGS. 8A-8C show that GalNAc-siRNA$^{ApoE}$ silences protein expression in the liver but has no effect on brain protein.
Figure 8B:
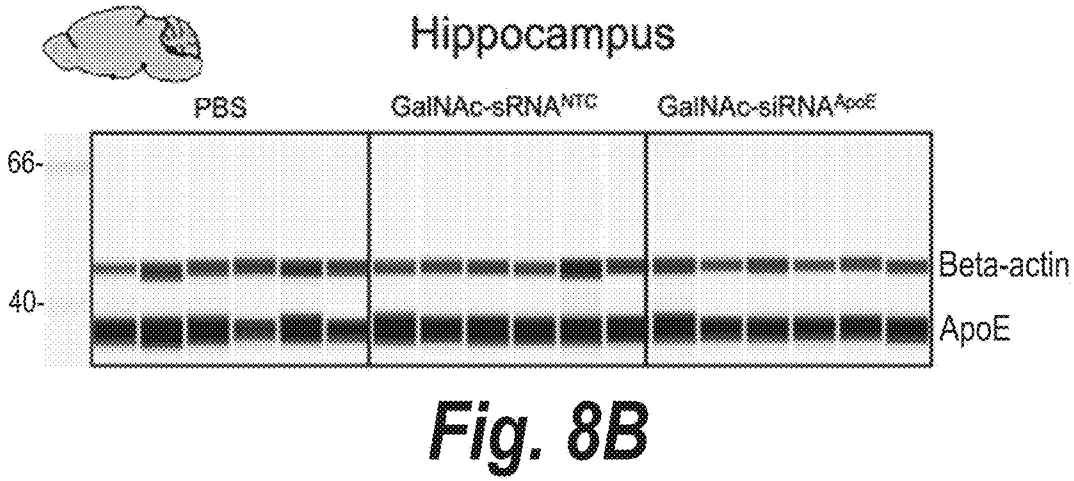
Figure 8C:
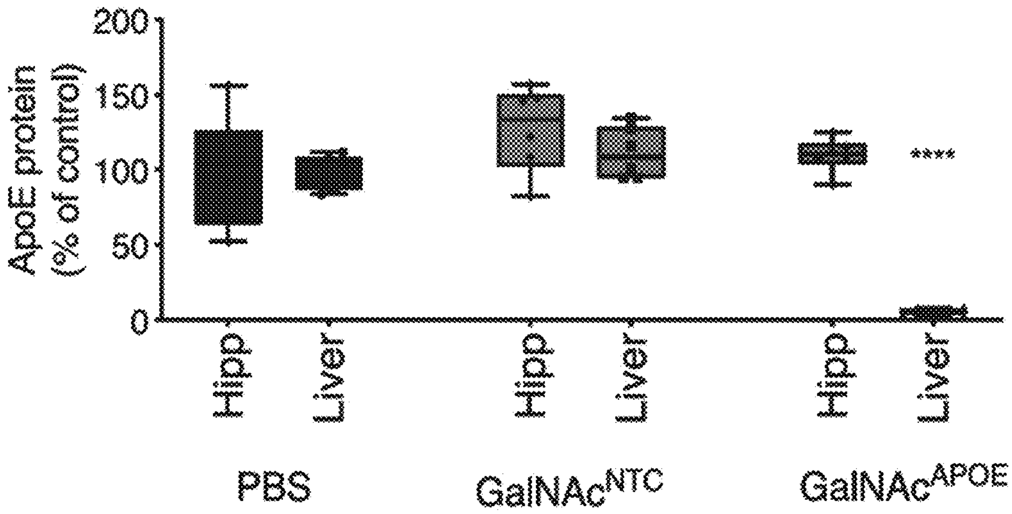

2.5 GalNAc-siRNA$^{ApoE}$ Silences Protein Expression in the Liver but has No Effect on Brain Protein GalNAc conjugates that direct siRNA to hepatocyte liver cells were synthesized and administered to WT mice by subcutaneous injection in the amount of 10 mg/kg. Protein silencing in the liver and hippocampus was quantified 1 month after injection of the GalNAc-siRNA$^{ApoE}$ FIG. 8A is a Western blot (ProteinSimple) showing ApoE protein silencing in the liver vs. control vinculin. FIG. 8B is a Western blot (ProteinSimple) showing no effect on the protein levels in the brain. FIG. 8C is a quantification of protein silencing in the liver and brain. It can be seen that the GalNAc-siRNA$^{ApoE}$ conjugate potently silences hepatic ApoE expression but has no effect on brain ApoE expression. Without being bound to any particular theory, it appears that ApoE produced in the brain does not cross the blood brain barrier and replenish the systemic pool of ApoE even after systemic silencing.

Figure 9A:
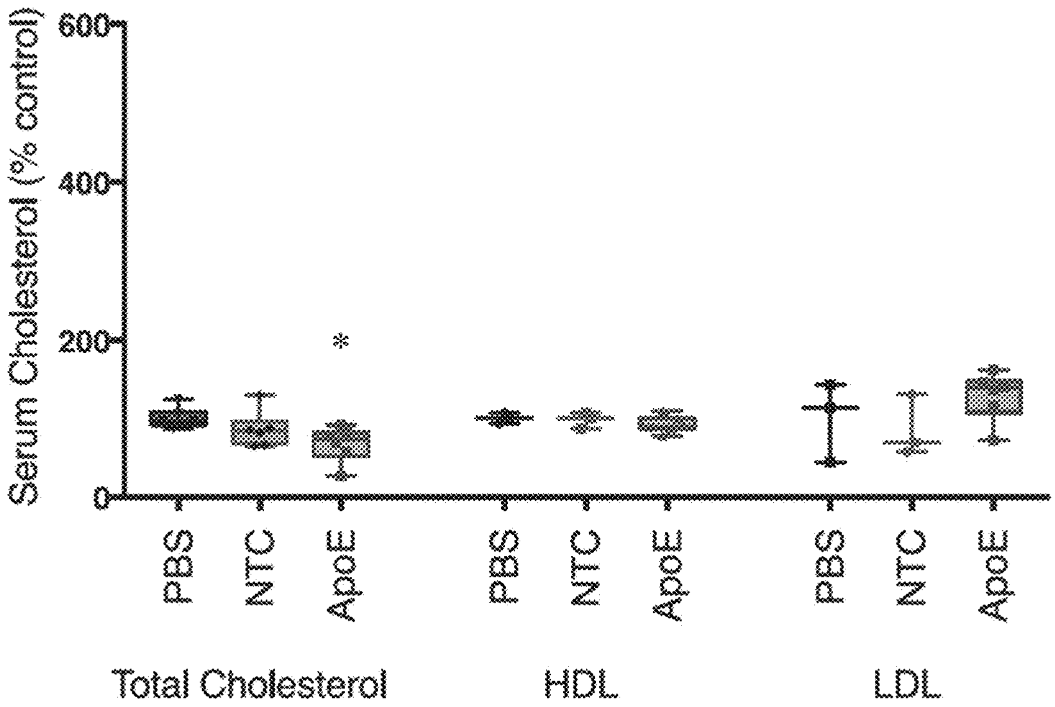
FIGS. 9A-9B show that reducing hepatic ApoE increases serum cholesterol, but silencing only CNS-ApoE does not increase serum cholesterol.
Figure 9B:
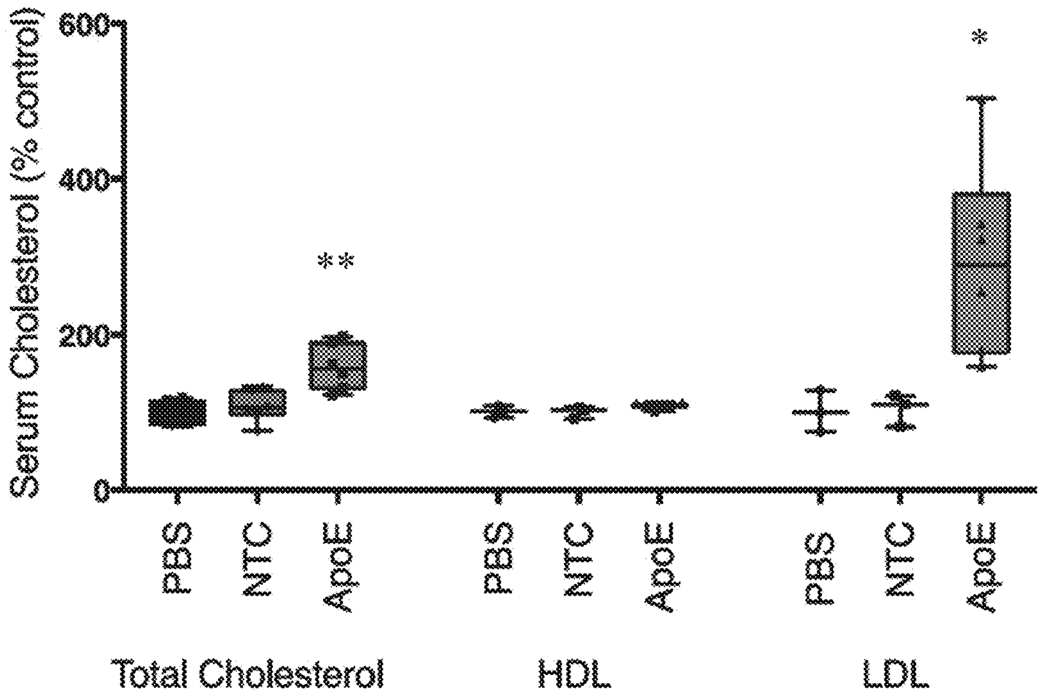

2.6 Reducing Hepatic ApoE Increases Serum Cholesterol, but Silencing Only CNS-ApoE does not Increase Serum Cholesterol A major concern in silencing ApoE as a therapeutic for Alzheimer's disease is the potential effect it could have on systemic cholesterol metabolism. Mice with genetic removal of ApoE develop high systemic cholesterol and aortic atherosclerosis. We show that tissue specific modulation of ApoE in the CNS does not cause an increase in serum cholesterol while systemic modulation causes a significant increase in cholesterol, specifically LDL. This level of discrimination of effects of ApoE silencing on cholesterol has not been previously shown. FIG. 9A depicts a quantification of total serum cholesterol after silencing CNS ApoE. FIG. 9B depicts a quantification of total serum cholesterol after silencing systemic ApoE and a quantification of cholesterol in LDL and HDL fractions after silencing systemic ApoE.

2.7 CNS and Systemic ApoE Represent Two Distinct Pools of Protein

Figure 10A:
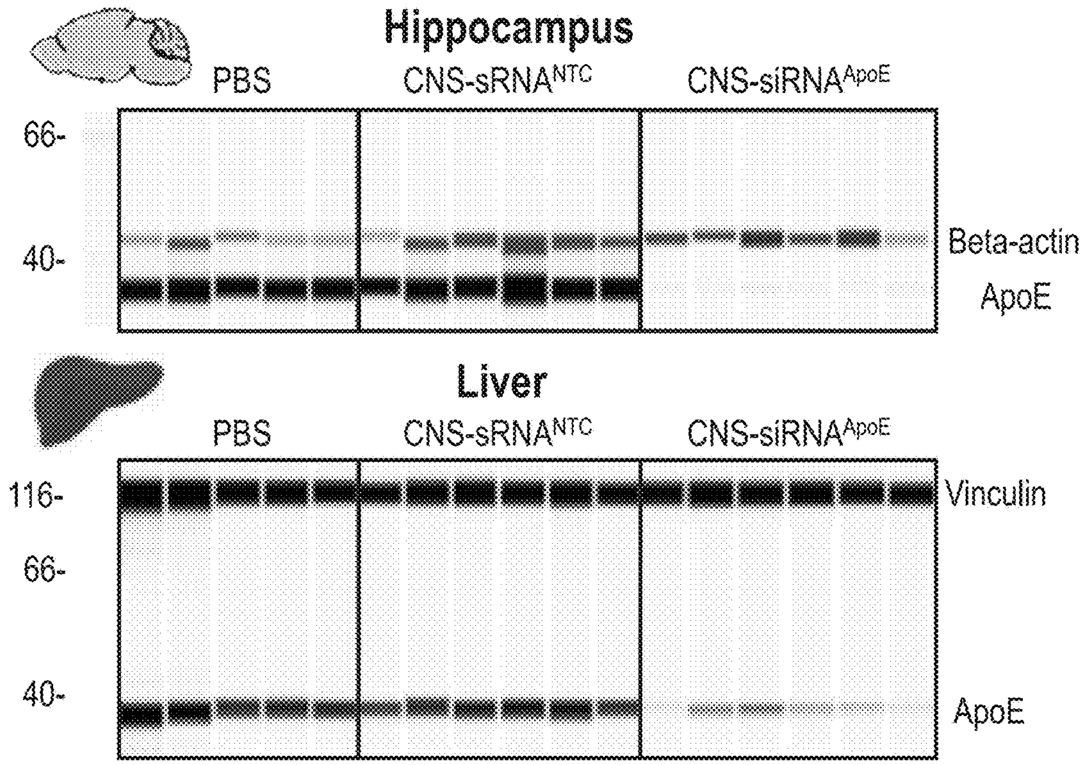
FIGS. 10A-10B show that CNS and systemic ApoE represent two distinct pools of protein.
Figure 10B:
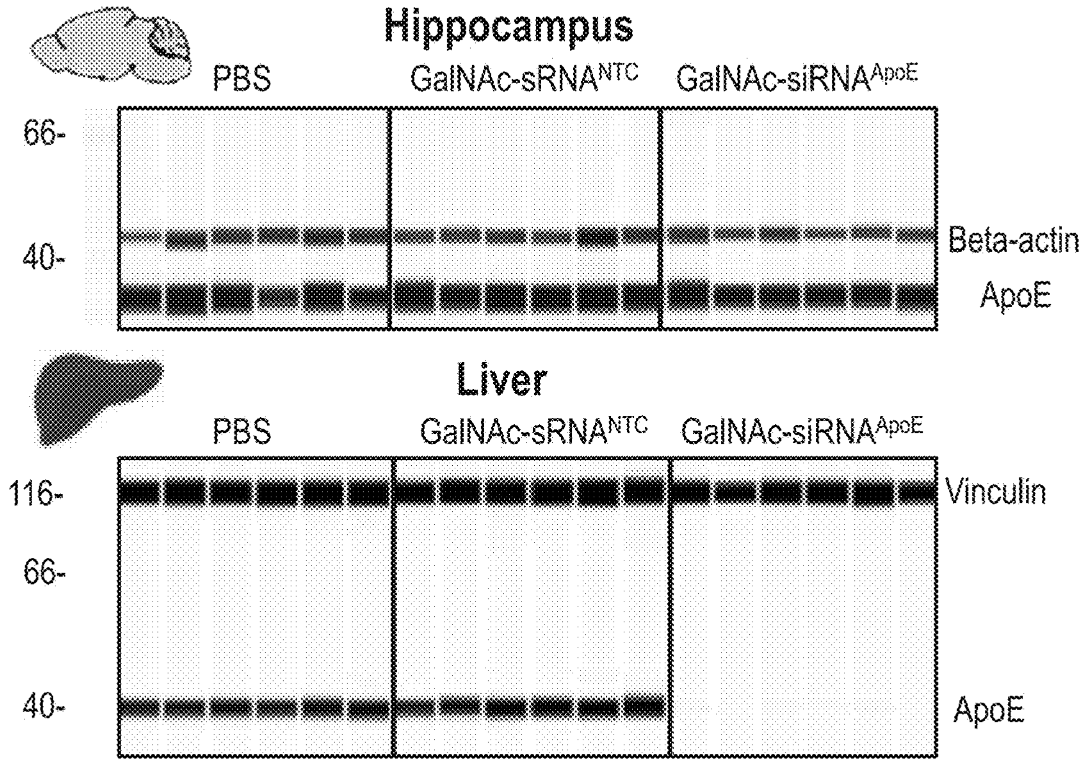

The use of the ApoE sequences of the present application in combination with tissue-specific chemical conjugates provided evidence that two distinct pools of ApoE exist, i.e., CNS ApoE and systemic ApoE. Without being bound to any particular theory, the data suggest that the two pools of ApoE do not interact, do not influence each other's expression, and do not cross the blood brain barrier. This leads us to postulate that one pool of ApoE (CNS or systemic) could be impacting the progression of neuropathology, while the other pool may have little to no effect. FIG. 10A illustrates protein silencing in the brain and liver after injection with CNS-siRNA$^{ApoE}$. FIG. 10B illustrates silencing in the brain (none) and liver after injection with GalNAc-siRNA$^{Ap\ oE}$.

Example 3. Chemical Synthesis of Di-siRNAs and Vitamin D Conjugated hsiRNAs

Figure 12:
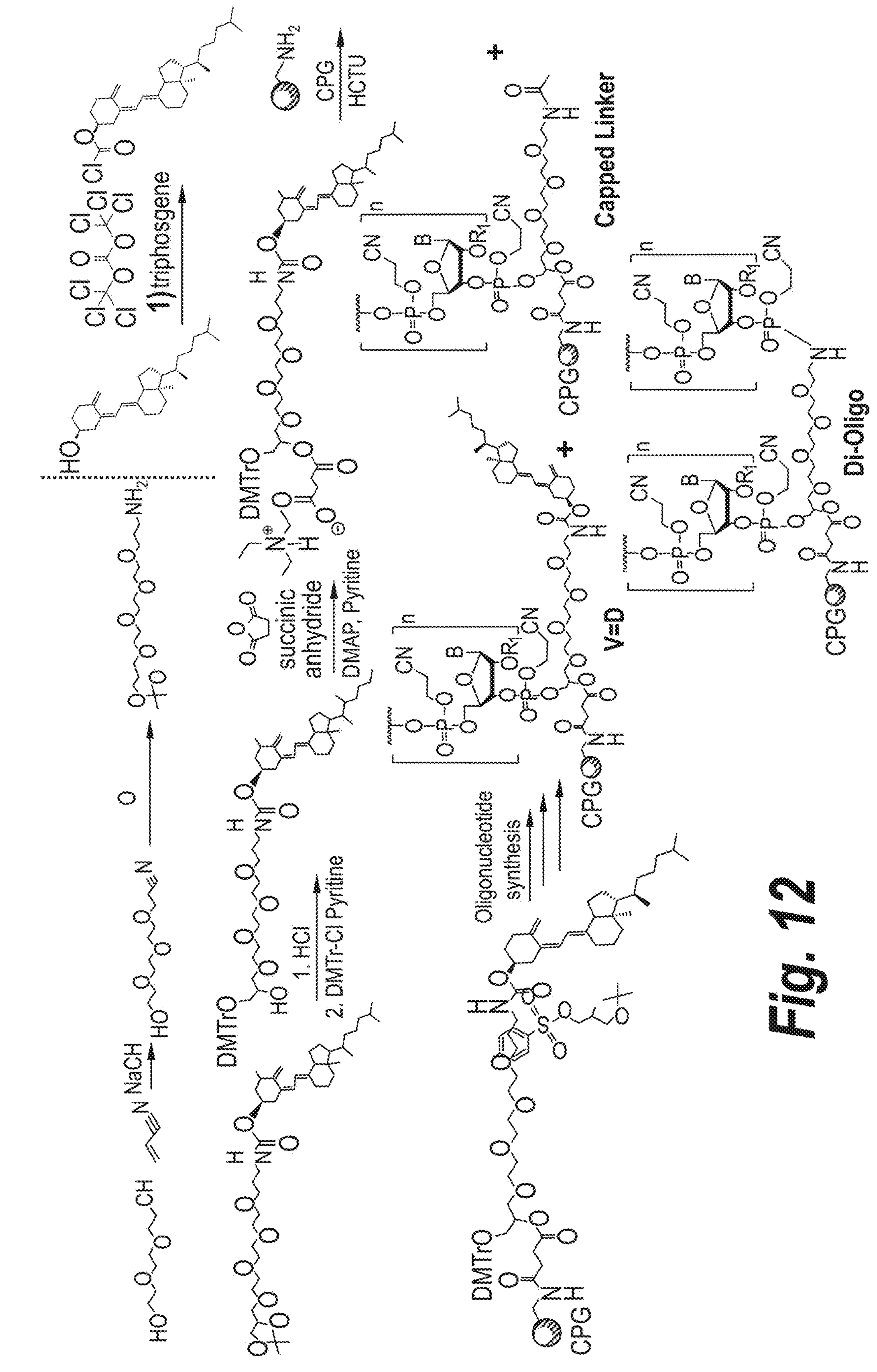
FIG. 12 shows a chemical synthesis, purification and quality control of Di-branched siRNAs.

The Di-siRNAs used in the in vitro and in vivo efficacy evaluation were synthesized as follows. As shown in FIG. 12, triethylene glycol was reacted with acrylonitrile to introduce a protected amine functionality. A branch point was then added as a tosylated solketal, followed by reduction of the nitrile to yield a primary amine which was then attached to vitamin D (calciferol) through a carbamate linker. The ketal was then hydrolyzed to release the cis-diol which was selectively protected at the primary hydroxyl with dimethoxytrityl (DMTr) protecting group, followed by succinylation with succinic anhydride. The resulting moiety was attached to a solid support followed by solid phase oligonucleotide synthesis and deprotection resulting in the three products shown; VitD, Capped linker, and Di-siRNA. The products of synthesis were then analyzed as described in Example 6.

Example 4. Alternative Synthesis Route 1

Figure 15A:
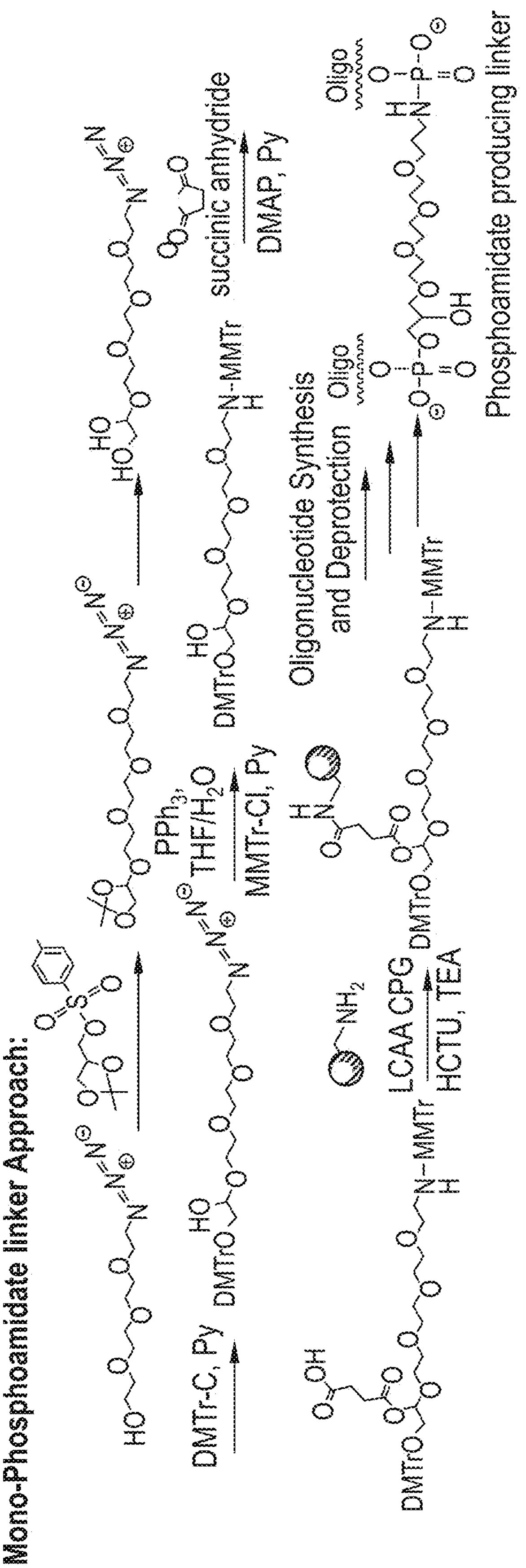
FIGS. 15A-15B show a synthesis of a branched oligonucleotide using alternative chemical routes.

As shown in FIG. 15A, the mono-phosphoamidate linker approach involves the following steps: Mono-azide tetraethylene glycol has a branch point added as a tosylated solketal. The ketal is then removed to release the cis-diol which is selectively protected at the primary hydroxyl with dimethoxytrityl (DMTr) protecting group, followed by reduction of the azide by triphenylphosphine to a primary amine, which is immediately protected with a monomethoxy trityl (MMTr) protecting group. The remaining hydroxyl is succinylated with succinic anhydride and coupled to solid support (LCAA CPG). Oligonucleotide synthesis and deprotection affords one main product the, the di-siRNA with a phosphate and phosphoamidate linkage. This example highlights an alternative and direct route of synthesis to produce solely the phosphate and phosphoamidate linker.

Example 5. Alternative Synthesis Route 2

Figure 15B:
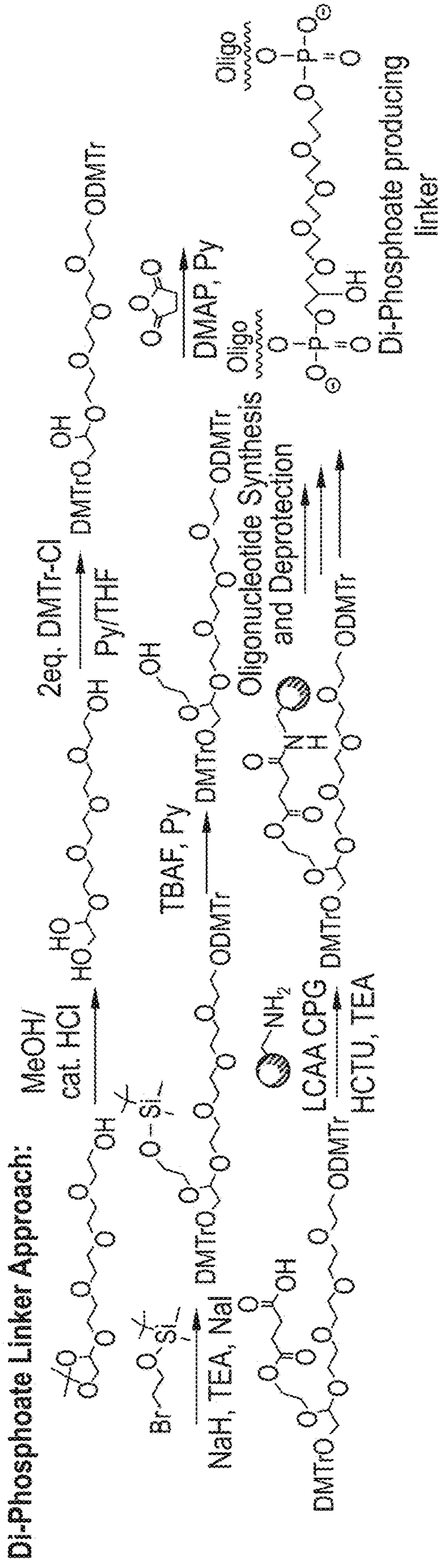

In order to produce a di-phosphate containing moiety, a second alternative synthesis approach was developed. As shown in FIG. 15B, the di-phosphoate linker approach involves the following steps: Starting from a solketal-modified teraethylene glycol, the ketal is removed and the two primary hydroxyls are selectively protected with dimethoxy trityl (DMTr). The remaining hydroxyl is extended in length with a silyl protected 1-bromoethanol. The TBDMS is removed, succinylated and attached to solid support. This is followed by solid phase oligonucleotide synthesis and deprotection, producing the Di-siRNA with the diphosphate containing linker.

Example 6. Quality Control of Chemical Synthesis of Di-siRNAs and Vitamin D Conjugated hsiRNAs

HPLC

Figure 13:
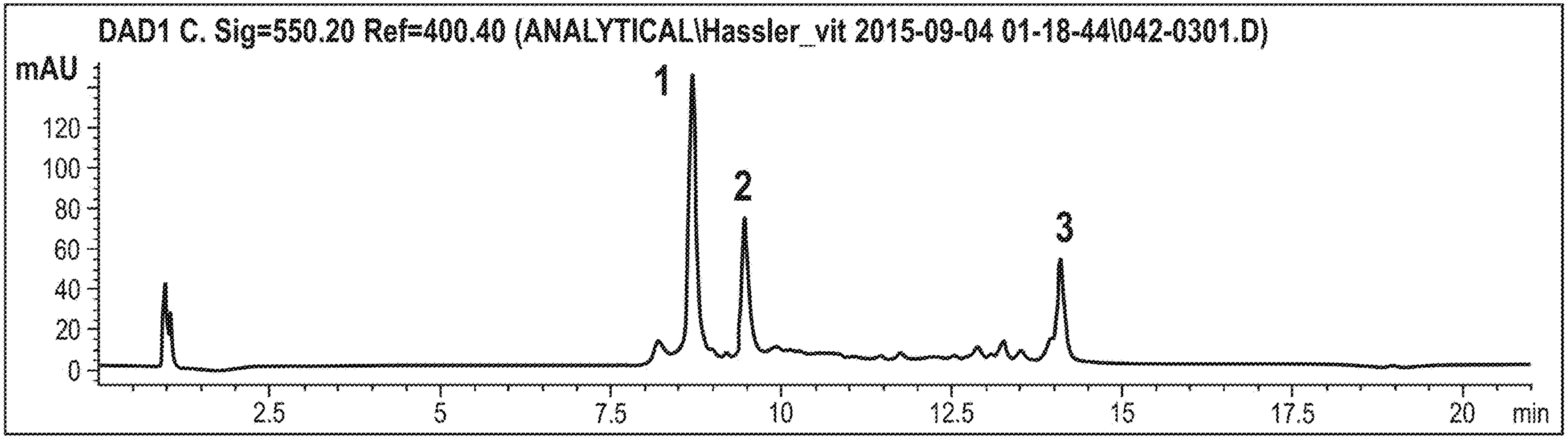
FIG. 13 shows HPLC and quality control of compounds produced by the method depicted in FIG. Three major products were identified by mass spectrometry as sense strand with TEG (tetraethylene glycol) linker, di-branched oligo and Vit-D (calciferol) conjugate. All products where purified by HPLC and tested in vivo independently. Only Di-branched oligo is characterized by unprecedented tissue distribution and efficacy, indicating that branching structure is essential for tissue retention and distribution.
Figure 13:
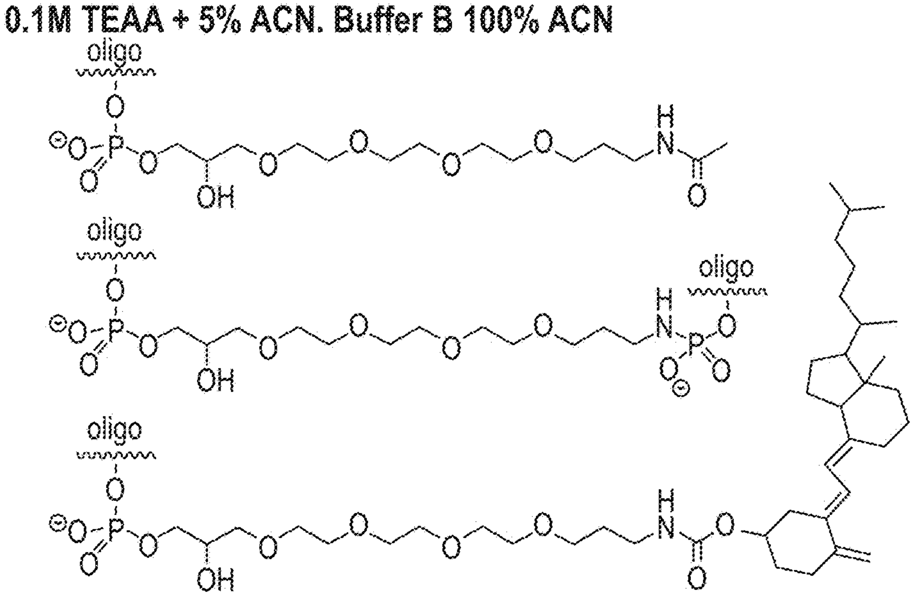

To assess the quality of the chemical synthesis of Di-siRNAs and Vitamin D conjugated hsiRNAs, analytical HPLC was used to identify and quantify the synthesized products. Three major products were identified: the siRNA sense strand capped with a tryethylene glycol (TEG) linker, the Di-siRNA, and the vitamin D conjugated siRNA sense strand (FIG. 13). Each product was isolated by HPLC and used for subsequent experiments. The chemical structures of the three major products of synthesis are shown in FIG. 13. The conditions for HPLC included: 5-80% B over 15 minutes, Buffer A (0.1M TEAA+5% ACN), Buffer B (100% ACN).

Mass Spectrometry

Figure 14:
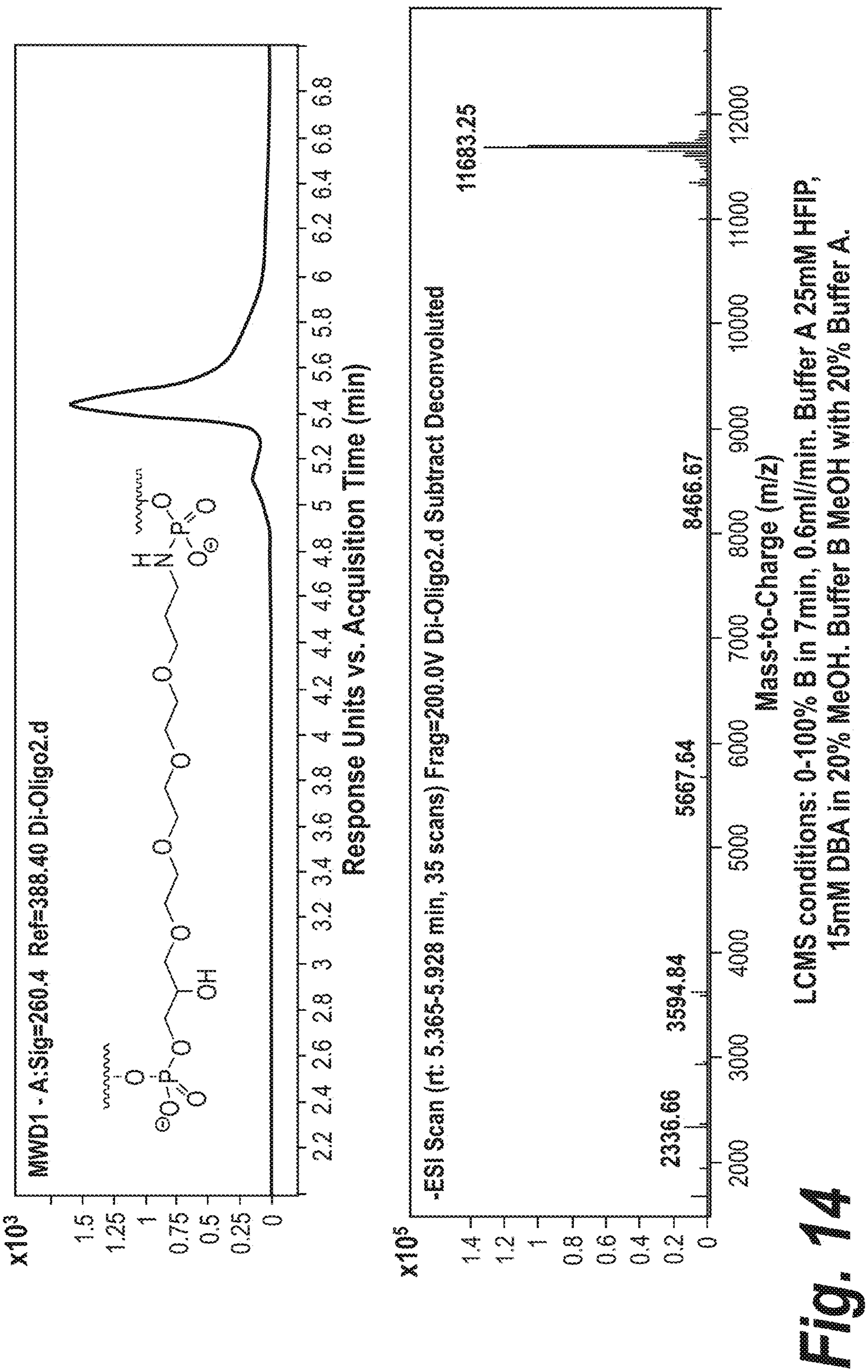
FIG. 14 shows mass spectrometry confirming the mass of the Di-branched oligonucleotide. The observed mass of 11683 corresponds to two sense strands attached through the TEG linker by the 3' ends.

Further quality control was done by mass spectrometry, which confirmed the identity of the Di-siRNA complex. The product was observed to have a mass of 11683 m/z, which corresponds to two sense strands of the siRNA attached at the 3' ends through the TEG linker (FIG. 14). In this specific example the siRNA sense strand was designed to target the Huntingtin gene (Htt). The method of chemical synthesis outlined in Example 5 successfully produced the desired product of a Di-branched siRNA complex targeting the Huntingtin gene. LC-MS conditions included: 0-100% B over 7 minutes, 0.6 mL/min. Buffer A (25 mM HFIP, 15 mM DBA in 20% MeOH), Buffer B (MeOH with 20% Buffer A).

Example 7. Incorporation of a Hydrophobic Moiety in the Branched Oligonucleotide Structure: Strategy 1

Figure 29:
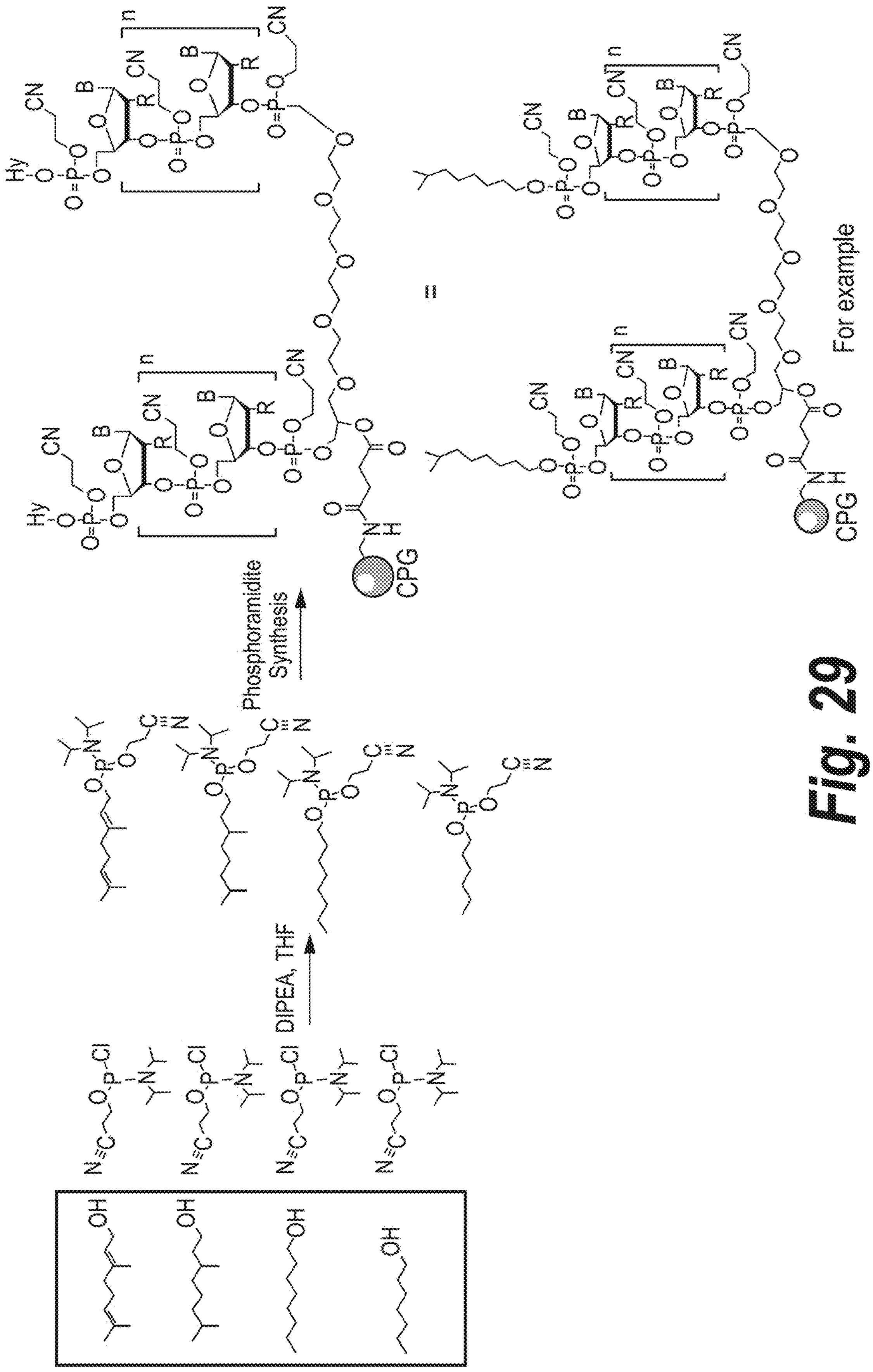
FIG. 29 depicts a first strategy for the incorporation of a hydrophobic moiety into the branched oligonucleotide structures.

In one example, a short hydrophobic alkylene or alkane (Hy) with an unprotected hydroxyl group (or amine) that can be phosphitylated with 2-Cyanoethoxy-bis(N,N-diisopropylamino)phosphine (or any other suitable phosphitylating reagent) is used to produce the corresponding lipophilic phosphoramidite. These lipophilic phosphoramidites can be added to the terminal position of the branched oligonucleotide using conventional oligonucleotide synthesis conditions. This strategy is depicted in FIG. 29.

Example 8. Incorporation of a Hydrophobic Moiety in the Branched Oligonucleotide Structure: Strategy 2

Figure 30:
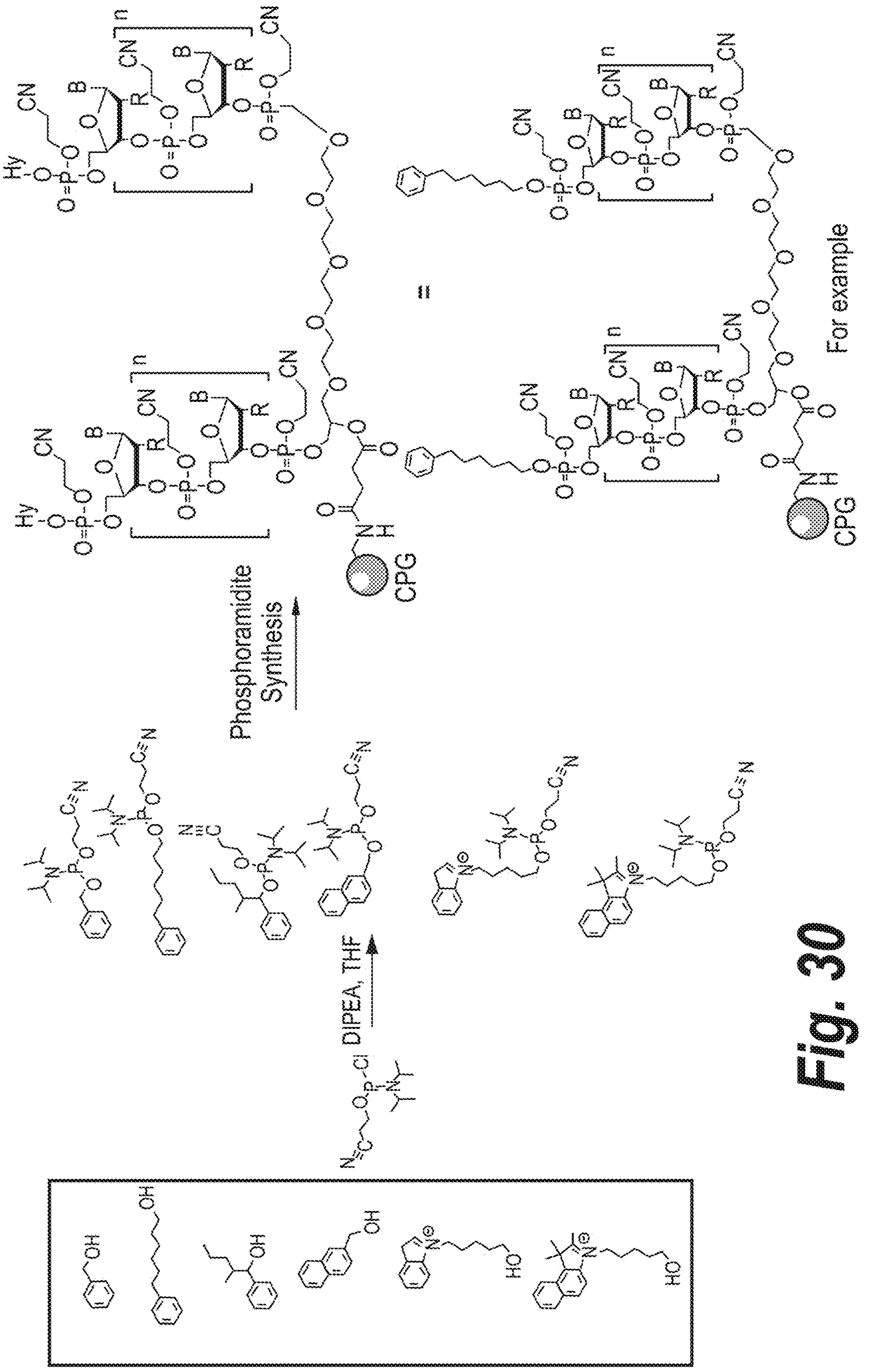
FIG. 30 depicts a second strategy for the incorporation of a hydrophobic moiety into the branched oligonucleotide structures.

In another example, a short/small aromatic planar molecule (Hy) that has an unprotected hydroxyl group with or without a positive charge (or amine) that can be phosphitylated with 2-Cyanoethoxy-bis(N,N-diisopropylamino)phosphine (or any other suitable phosphitylating reagent) is used to produce the corresponding aromatic hydrophobic phosphoramidite. The aromatic moiety can have a positive charge. These lipophilic phosphoramidites can be added to the terminal position of the branched oligonucleotide using conventional oligonucleotide synthesis conditions. This strategy is depicted in FIG. 30.

Example 9. Incorporation of a Hydrophobic Moiety in the Branched Oligonucleotide Structure: Strategy 3

Figure 31:
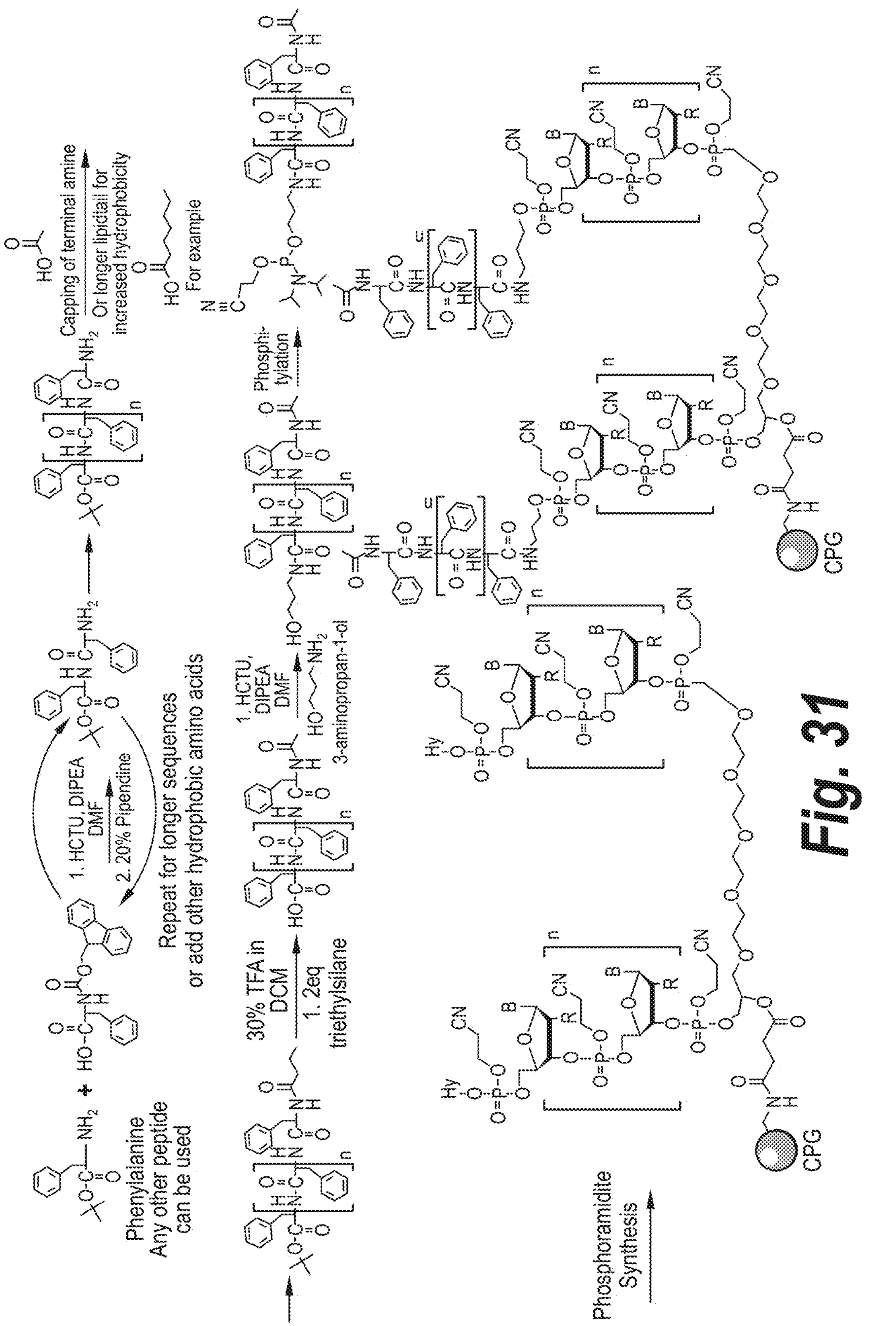
FIG. 31 depicts a third strategy for the incorporation of a hydrophobic moiety into the branched oligonucleotide structures.
Figure 32:
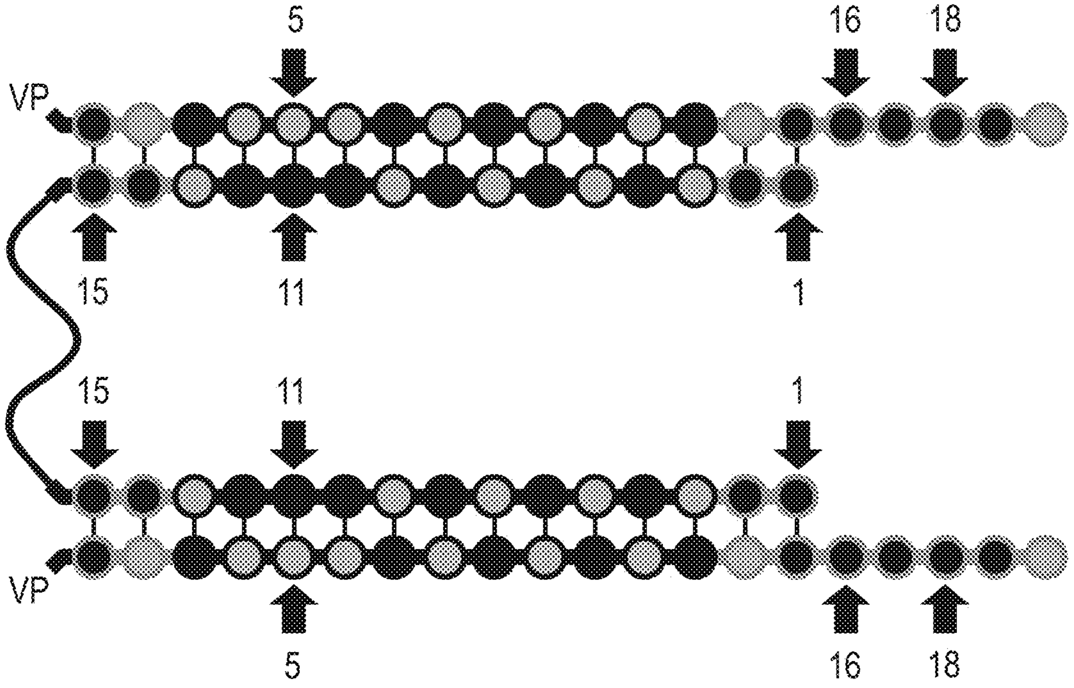
FIG. 32 depicts a schematic of a Di-siRNA molecule. Black—2-O-methyl, grey—2'-fluoro, red dash—phosphorothioate bond, linker attached to terminal nucleotide of 3'end of each passenger strand. The motif of alternating nucleotide modifications varies at positions 1, 11 and 15 of the sense targeting strand from the 5' end and at positions 5, 16, and 18 of the complimentary, linked strands from the 5'end.
Figure 33:
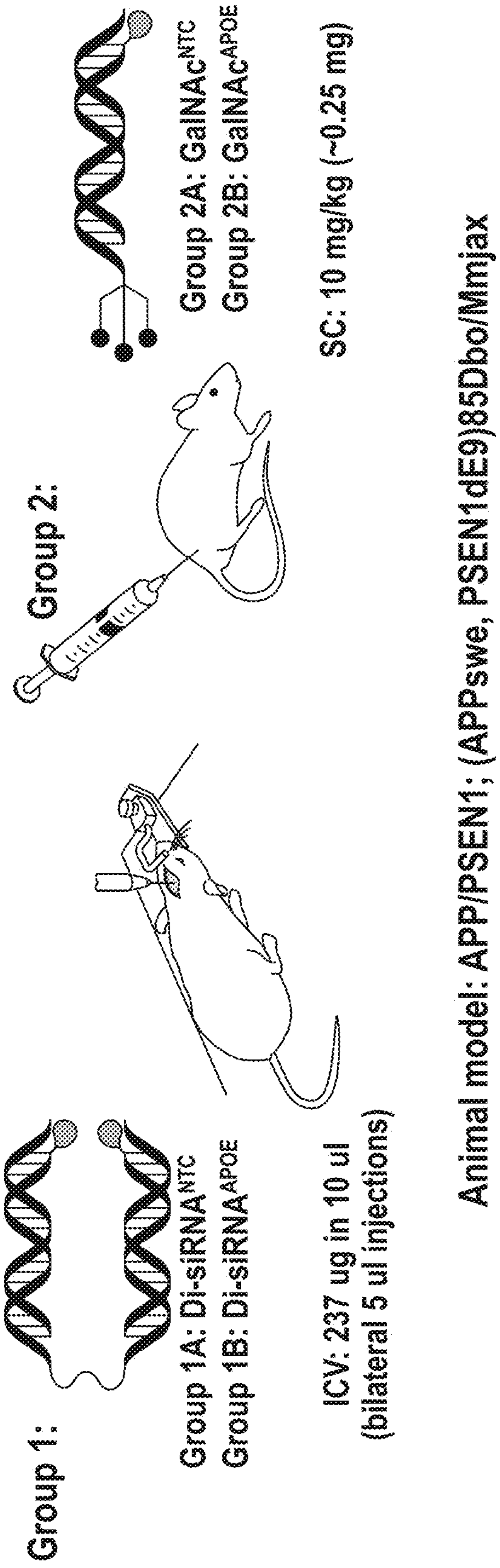
FIG. 33 illustrates the experimental design of a study for evaluating the effects of ApoE silencing on neurodegenerative diseases.

To introduce biologically relevant hydrophobic moieties, short lipophilic peptides are made by sequential peptide synthesis either on solid support or in solution (the latter being described here). The short (1-10) amino acid chain can contain positively charged or polar amino acid moieties as well, as any positive charge will reduce the overall net charge of the oligonucleotide, therefore increasing the hydrophobicity. Once the peptide of appropriate length is made it should be capped with acetic anhydride or another short aliphatic acid to increase hydrophobicity and mask the free amine. The carbonyl protecting group is then removed to allow for 3-aminopropan-1-ol to be coupled allowing a free hydroxyl (or amine) to be phosphitylated. This amino acid phosphoramidite can then be added to the terminal 5' position of the branched oligonucleotide using conventional oligonucleotide synthesis conditions. This strategy is depicted in FIG. 31.

Example 10. Silencing ApoE in Neurodegeneration

Outlined in Table 6 are a number of transgenic mouse models mimicking a range of Alzheimer's disease-related pathologies. Although none of the models fully replicates the human disease, the models have contributed significant insights into the pathophysiology of beta-amyloid toxicity:

TABLE 6

| Model | Mutations | Pathology | Citation |
|---|---|---|---|
| 2xAD (APPPS1) | Transgenic APP (Swe), PSEN1 (M146) | Aβ deposition (4 months). Cognitive defects. | Garcia-Alloza et al. Neurobiol Dis. 2006 Dec.; 24(3): 516-24. |
| 3xAD +/− hApoE4 | APP (Swe); PSEN1 (M146); MAPT (P301L) | Aβ deposition (6-12 months). Synaptic dysfunction. Tau pathology (6 months. | Oddo et al. J Biol Chem. 2006 Dec. 22; 281(51): 39413-23. |
| 5xFAD | APP (Swedish); APP (Florida); APP (London); PSEN1 (M146L); PSEN1 | Aβ deposition (2 months). Gliosis. Neuronal loss. | Oakley et al. J Neurosci. 2006 Oct. 4; 26(40): 10129-40. |
| hApoE 2, 3, 4 | Knock in of human gene | Altered lipid metabolism. Tau hyper-phosphorylation. Worse response to injury. | Mann et al. Hum Mol Genet. 2004 Sept. 1; 13(17): 1959-68. |

To evaluate the effects of ApoE silencing on neurodegenerative diseases, APP/PSEN1 mice were injected with Di-siRNA$^{ApoE}$ or Di-siRNA$^{NTC}$ by ICV at 8 weeks old (n=5 females and 5 males per group). A second group (n=7 per group) were injected with GalNAC$^{ApoE}$ and GalNAC$^{NTC}$ subcutaneously at 8 weeks old. Animals were euthanized 2 months post injection at 4 months old. Four deaths were observed in the Di-siRNA$^{NTC}$ female group, 1 death in the Di-siRNA$^{ApoE}$ female group, 1 death in the Di-siRNA$^{NTC}$ male group and 1 death in the Di-siRNA$^{ApoE}$ male group. Three deaths were observed in the GalNAC$^{NTC}$ group and 1 death in the GalNAC$^{ApoE}$ group. All deaths were due to natural causes of the animal model pathology and occurred at least 1 month post injection.

Figure 34:
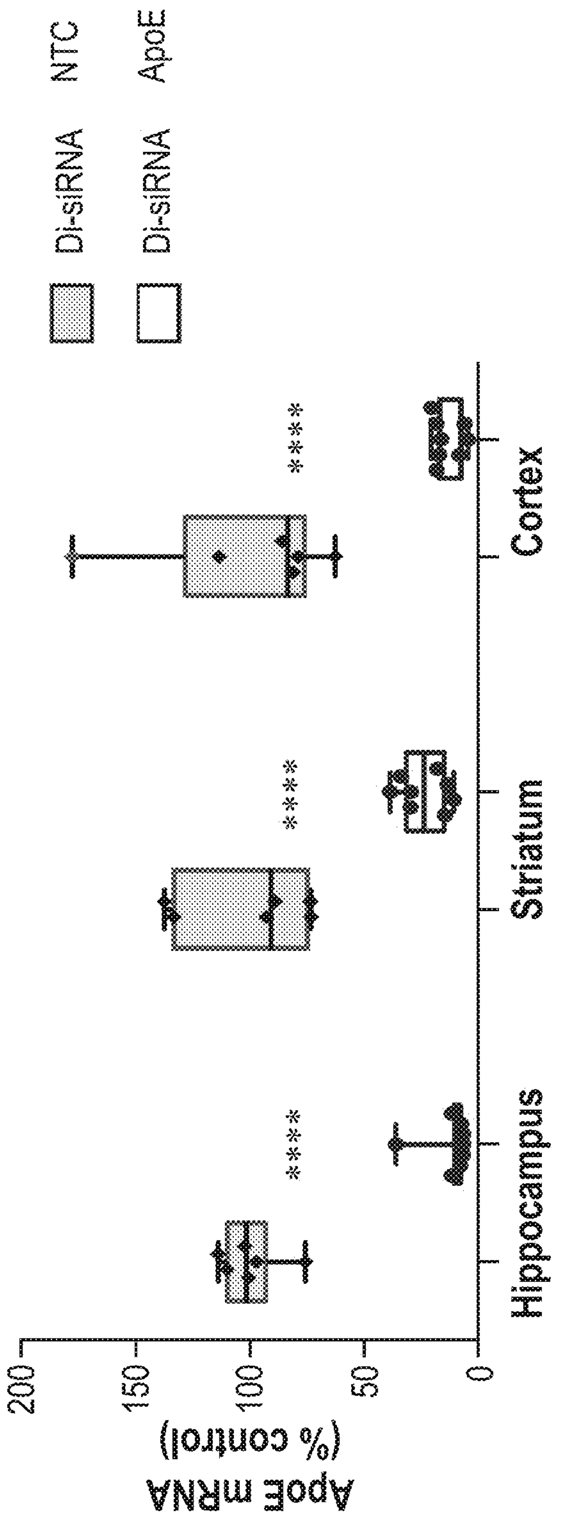
FIG. 34 is a graph illustrating the mRNA silencing effect of siRNAs targeting ApoE 2-months post injection in animal models of Alzheimer's disease (APP/PSEN1).

FIG. 34 is a graph reporting mRNA silencing in all regions of the brain 2 month post injection in APP/PSEN1

Figure 35:
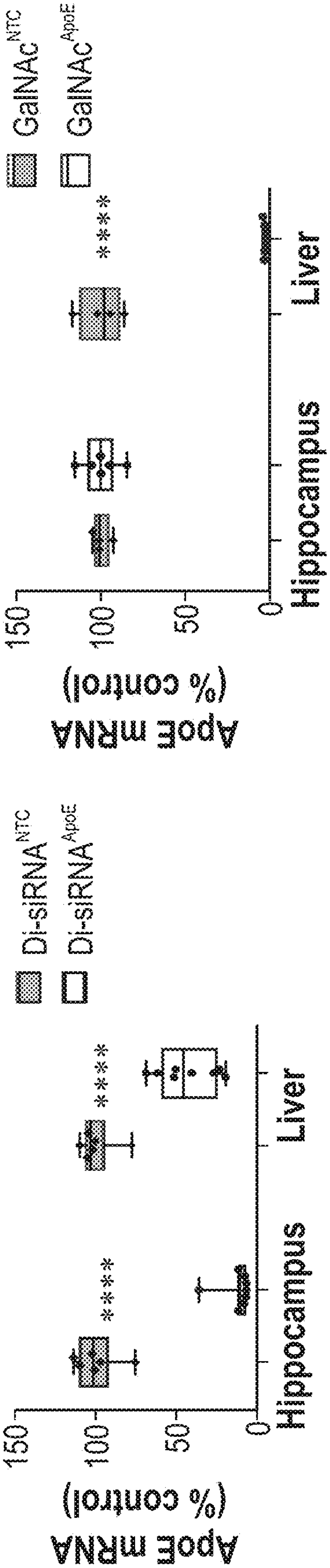
FIGS. 35A-35B include graphs illustrating the effects of tissue-specific siRNAs targeting ApoE 2-months post injection in animal models of Alzheimer's disease (APP/PSEN1).
Figure 36:
FIGS. 36A-36B include graphs illustrating tissue-specific protein silencing 2-months post-injection in animal models of Alzheimer's disease.
Figure 37:
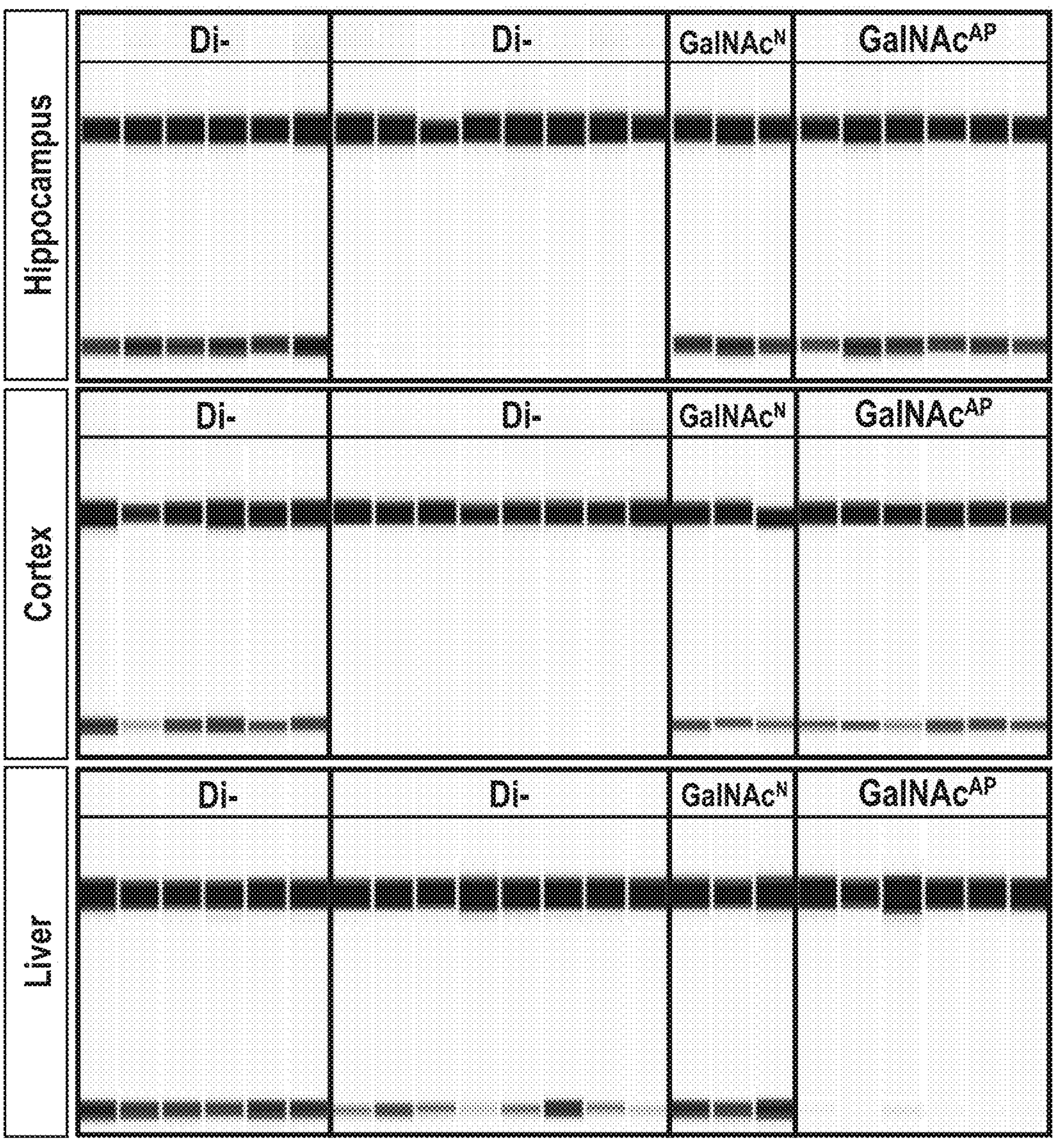
FIG. 37 includes raw western blots showing ApoE protein expression in the hippocampus, cortex, and liver after ICV or SC injection with Di-siRNA$^{NTC}$, DI-siRNA$^{ApoE}$, GalNAc$^{NTC}$, or GalNAc$^{APOE}$.

AD mice (n=2-5 females and 5 males per group; 237 μg/injection). Potent silencing was also observed in all regions of the brain. These results demonstrate that the nucleic acids of the present application offer a significant advantage in studying the role of ApoE in neurodegeneration. As illustrated in the graphs of FIG. 35, the novel siRNAs targeting either brain (Di-siRNA$^{ApoE}$) or liver (GalNAc-siRNA$^{ApoE}$) ApoE show potent and target-specific mRNA silencing in target tissues 2-months post ICV injection. Potent and target-specific protein silencing was also observed (FIG. 36). The raw western blots of FIG. 37 show ApoE protein expression in the hippocampus, cortex, and liver after ICV or SC injection with Di-siRNA$^{NTC}$, Di-siRNA$^{ApoE}$, GalNAc$^{NTC}$, or GalNAc$^{ApoE}$.

The loss of second band which represents ApoE protein indicates potent silencing compared to the NTC control groups. Taken together, the evidence shoes that two distinct pools of ApoE exist, CNS ApoE and systemic ApoE, in the APP/PSEN1 model of Alzheimer's disease. The data suggest that the two pools of ApoE do not interact, do not influence each other's expression, and do not cross the blood brain barrier. This data supports the postulate that one pool of ApoE (CNS or systemic) could be impacting the progression of neuropathology, while the other pool may have little to no effect.

Figure 38:
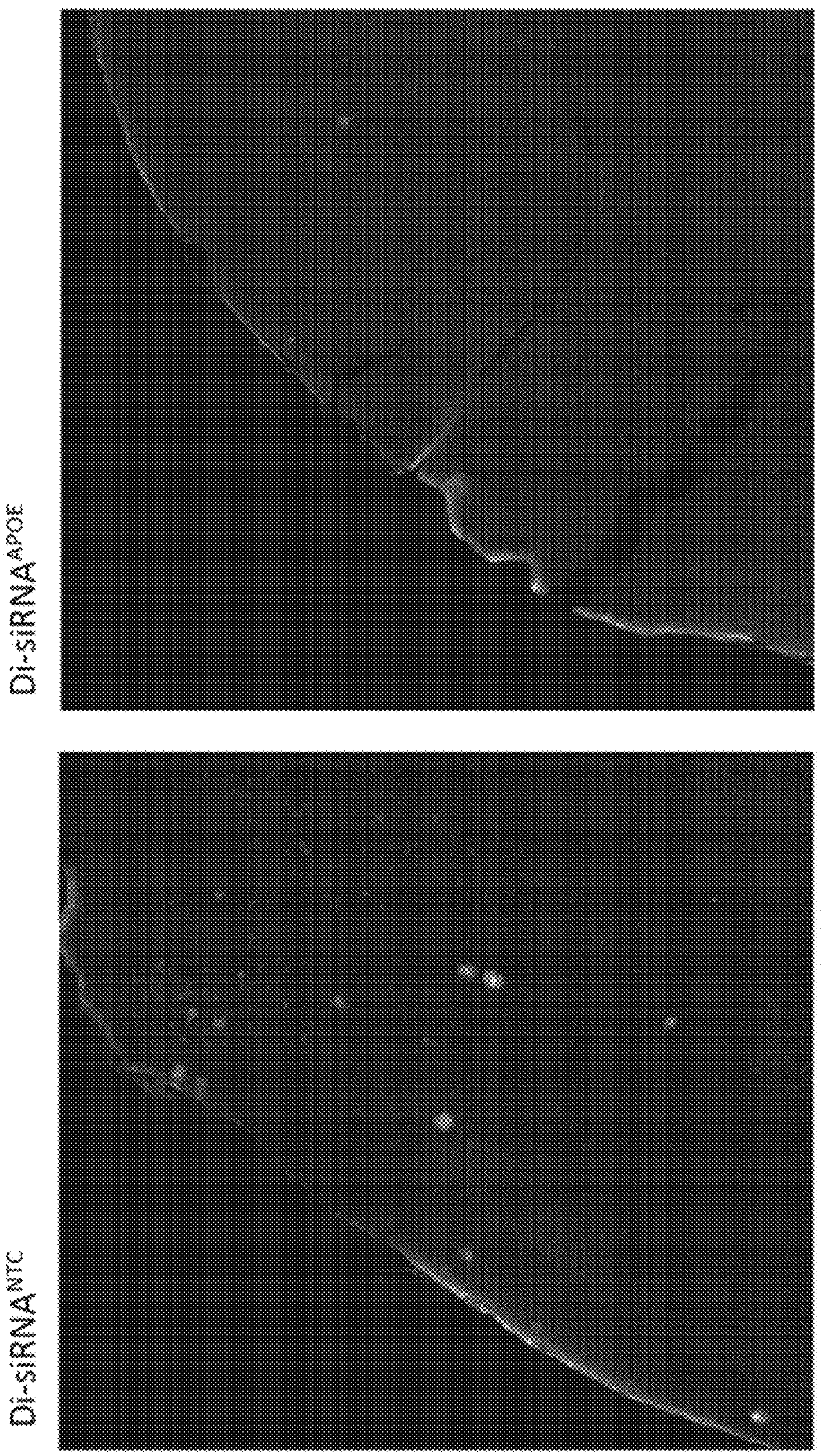
FIG. 38 includes immunofluorescence microscopic images of brain cortex sections from mice treated with either Di-siRNA$^{NTC}$ or Di-siRNA$^{ApoE}$.
Figure 39:
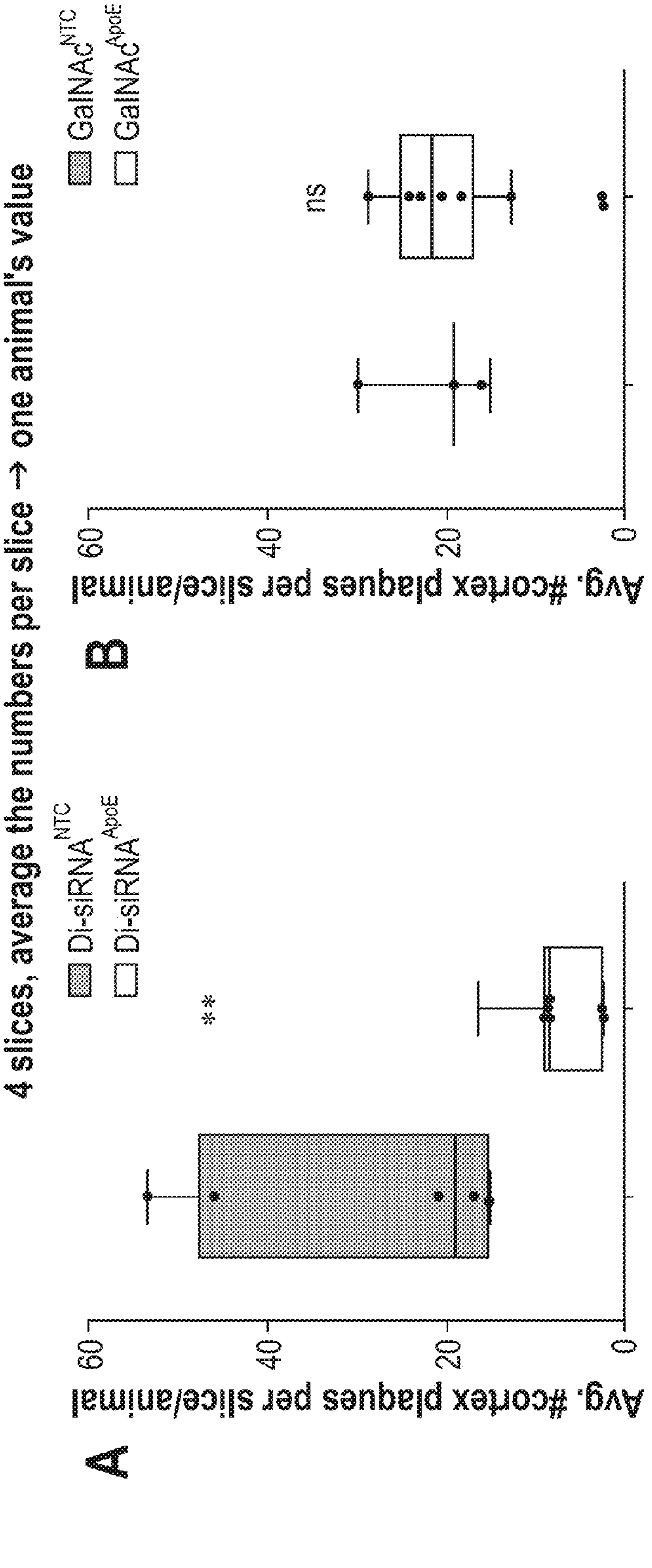
FIGS. 39A-39B include graphs reporting average numbers of cortex plaques as measured in animals treated with Di-siRNA$^{APoE}$ and GalNAc-siRNA$^{ApoE}$.

Brain cortex tissue slices 40 μm in thickness (4 per animal) were stained using standard immunofluorescence protocol with anti-APP 6E10 and anti-Lamp1 antibodies. Tiled images (10×) were taken on Leica microscope. As seen in FIG. 38, a visual reduction in beta-amyloid and Lamp1 positive plaques was observed in Di-siRNA$^{ApoE}$ treated animals as compared to those treated with Di-siRNA$^{NTC}$. This reduction was statistically significant, as may be seen in the graphs of FIG. 39.

Figure 40A:
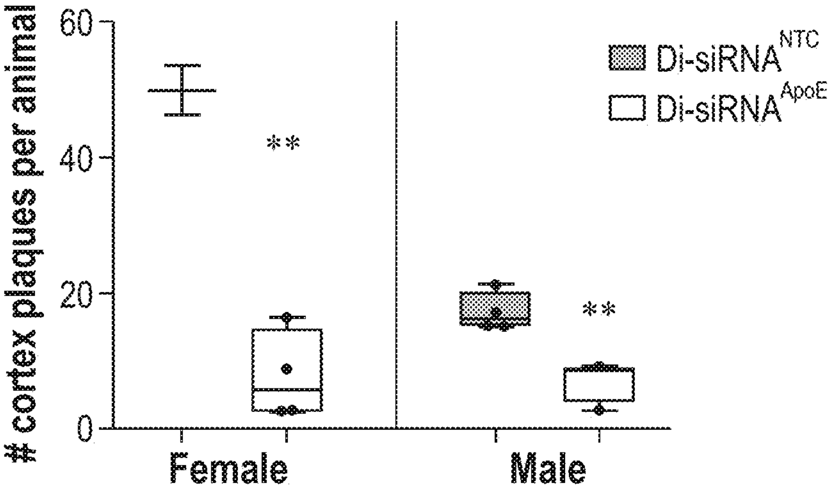
FIGS. 40A-40C include graphs reporting the results of a sex-specific analysis between Di-siRNA$^{NTC}$ and Di-siRNA$^{APoE}$ treated mice.
Figure 40B:
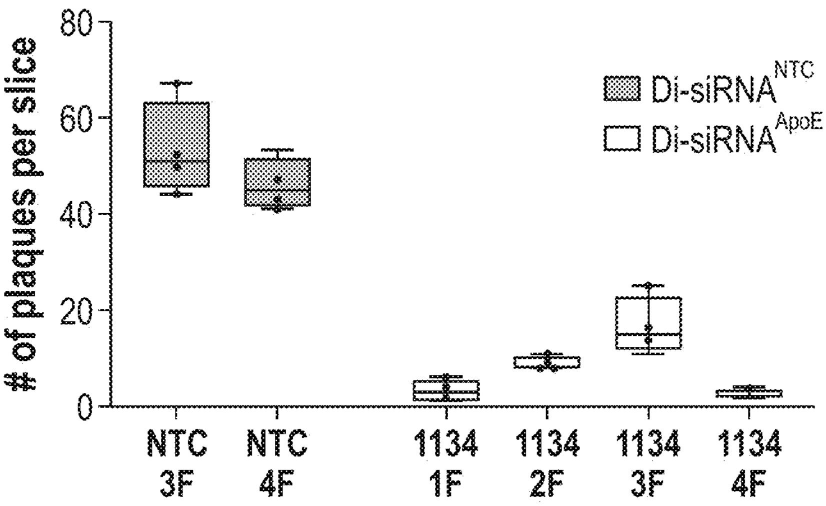
Figure 40C:
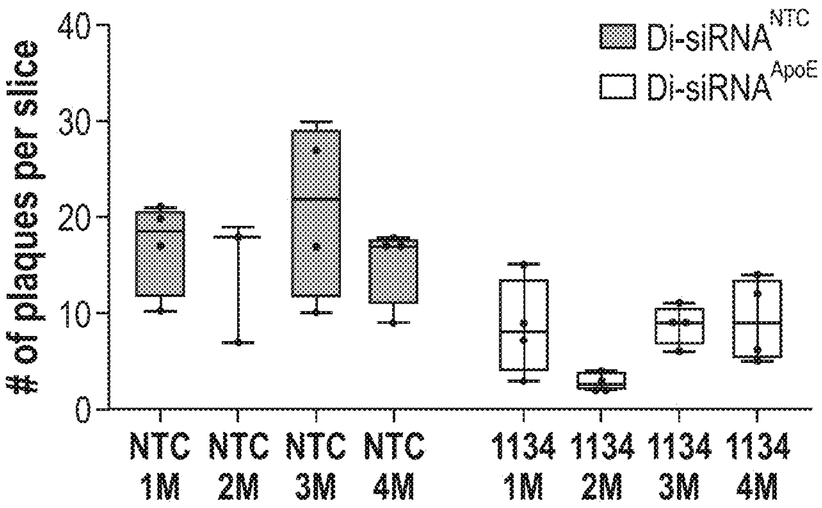
Figure 41:
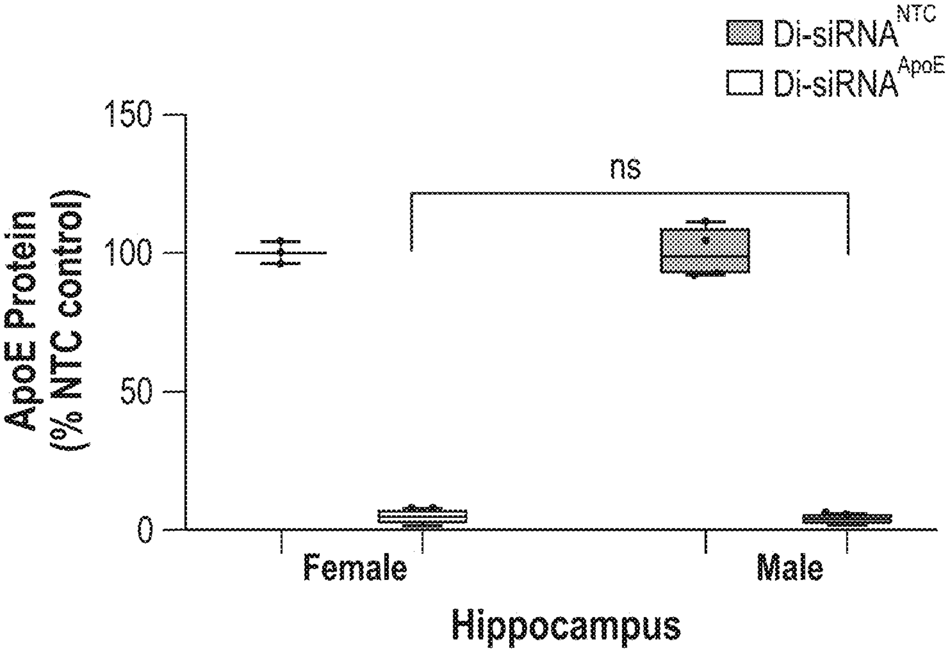
FIG. 41 is a graph reporting the impact of sex on silencing efficacy by Di-siRNA$^{ApoE}$.

Due to the historical and observed worsening in phenotype in female mice, sex-specific analysis was performed between Di-siRNA$^{NTC}$ and Di-siRNA$^{ApoE}$ treated mice. As reported in FIG. 40, significant differences were observed between both male and female groups; however the difference in female mice seemed to be more drastic. The data reported in FIG. 41 also shows that sex had no impact on silencing efficacy.

Figure 42A:
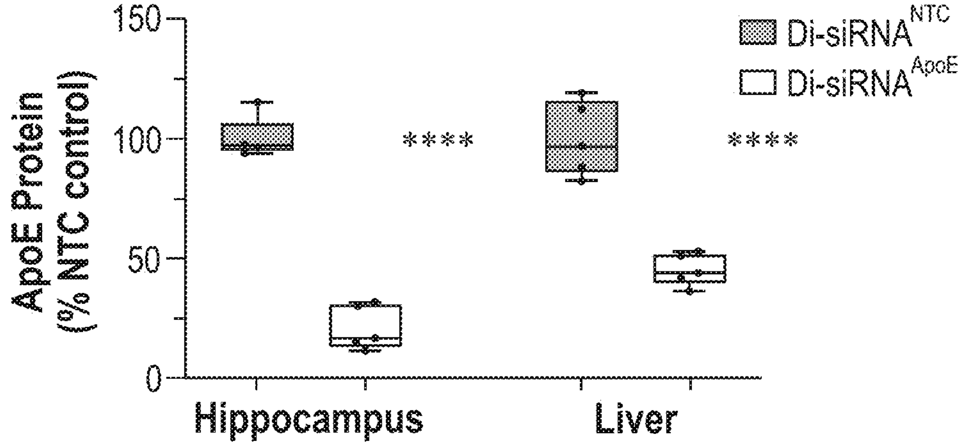
FIGS. 42A-42B show that the novel Di-siRNA ApoE 1156 silences ApoE4 in the brain and spinal cord.
Figure 42A:
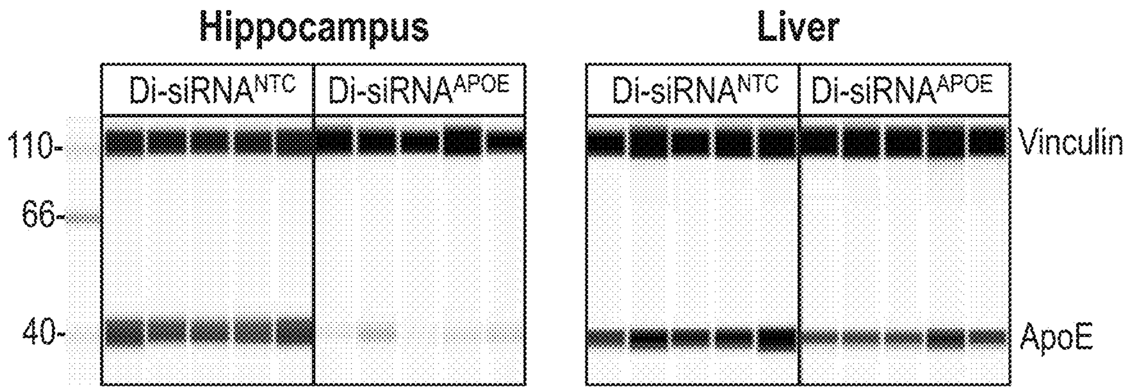
Figure 42B:
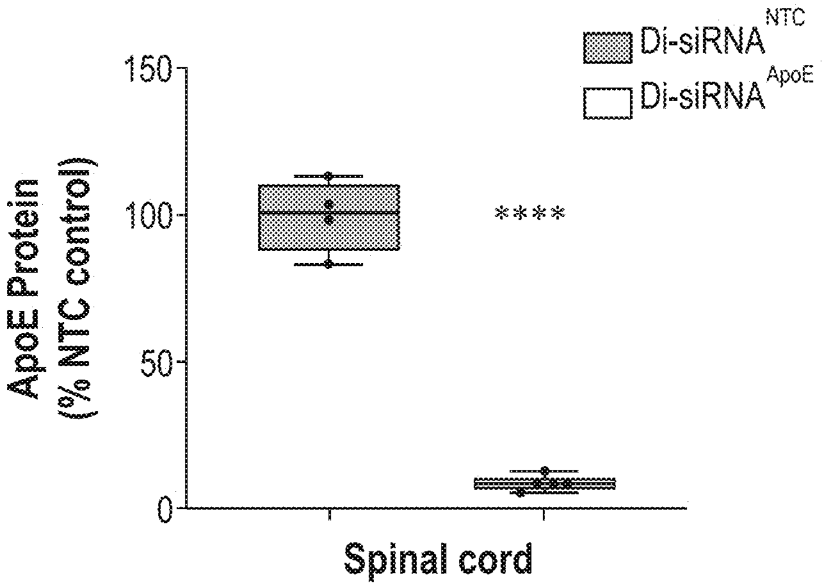
Figure 42B:
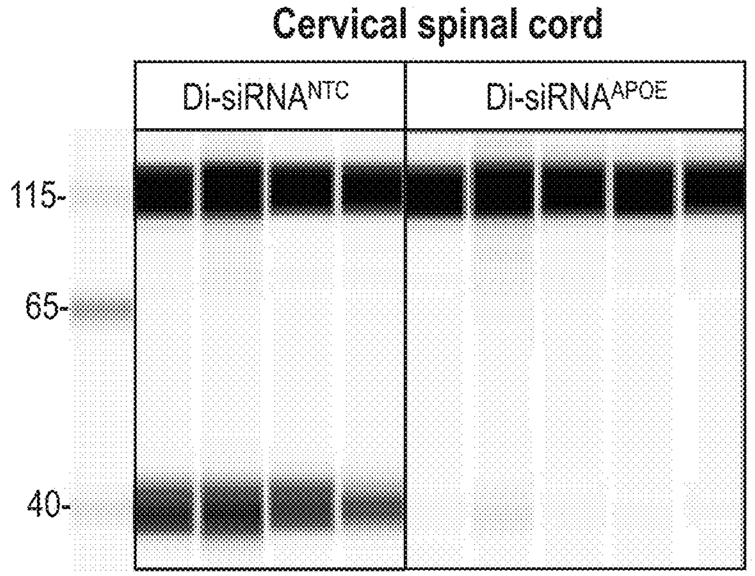

Previous reports using oligonucleotides to silence human ApoE use sequences that demonstrate a ~50% target mRNA and protein silencing after ICV injection of ~400 ug. In contrast, 1 month after injection of 237 μg of the novel Di-siRNA$^{ApoE}$ 1156 targeting human ApoE (E3 and E4), protein silencing of about 80-90% was found in the hippocampus (FIG. 42A) and spinal cord (FIG. 42B).

Figure 45:
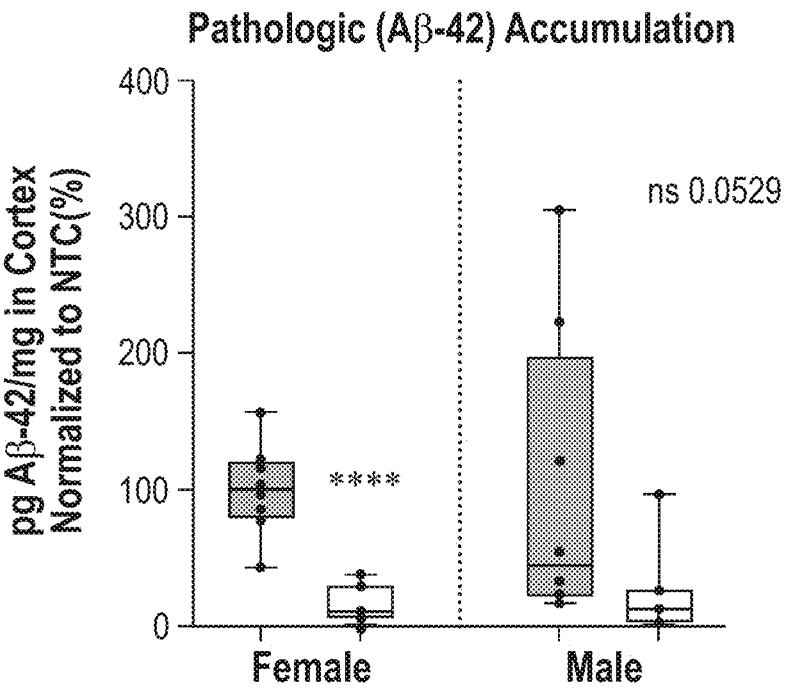
FIG. 45 illustrates the measurement of pathologic amyloid beta-42 in picograms per milligram cortex tissue. The results were measured in female and male mice separately. Left data points for each gender correspond to a non-targeting control Di-siRNA and right data points correspond to Di-siRNA targeting APOE.
Figure 46A:
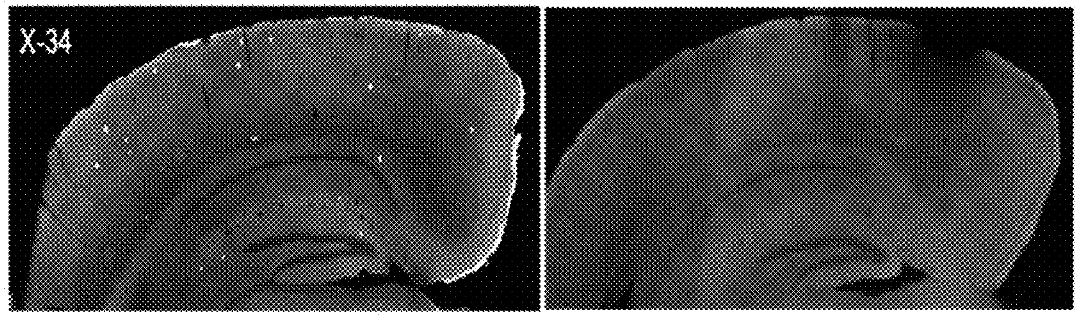
FIGS. 46A-46C illustrate mouse cortex staining (FIG. 46A) and relative quantification (FIG. 46B) of X-34 positive plaques and APP6E10/LAMP1 positive plaques (FIG. 46C). For FIG. 46A and FIG. 46B, the results were measured in female and male mice separately. Left data points for each gender correspond to a non-targeting control Di-siRNA and right data points correspond to Di-siRNA targeting APOE. For FIG. 46C, the results were compared to a GalNAc-conjugated APOE siRNA.
Figure 46B:
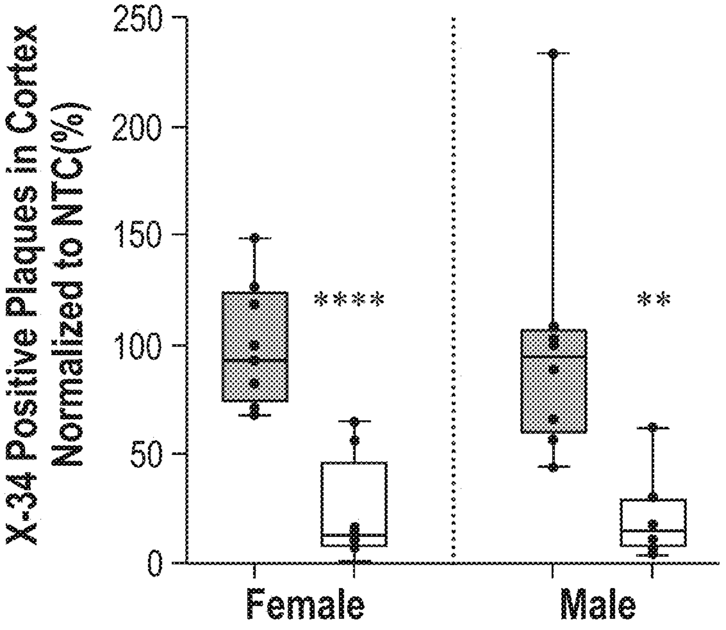
Figure 46C:
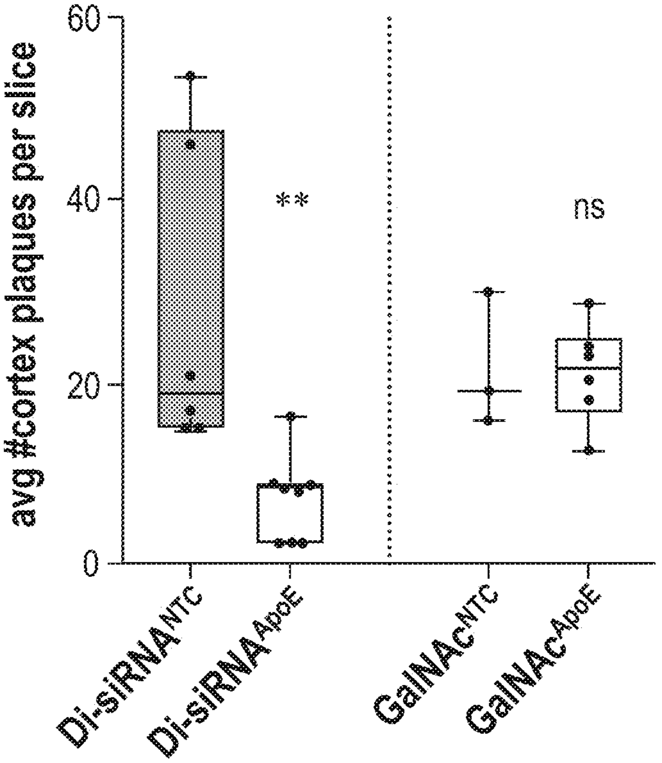

Additional cortical staining was performed to demonstrate a reduction of neuropathology after administration of Di-siRNA$^{ApoE}$ 1156. Pathologic amyloid beta-42 was measured in female and male mice and a reduction of amyloid beta-42 content was observed (FIG. 45). Moreover, the X-34 stain was used to image protein aggregates in the mouse cortex. A reduction in X-34 positive plaques was also observed with Di-siRNA$^{ApoE}$ compared to control (FIG. 46A and FIG. 46B). When comparing the number of APP6E10 and LAMP1 positive plaques in the mouse cortex, it was observed that a GalNAc-conjugates APOE siRNA had no effect, demonstrating that the Di-siRNA$^{ApoE}$ format was important for reducing neuropathology (FIG. 46C).

Figure 47:
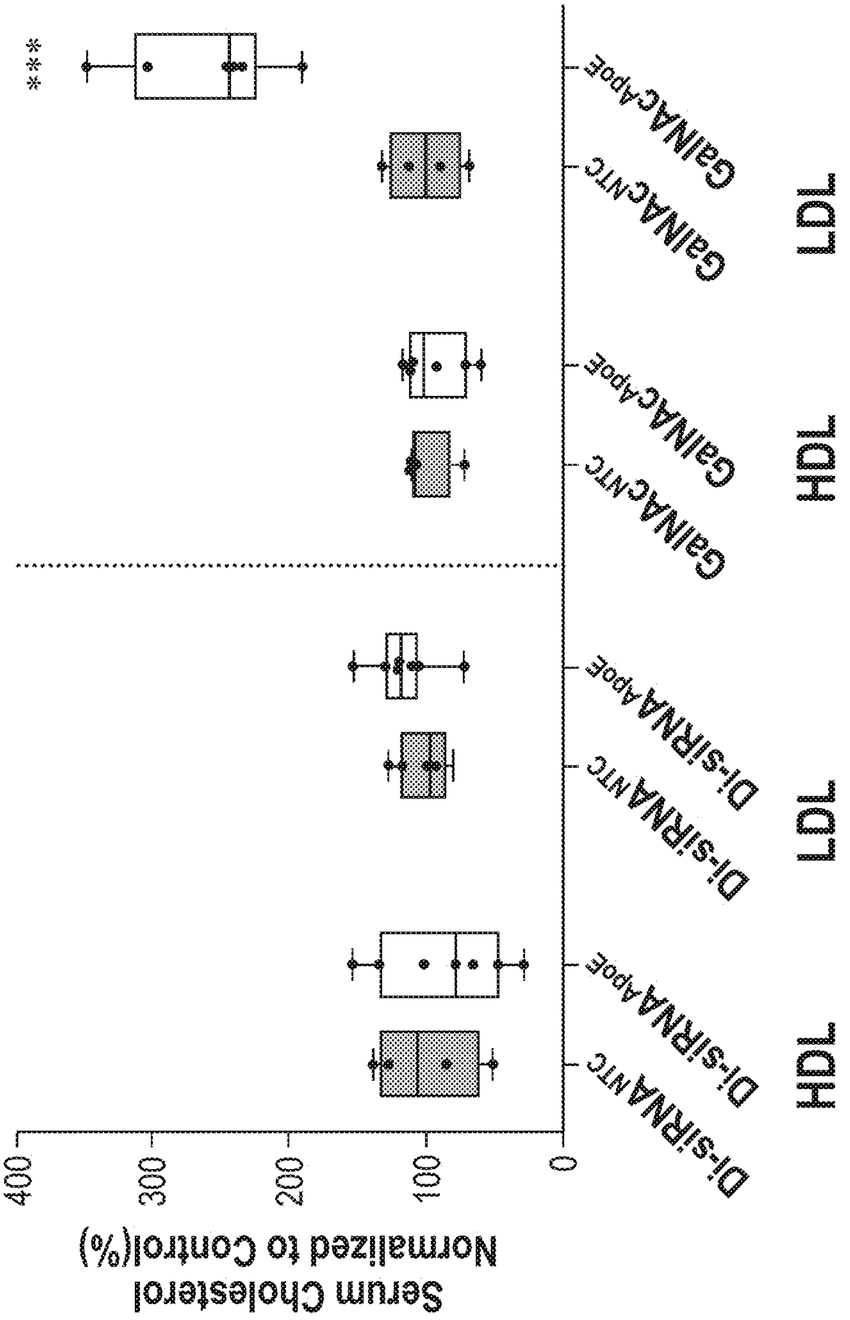
FIG. 47 illustrates the measurement of serum cholesterol (HDL and LDL levels) with Di-siRNA targeting APOE and GalNAc-conjugated siRNA targeting APOE.

To demonstrate that the Di-siRNA$^{ApoE}$ does not impact serum cholesterol, Di-siRNA$^{ApoE}$ was injected into the APP/PSEN1 mouse model and compared to a GalNAc conjugated APOE siRNA. The Di-siRNA$^{ApoE}$ was injected at 237 μg via bilateral ICV. 2 months after injection, LDL and HDL levels were determined. These results were compared to the GalNAc conjugated siRNA, which were injected at 10 mg/kg subcutaneously. As shown in FIG. 47, Di-siRNA$^{ApoE}$ did not affect HDL or LDL levels, while silencing APOE in the liver (via the GalNAc conjugate) resulted in an increase in LDL levels.

Figure 48A:
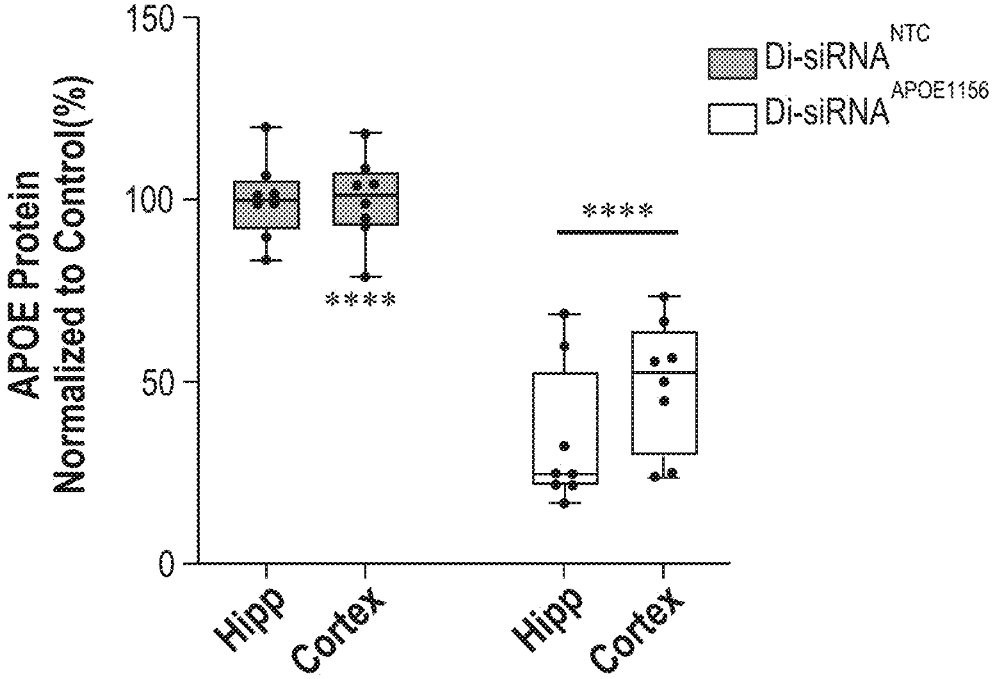
FIGS. 48A-48B illustrate the measurement of APOE protein levels in the hippocampus and cortex of the 3×-Tg-AD mouse model, 4-months after injection of Di-siRNA ApoE 1156.
Figure 48B:
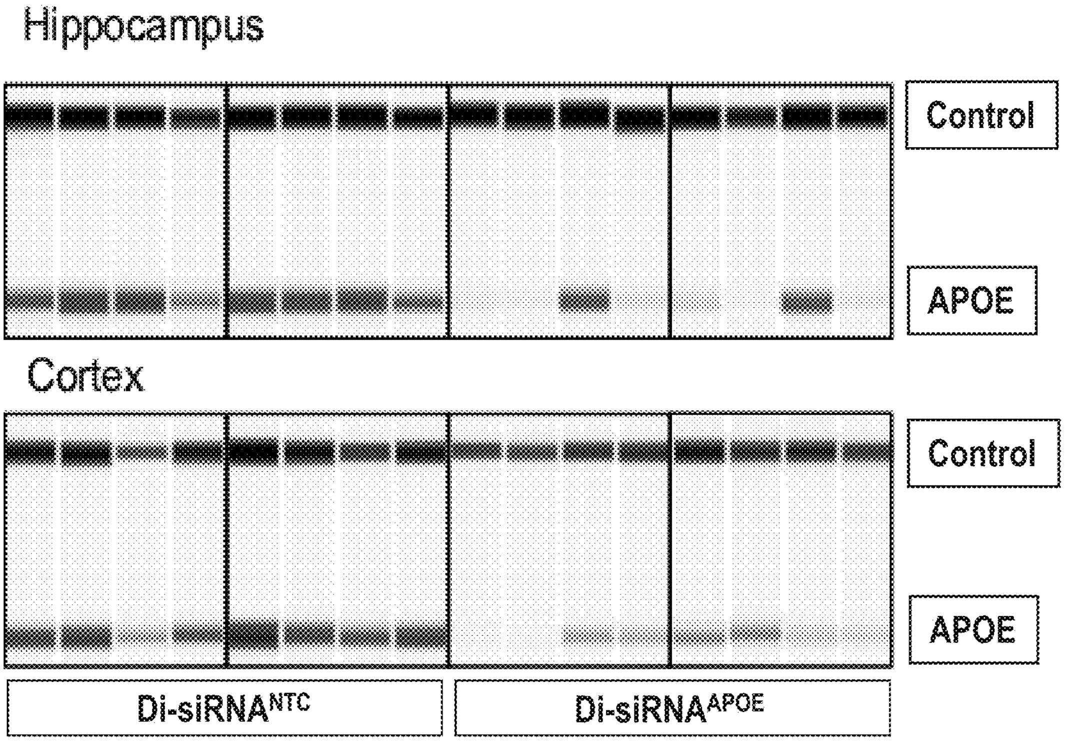

The efficacy of Di-siRNA$^{ApoE}$ 1156 was further tested in the triple transgenic mouse model of Alzheimer's disease (3×Tg-AD) over a 4-month study to demonstrate long-term silencing of APOE in the central nervous system. The 3×Tg-AD mice were injected with 237 μg of Di-siRNA$^{ApoE}$ and APOE protein levels were measured 4-months after injection. As shown in FIG. 48A and FIG. 48B, Di-siRNA$^{ApoE}$ potently inhibited APOE in the hippocampus and cortex, even after a 4-month period post injection.

Figure 49A:
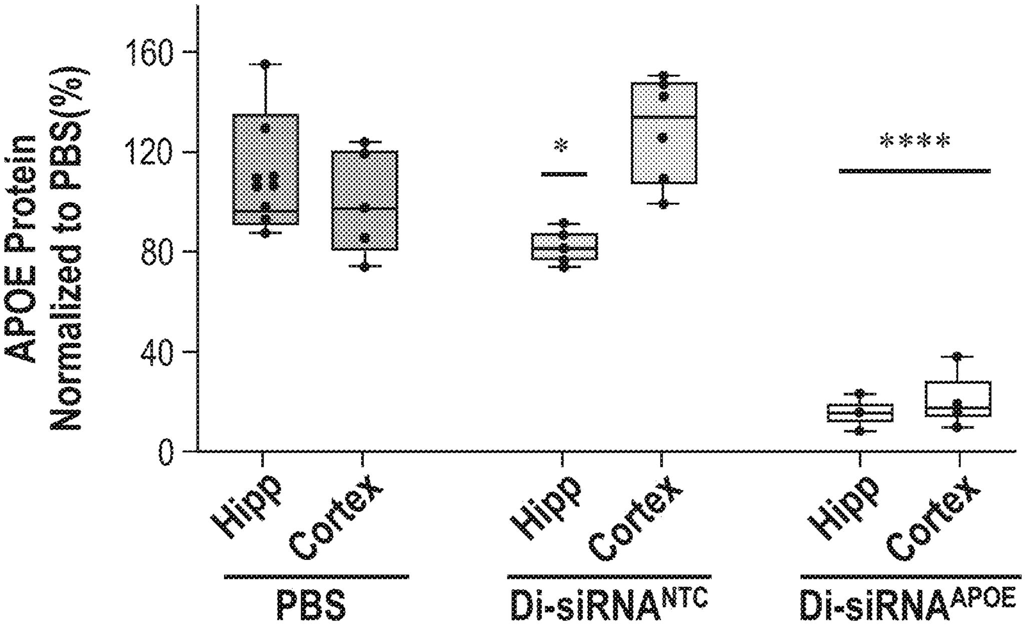
FIGS. 49A-49B illustrate the measurement of APOE protein levels in the hippocampus and cortex of the 3×-Tg-AD mouse model, 1-month after injection of Di-siRNA ApoE 1133.
Figure 49B:
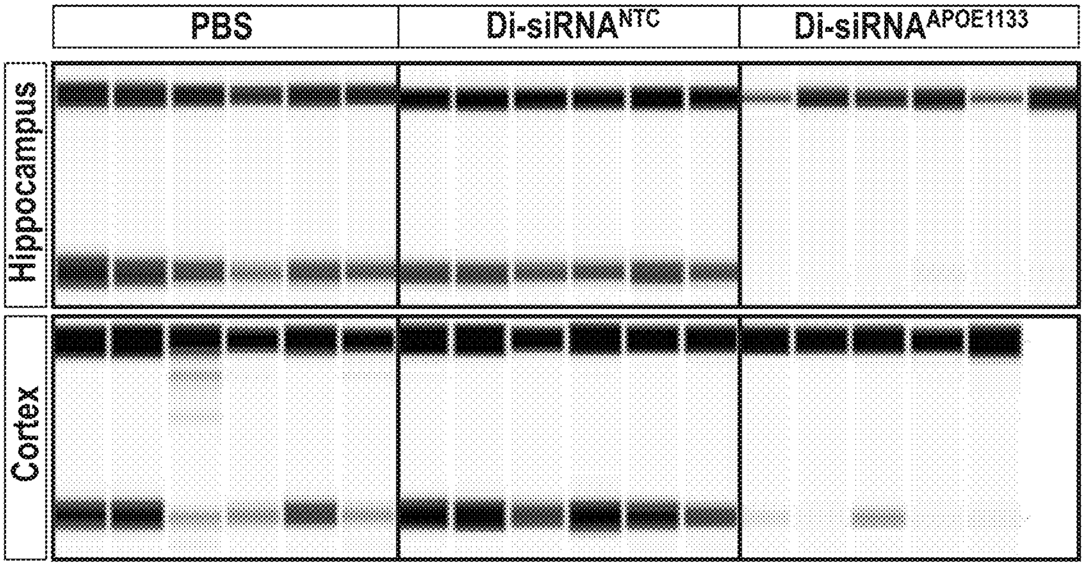

An additional APOE target was tested in a 2'-O-methyl rich pattern, as shown in FIG. 43. Mice were injected with Di-siRNA$^{ApoE}$ 1133 as described above, and APOE protein levels were determined 1-month after injection. As shown in FIG. 49A and FIG. 49B, Di-siRNA$^{ApoE}$ 1133 potently inhibited APOE in the hippocampus and cortex.

Figure 50:
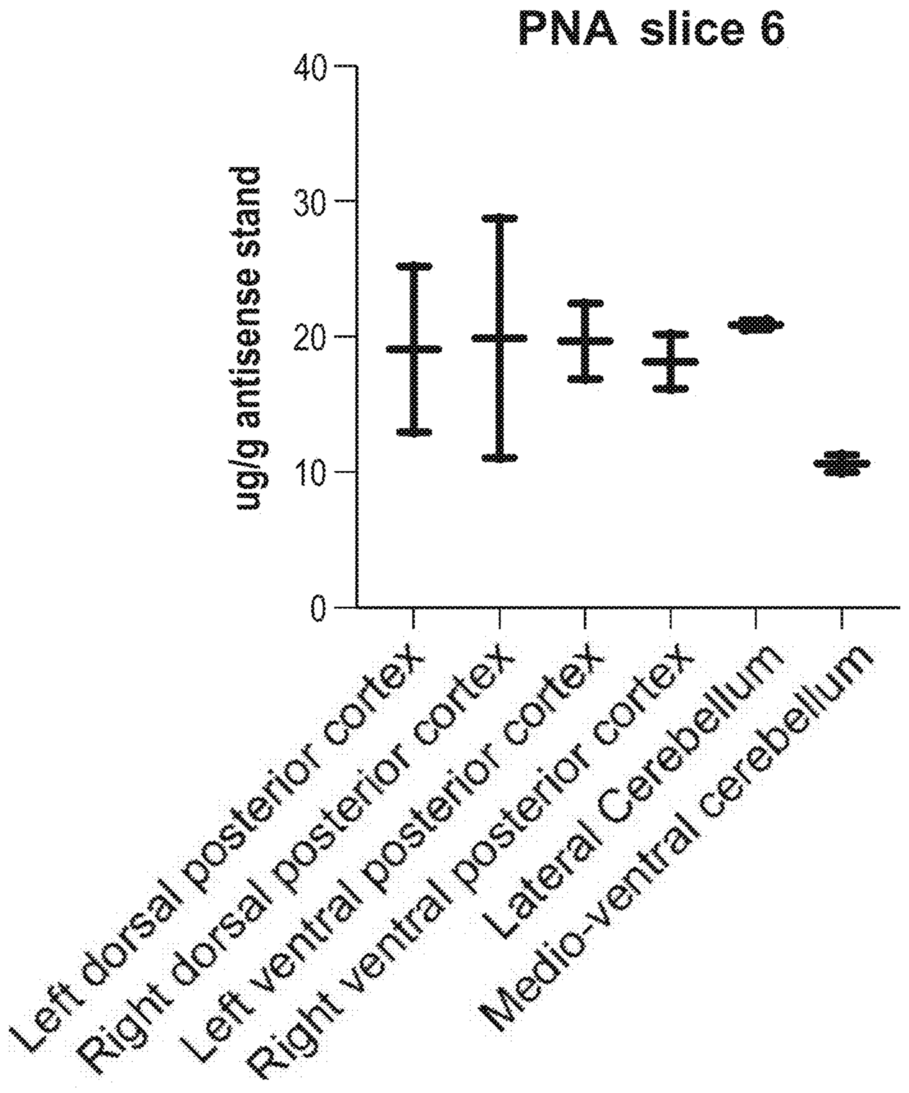
FIG. 50 illustrates the accumulation of siRNA in several regions of the posterior cortex of non-human primates (NHPs). The NHPs were injected with 25 mg of Di-siRNA ApoE 1133 into the cistema magna and siRNA accumulation was assessed 2-months post-injection.

To further demonstrate efficacy of the ApoE siRNAs of the invention, non-human primates (NHPs) were injected with 25 mg of Di-siRNA$^{ApoE}$ 1133 into the cistema magna. 2-months post-injection, Di-siRNA$^{ApoE}$ 1133 guide strand accumulation was measured in several regions of the posterior cortex and cerebellum. As shown in FIG. 50, high levels of siRNA accumulated in the sampled tissues, with an average accumulation of 20 μg siRNA/gram tissue.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), Current Protocols in Molecular Biology, John Wiley &Sons, NY (1993);

Ausubel, F. M. et al. eds., Short Protocols in Molecular Biology (4th Ed. 1999) John Wiley & Sons, NY. (ISBN 0-471-32938-X);

Controlled Drug Bioavailability, Drug Product Design and Performance, Smolen and Ball (eds.), Wiley, New York (1984);

Giege, R. and Ducruix, A. Barrett, Crystallization of Nucleic Acids and Proteins, a Practical Approach, 2nd ea., pp. 20 1-16, Oxford University Press, New York, New York, (1999);

Goodson, in Medical Applications of Controlled Release, vol. 2, pp. 115-138 (1984);

Hammerling, et al., in: Monoclonal Antibodies and T-Cell Hybridomas 563-681 (Elsevier, N.Y., 1981;

Harlow et al., Antibodies: A Laboratory Manual, (Cold Spring Harbor Laboratory Press, 2nd ed. 1988);

Kabat et al., Sequences of Proteins of Immunological Interest (National Institutes of Health, Bethesda, Md. (1987) and (1991);

Kabat, E. A., et al. (1991) Sequences of Proteins of Immunological Interest, Fifth Edition, U.S. Department of Health and Human Services, NIH Publication No. 91-3242;

Kontermann and Dubel eds., Antibody Engineering (2001) Springer-Verlag. New York. 790 pp. (ISBN 3-540-41354-5).

Kriegler, Gene Transfer and Expression, A Laboratory Manual, Stockton Press, NY (1990);

Lu and Weiner eds., Cloning and Expression Vectors for Gene Function Analysis (2001) BioTechniques Press. Westborough, MA. 298 pp. (ISBN 1-881299-21-X).

Medical Applications of Controlled Release, Langer and Wise (eds.), CRC Pres., Boca Raton, Fla. (1974);

Old, R. W. & S. B. Primrose, Principles of Gene Manipulation: An Introduction To Genetic Engineering (3d Ed. 1985) Blackwell Scientific Publications, Boston. Studies in Microbiology; V.2:409 pp. (ISBN 0-632-01318-4).

Sambrook, J. et al. eds., Molecular Cloning: A Laboratory Manual (2d Ed. 1989) Cold Spring Harbor Laboratory Press, NY. Vols. 1-3. (ISBN 0-87969-309-6).

Sustained and Controlled Release Drug Delivery Systems, J. R. Robinson, ed., Marcel Dekker, Inc., New York, 1978

Winnacker, E. L. From Genes to Clones: Introduction to Gene Technology (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A di-branched RNA compound comprising:

two RNA molecules each comprising 15 to 50 bases in length, and a region of complementarity of at least 14 contiguous nucleotides which is 100% complementary to an Apolipoprotein E (ApoE) mRNA nucleic acid sequence of SEQ ID NO: 5 or a region of complementarity of at least 14 contiguous nucleotides which is 100% complementary to an ApoE mRNA nucleic acid sequence of SEQ ID NO: 6, wherein each RNA molecule comprises a double stranded RNA (dsRNA) comprising a sense strand and an antisense strand, and wherein the two RNA molecules are connected to one another by one or more moieties independently selected from a linker, a spacer and a branching point.

2. A branched oligonucleotide compound comprising two or more nucleic acids, wherein:

each nucleic acid comprises 15 to 50 bases in length, each nucleic acid comprises a double stranded RNA (dsRNA) comprising a sense strand and an antisense strand, each antisense strand independently comprises a region of complementarity of at least 14 contiguous nucleotides which is 100% complementary to SEQ ID NO: 5 or a region of complementarity of at least 14 contiguous nucleotides which is 100% complementary to SEQ ID NO: 6, and the two or more nucleic acids are covalently connected to one another.

3. A branched oligonucleotide compound comprising two or more nucleic acids, wherein:

each nucleic acid comprises 15 to 50 bases in length, each nucleic acid comprises a double stranded RNA (dsRNA) comprising a sense strand and an antisense strand, the sense strand has a sequence as set forth in SEQ ID NO: 4, and the two or more nucleic acids are covalently connected to one another.

4. The branched oligonucleotide compound of claim 2, wherein the antisense strand comprises a 5' end and a 3' end and:

(1) a region of three contiguous 2'-fluoro-ribonucleotides;

(2) the nucleotides at positions 2 and 14 from the 5' end are not 2'-methoxy-ribonucleotides;

(3) the nucleotides are connected via phosphodiester or phosphorothioate linkages;

(4) the nucleotides at positions 1 to 7 from the 3' end are connected to adjacent nucleotides via phosphorothioate linkages; and (5) the nucleotides at positions 1-2 from the 5' end are connected to each other via phosphorothioate linkages.

5. A compound of formula (I):

L—(N)$_n$ (I)

wherein:

L comprises an ethylene glycol chain, an alkyl chain, a peptide, an RNA, a DNA, a phosphate, a phosphonate, a phosphoramidate, an ester, an amide, a triazole, or combinations thereof;

N is a double stranded RNA (dsRNA) comprising 15 to 35 bases in length comprising a sense strand and an antisense strand, wherein:

the antisense strand comprises a region of complementarity of at least 14 contiguous nucleotides which is 10000 complementary to SEQ ID NO: 5 or a region of complementarity of at least 14 contiguous nucleotides which is 100% o complementary to SEQ ID NO: 6, and the sense strand and the antisense strand each independently comprises one or more chemical modifications; and n is 2, 3, 4, 5,6, 7, or 8.

6. The compound of claim 5, having a structure selected from formulas (I-1)-(I-9):

N—L—N (I-1)

N—S—L—S—N (I-2)

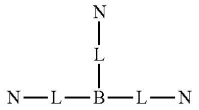

(I-3)

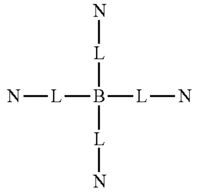

(I-4)

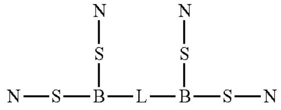

(I-5)

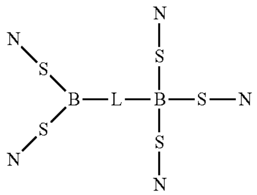

(I-6)

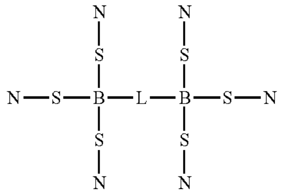

(I-7)

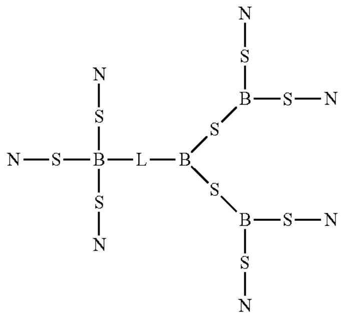

(I-8)

-continued
(I-9)
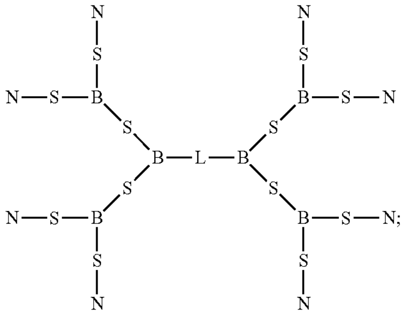
-continued
$R^2$
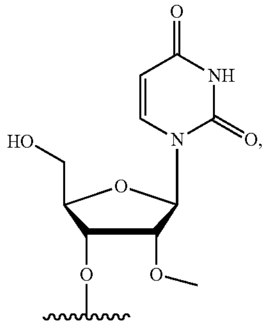
and/or
wherein L is of structure L1:
(L1)
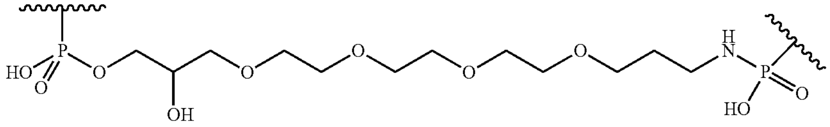
or
wherein L is of structure L2:
(L2)
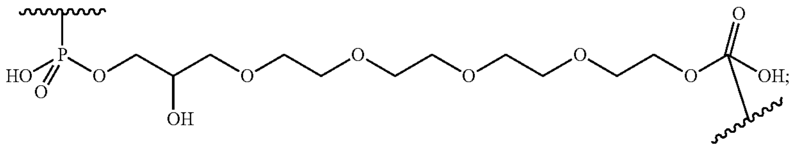
B is a branch point;
S is a spacer; and/or
wherein the antisense strand comprises a 5' terminal group R selected from the group consisting of:
$R^1$
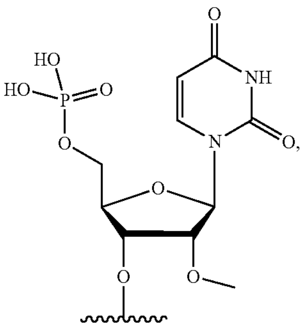
-continued
$R^3$
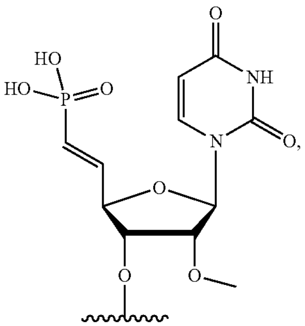

-continued
R4
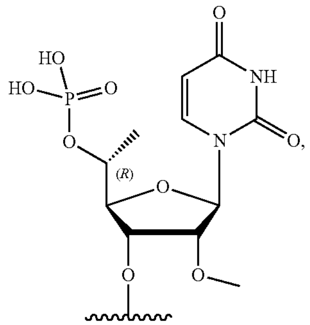
R5
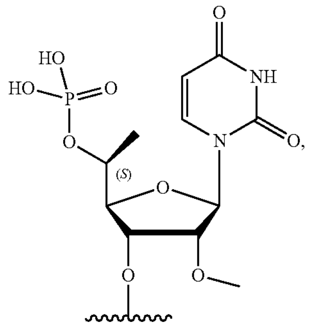
R6
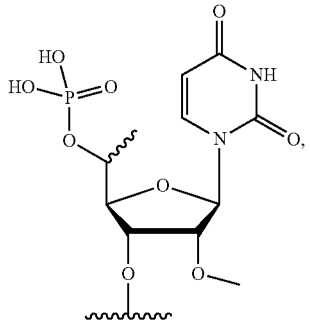
-continued
R7
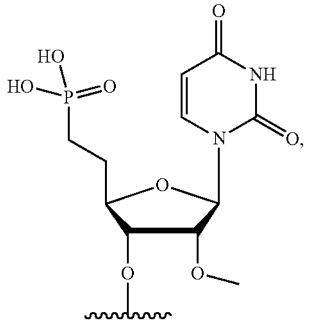
and
R8
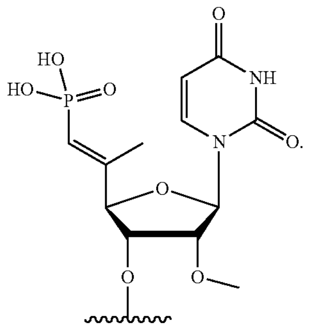
7. The compound of claim 5, having the structure of formula (II):
(II)
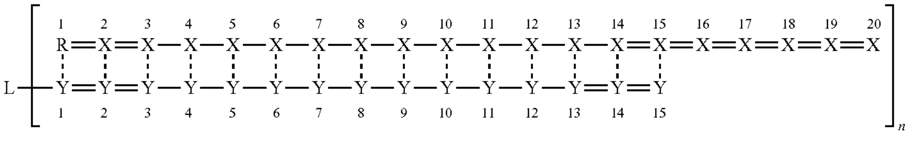

wherein

R is a nucleotide;

X, for each occurrence, independently, is selected from adenosine, guanosine, uridine, cytidine, and a chemically-modified derivative thereof;

Y, for each occurrence, independently, is selected from adenosine, guanosine, uridine, cytidine, and a chemically-modified derivative thereof;

— represents a phosphodiester internucleoside linkage;

= represents a phosphorothioate internucleoside linkage; and

--- represents, individually for each occurrence, a base-pairing interaction or a mismatch; or having the structure of formula (IV):

(IV)

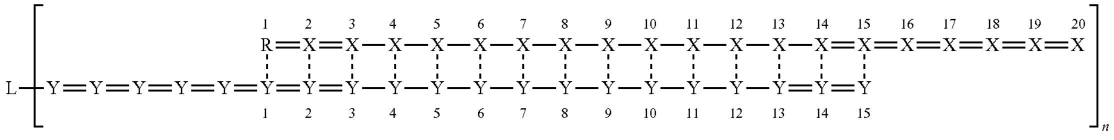

wherein

X, for each occurrence, independently, is selected from adenosine, guanosine, uridine, cytidine, and a chemically-modified derivative thereof;

Y, for each occurrence, independently, is selected from adenosine, guanosine, uridine, cytidine, and a chemically-modified derivative thereof;

— represents a phosphodiester internucleoside linkage;

= represents a phosphorothioate internucleoside linkage; and

--- represents, individually for each occurrence, a base-pairing interaction or a mismatch.

8. A pharmaceutical composition for inhibiting the expression of the ApoE gene in a mammalian central nervous system, comprising the di-branched RNA compound of claim 1, and a pharmaceutically acceptable carrier.

9. A di-branched RNA compound comprising:

two RNA molecules each comprising 15 to 50 bases in length, wherein each RNA molecule comprises a double stranded RNA (dsRNA) comprising a sense strand and an antisense strand, wherein the sense strand has a sequence as set forth in SEQ ID NO: 4, and wherein the two RNA molecules are connected to one another by one or more moieties independently selected from a linker, a spacer and a branching point.

10. The branched oligonucleotide compound of claim 2, wherein the two or more nucleic acids are covalently connected to one another by one or more moieties selected from a linker, a spacer and a branching point.

11. The branched oligonucleotide compound of claim 2, wherein:

each dsRNA comprises 15 to 25 base pairs in length; and each nucleic acid independently comprises at least one modified nucleotide; and/or the antisense strand has fewer than 3 mismatches with SEQ ID NO: 6.

12. The branched oligonucleotide compound of claim 11, wherein the at least one modified nucleotide comprises a 2'-O-methyl modified nucleotide, a 5'-phosphorothioate group, a terminal nucleotide linked to a cholesteryl derivative or dodecanoic acid bisdecylamide group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

13. The compound of claim 5, wherein the formula (I) further comprises one or more branch point B, and one or more spacer S covalently connected to at least one of L and N, wherein:

the one or more branch point B is independently for each occurrence a polyvalent organic species; and the one or more spacer S comprises independently for each occurrence an ethylene glycol chain, an alkyl chain, a peptide, an RNA, a DNA, a phosphate, a phosphonate, a phosphoramidate, an ester, an amide, a triazole, or a combination thereof.

14. The di-branched RNA compound of claim 1, wherein the antisense strand comprises no more than 3 mismatches with a sequence of at least 20 contiguous nucleotides of SEQ ID NO: 2.

15. The di-branched RNA compound of claim 1, wherein the antisense strand comprises no more than 2 mismatches with 5' CCUAGUUUAAUAAAGAUUCA 3' (SEQ ID NO: 6).

16. The branched oligonucleotide compound of claim 2, wherein the antisense strand comprises no more than 2 mismatches with SEQ ID NO: 6.

17. The compound of claim 5, wherein the antisense strand comprises no more than 2 mismatches with SEQ ID NO: 6.

* * * * *

SEQUENCE LISTING

<160> NUMBER OF SEQ ID NOS: 40

<210> SEQ ID NO 1
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1
guuuaauaaa gauucaccaa guuucacgca aa 32

<210> SEQ ID NO 2
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 2
uggacccuag uuuaauaaag auucaccaag 30

<210> SEQ ID NO 3
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
cuaguuuaau aaagauucac caaguuucac 30

<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
gauucaccaa guuua 15

<210> SEQ ID NO 5
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5
caaguuucac gcaaa 15

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
ccuaguuuaa uaaagauuca 20

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: See specification as filed for detailed description of substitutions and preferred embodiments

<400> SEQUENCE: 7

```
Gln Gln Gln Gln Gln
1               5
```

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: See specification as filed for detailed description of substitutions and preferred embodiments

<400> SEQUENCE: 8

```
Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln
        35
```

<210> SEQ ID NO 9
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 9
ccuugcuuaa uaaagauucu ccgagcacau u 31

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 10
uuggauaugg auguuguugc ag 22

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 11
ucucggagaa ucuuuauuaa gc 22

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 12
gcaacaacau ccauauccaa 20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 13
uuaauaaaga uucuccgaga 20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 14
uaaacuuggu gaaucuuuau 20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 15
uuugcgugaa acuuggugaa 20

<210> SEQ ID NO 16

<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
caggcaggaa gaugaagguu cugugggcug 30

<210> SEQ ID NO 17
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
uccuggggug gacccuaguu uaauaaagau 30

<210> SEQ ID NO 18
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 18 ggggugggacc cuaguuuaau aaagauucac 30

<210> SEQ ID NO 19
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 19
guuuaauaaa gauucaccaa guuucacgca 30

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
aggaagauga agguucugug 20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 21
ggguggaccc uaguuuaaua 20

<210> SEQ ID NO 22
<211> LENGTH: 20

-continued

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 22
ggacccuagu uuaauaaaga 20

<210> SEQ ID NO 23
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 23
uuaauaaaga uucaccaagu 20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
uaaagauuca ccaaguuuca 20

<210> SEQ ID NO 25
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
gaugaagguu cugug 15

<210> SEQ ID NO 26
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
gacccuaguu uaaua 15

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 27
cuaguuuaau aaaga 15

<210> SEQ ID NO 28
<211> LENGTH: 15
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 28

uuuaauaaag auuca                                                    15


<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

aaagauucac caagu                                                    15


<210> SEQ ID NO 30
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30

auucaccaag uuuca                                                    15


<210> SEQ ID NO 31
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31

cacagaaccu ucaucuuccu                                               20


<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32

uauuaaacua ggguccaccc                                               20


<210> SEQ ID NO 33
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33

ucuuuauuaa acuaggguce                                               20


<210> SEQ ID NO 34
<211> LENGTH: 20
<212> TYPE: RNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 34
ugaaucuuua uuaaacuagg 20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
acuuggugaa ucuuuauuaa 20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugaaacuugg ugaaucuuua 20

<210> SEQ ID NO 37
<211> LENGTH: 31
<212> TYPE: DNA
<213> ORGANISM: Mus sp.

<400> SEQUENCE: 37
tgtcctgcaa caacatccat atccagccag g 31

<210> SEQ ID NO 38
<211> LENGTH: 31
<212> TYPE: DNA
<213> ORGANISM: Mus sp.

<400> SEQUENCE: 38
ccttgcttaa taaagattct ccgagcacat t 31

<210> SEQ ID NO 39
<211> LENGTH: 30
<212> TYPE: DNA
<213> ORGANISM: Homo sapiens

<400> SEQUENCE: 39
gtttaataaa gattcaccaa gtttcacgca 30

<210> SEQ ID NO 40
<211> LENGTH: 32
<212> TYPE: DNA
<213> ORGANISM: Homo sapiens

<400> SEQUENCE: 40
gtttaataaa gattcaccaa gtttcacgca aa 32